United States Patent
Hou et al.

(10) Patent No.: US 11,786,552 B2
(45) Date of Patent: Oct. 17, 2023

(54) THERAPEUTIC COMPOSITIONS AND APPLICATIONS THAT COMPRISE NUCLEIC ACIDS AND ADOPTIVELY TRANSFERRED IMMUNE CELL

(71) Applicants: HANGZHOU CONVERD CO., LTD., Zhejiang (CN); Yafei Hou, Mountain View, CA (US)

(72) Inventors: Yafei Hou, Mountain View, CA (US); Fang Hu, Hangzhou (CN); Jipo Sheng, Hangzhou (CN); Xiankui Tan, Hangzhou (CN); Can Chen, Hangzhou (CN)

(73) Assignees: HANGZHOU CONVERO CO., LTD., Hangzhou (CN); Yafei Hou, Mountain View, CA (US)

( * ) Notice: Subject to any disclaimer, the term of this patent is extended or adjusted under 35 U.S.C. 154(b) by 577 days.

(21) Appl. No.: 16/798,465

(22) Filed: Feb. 24, 2020

(65) Prior Publication Data

US 2020/0289567 A1 Sep. 17, 2020

Related U.S. Application Data

(63) Continuation-in-part of application No. PCT/CN2019/102584, filed on Aug. 26, 2019.

(30) Foreign Application Priority Data

Aug. 24, 2018 (CN) .......................... 201810972316.5

(51) Int. Cl.
| | |
|---|---|
| *A61K 35/17* | (2015.01) |
| *A61K 39/00* | (2006.01) |
| *A61K 35/768* | (2015.01) |
| *A61K 38/28* | (2006.01) |
| *A61K 38/17* | (2006.01) |
| *A61P 35/00* | (2006.01) |
| *C07K 14/725* | (2006.01) |
| *C07K 14/74* | (2006.01) |
| *C12N 7/00* | (2006.01) |

(52) U.S. Cl.
CPC ............ *A61K 35/17* (2013.01); *A61K 35/768* (2013.01); *A61K 38/1774* (2013.01); *A61K 38/28* (2013.01); *A61K 39/0011* (2013.01); *A61P 35/00* (2018.01); *C07K 14/7051* (2013.01); *C07K 14/70539* (2013.01); *C12N 7/00* (2013.01)

(58) Field of Classification Search
CPC .. A61K 35/17; A61K 35/768; A61K 38/1774; A61K 38/28; A61K 39/0011; A61P 35/00; C07K 14/7051; C07K 14/70539; C12N 7/00

See application file for complete search history.

(56) References Cited

U.S. PATENT DOCUMENTS

| | | | | |
|---|---|---|---|---|
| 5,585,237 A | * | 12/1996 | Oppermann | ........... C12N 15/85 435/325 |
| 9,018,182 B2 | | 4/2015 | Koh | |
| 9,540,657 B2 | * | 1/2017 | Yu | ........... C12N 15/85 |
| 10,064,927 B2 | | 9/2018 | Peretz | |
| 11,000,560 B2 | | 5/2021 | Alemany et al. | |
| 2016/0250292 A1 | | 9/2016 | Hu | |
| 2019/0030151 A1 | | 1/2019 | Jones et al. | |
| 2019/0119350 A1 | | 4/2019 | Lu et al. | |
| 2019/0134174 A1 | | 5/2019 | Jones et al. | |
| 2021/0393686 A1 | * | 12/2021 | Hu | ........... C12N 15/86 |
| 2022/0339220 A1 | | 10/2022 | Hu | |

FOREIGN PATENT DOCUMENTS

| | | |
|---|---|---|
| CN | 104415335 A | 3/2015 |
| CN | 105802909 A | 7/2016 |
| CN | 107849111 A | 3/2018 |
| CN | 108137670 A | 6/2018 |
| CN | 108261426 A | 4/2019 |
| EP | 3067366 A1 | 9/2016 |
| TW | 201740958 A | 12/2017 |
| TW | 201805013 A | 2/2018 |
| WO | 2013177247 A1 | 11/2013 |
| WO | 2017075537 A1 | 5/2017 |
| WO | WO-2017152042 A2 * 9/2017 ............. A61K 39/00 |
| WO | 2017177204 A1 | 10/2017 |

OTHER PUBLICATIONS

Rao et al. E1A-induced apoptosis does not prevent replication of adenoviruses with deletion of E1b in majority of infected cancer cells. Cancer Gene Therapy. 2004; 11: 585-593. (Year: 2004).*
Stornaiuolo et al. KDEL and KKXX Retrieval Signals Appended to the Same Reporter Protein Determine Different Trafficking between Endoplasmic Reticulum, Intermediate Compartment, and Golgi Complex. Molecular Biology of the Cell, 2003; 14: 889-902. (Year: 2003).*

(Continued)

*Primary Examiner* — Arthur S Leonard
*Assistant Examiner* — Jianjian Zhu
(74) *Attorney, Agent, or Firm* — Renner, Otto, Boisselle & Sklar, LLP

(57) ABSTRACT

A therapeutic agent and method of administering the therapeutic agent for the treatment of tumors and/or cancers of a subject, the therapeutic agent comprising a first pharmaceutical composition comprising a first active ingredient in a first druggable vehicle, wherein the first active ingredient comprises a nucleic acid encoding a labelling polypeptide comprising one or more antigenic epitope peptides and/or encoding a MHC protein; a second pharmaceutical composition comprising a second active ingredient in a second druggable vehicle, wherein the second active ingredient comprises immune cells purified from peripheral blood or from tumor tissue and are cultured in vitro; wherein the nucleic acid when administered to the subject as part of the pharmaceutical composition causes the tumor cells and/or cancer cells of the subject to express the one or more antigenic epitope peptides to elicit an immune response of the immune cells.

13 Claims, 12 Drawing Sheets

Specification includes a Sequence Listing.

(56) References Cited

OTHER PUBLICATIONS

Thanasupawat et al. INSL5 is a novel marker for human enteroendocrine cells of the large intestine and neuroendocrine tumours. Oncology Reportes.2013; 29: 149-154. (Year: 2013).*

Berahovich et al. FLAG-tagged CD19-specific CAR-T cells eliminate CD19-bearing solid tumor cells in vitro and in vivo. Frontiers in Bioscience, Landmark, 2017, 22, 1644-1654. (Year: 2017).*

Extended European Search Report dated May 11, 2022, for corresponding European Patent Application No. 19851924.1.

Yangbing Zhao et al.; Primary Human Lymphocytes Transduced with NY-ESO-1 Antigen-Specific TCR Genes Recognize and Kill Diverse Human Tumor Cell Lines; The Journal of Immunology, Williams & Wilkins CO; Apr. 1, 2005; pp. 4415-4423; vol. 174, No. 7.

Remy Thomas et al.; NY-ESO-1 Based Immunotherapy of Cancer: Current Prospects; Frontiers in Immunology; May 1, 2018; pp. 1-14; vol. 9, Article 947.

Restriction Requirement dated Oct. 21, 2022, for corresponding U.S. Appl. No. 17/270,943.

Tam Nguyen-Hoai et al.; HER2/neu DNA vaccination by intradermal gene delivery in a mouse tumor model; Gene gun is superior to jet injector in inducing CTL responses and protective immunity; Dec. 2012; pp. 1537-1545; vol. 1, Issue 9, OncoImmunology.

Evripidis Lanitis et al.; A Human ErbB2-Specific T-Cell Receptor Confers Potent Antitumor Effector Functions in Genetically Engineered Primary Cytotoxic Lymphocytes; Aug. 2014; pp. 730-739; Human Gene Therapy.

Keith L. Knutson et al.; Clonal Diversity of the T-Cell Population Responding to a Dominant HLA-A2 Epitope of HIER-2/neu After Active Immunization in an Ovarian Cancer Patient; American Society for Histocompatibility and Immunogenetics; 2002; Human Immunology 63, pp. 547-557; Published by Elsevier Science Inc.

Lanlin Zhang et al.; Progress in T cell receptor-gene engineered T cell immunotherapy for solid tumors; Mar. 2018; pp. 256-263; Tumor vol. 38; China Academic Journal Electronic Publishing House.

Su-Juan Ma et al. .; Construction of TCR gene modified cytotoxic T lymphocytes and its applications; Sep. 2012; pp. 650-654; vol. 39, No. 9; J Int Oncol.

Fei-Fei Luo; Tumor antigen-specific T cell immunotherapy; Sep. 2017; pp. 816-822; vol. 29, No. 9; Fudan University, Shanghai, China; Chinese Bulletin of Life Sciences.

International Search Report and English translation of Written Opinion dated Dec. 3, 2019, for International Patent Application No. PCT/CN2019/102584.

Office Action dated Jan. 10, 2023, for corresponding U.S. Appl. No. 17/270,943.

Konstantin Doronin et al.; Tumor-Specific, Replication-Competent Adenovirus Vectors Overexpressing the Adenovirus Death Protein; Journal of Virology; 2000; 74(13); pp. 6147-6155.

SCORE sequence alignment between 17270943-56 and Yu US9540657-486 (2022).

First Office Action dated approximately May 16, 2023 for corresponding Taiwanese Patent Application No. 108130349.

Office Action issued for corresponding Chinese National Stage Application No. 201810972316.5, dated Jul. 24, 2023.

Wang, Li, et al., "An endoplasmic reticulum retrieval signal sequence promotes MHC class I—presentation of exogenous CTL epitope peptides", Immunological Journal, vol. 22 No. 5, published Sep. 2006, DOI: 10. 13431 (translation of Abstract only).

Final Office Action issued for related US National Stage U.S. Appl. No. 17/270,943, dated May 5, 2023.

* cited by examiner

THERAPEUTIC COMPOSITIONS AND APPLICATIONS THAT COMPRISE NUCLEIC ACIDS AND ADOPTIVELY TRANSFERRED IMMUNE CELL

CROSS-REFERENCE TO RELATED APPLICATION(S)

This application has subject matter in common with: 1) PCT Patent Application Serial No. PCT/CN2019/102584, filed Aug. 26, 2019, for "Therapeutic Agent Comprising Nucleic Acid and TCR-Modified T Cells and Its Application", and 2) Chinese Patent Application Serial No. 201810972316.5, filed Aug. 24, 2018, for "Therapeutic Agent Comprising Nucleic Acid and TCR-Modified T Cells and Its Application", the entire disclosures of which are incorporated herein by reference.

This application claims priority to prior filed PCT Patent Application Serial No. PCT/CN2019/102584, filed Aug. 26, 2019, for "Therapeutic Agent Comprising Nucleic Acid and TCR-Modified T Cells and Its Application", which claims priority to the Chinese Patent Application Serial No. 201810972316.5, filed Aug. 24, 2018, for "Therapeutic Agent Comprising Nucleic Acid and TCR-Modified T Cells and Its Application".

SEQUENCE LISTING

The instant application contains a Sequence Listing which has been submitted electronically in ASCII format and is hereby incorporated by reference in its entirety. Said ASCII copy, created on Jun. 5, 2020 and named SYNIMM-P0001_SL.txt and is 92,136 bytes in size.

TECHNICAL FIELD

The present invention relates generally to the use of modified T cells that express specific T cell antigen receptors (TCR) to treat tumors and/or cancers; more specifically, to the use of therapeutic agents comprising (1) nucleic acid sequence encoding a labelling polypeptide comprising antigenic epitopes and/or a major histocompatibility complex (MEW) protein, and (2) modified T cells that express specific TCR.

BACKGROUND OF THE INVENTION

Adoptive cell therapy (ACT) with tumor-infiltrating lymphocytes (TIL), or the genetically modified T cells expressing specific T cell receptors (TCR-T) or chimeric antigen receptors (CAR-T) has been proven to be one of the most promising immunotherapy against cancer (N Engl J Med 2017; 377:2545-2554). Although CAR-T therapy targeting CD19 or BCMA has shown significant clinical efficacy to treat blood cancers, CAR-T has not yet shown a clear clinical benefit for the patients with solid tumors (J Immunother. 2019; 42:126-135). Adoptively transferring T cells generated from TILs or the T cells that are genetically modified to express the specific TCR against tumor antigens to the patients with solid tumors had shown clinical benefits (Adv Immunol. 2016; 130:279-94). Clinical trials of TCR-T therapies for various solid tumors are currently being conducted at different phases (Technol Cancer Res Treat. 2019; 1-13).

While adoptive T cell therapy is a promising approach to treat solid tumors, it still faces the obstacles that may limit its therapeutic function as well as its application. One limitation of T cell therapy is intra-tumor heterogeneity, characterized by an uneven tumor antigen expression in tumor cells (Int J Cancer. 2001 Jun. 15; 92(6): 856-60). Deficient expression of target antigens in a portion of tumor cells can make them escape the recognition and killing by the adoptively transferred T cells. In addition, the aberrant expression of the antigen processing and presenting machinery component, including HLA molecules, beta-2 microglobulin, TAP, tapasin, LMP and so on, frequently occurs in human tumors, which disrupts the function of tumor antigen specific T cells to eliminate tumor cells (J Natl Cancer Inst. 2013; 105(16):1172-87). Moreover, tumor-specific T cells recognize the epitope peptides that are presented by the major histocompatibility complex (MHC) proteins, they are only able to detect the target antigens on the tumor cells in the context of a particular MHC allele. However, the frequency of tumors concurrently harboring a specific target antigen and the cognate HLA allele that encodes the MHC molecules that can present the epitope derived from this antigen is usually very low. As a result, MHC restriction can remarkably limit the application scope of adaptive T therapy. Another factor affecting the anti-tumor effectiveness of adoptively transferred T cells is the immunosuppressive tumor microenvironment (TME), which impacts T cell proliferation, differentiation, cytotoxicity and migration (Curr Opin Immunol. 2016 April; 39:1-6).

Therefore, applicant(s) herein recognize(s), how to augment the sensitivity of adoptive T cells against tumors that express low or even absent target antigens that can be recognized by the adoptive T cells due to the mechanisms mentioned above, and how to expand the application scope of adoptive T cells to the patients lacking of the HLA allele that encodes MHC molecules that can present the antigenic epitopes derived from a tumor antigen are the major challenges in the field. Combining the adoptive T cell therapy, including the TCR-T cell therapy, with oncolytic virus therapy is the direction to overcome the hurdles that adoptive T cell therapies currently encounter.

SUMMARY

The invention provides, among other things, methods and compositions for treating tumors and/or cancers. More particularly, the invention is related therapeutic agents or compositions comprising immune cells (e.g., TCR-modified T cells) and nucleic acids encoding labelling polypeptides and/or exogenous HLA, and their therapeutic applications.

In some embodiments, the invention provides:

(1) A therapeutic agent for the treatment of tumors and/or cancers of a subject, comprising:

(a) a first composition, the said first composition comprises a first active ingredient in a first druggable vehicle. The said the first active ingredient comprises or contains nucleic acid encoding a labelling polypeptide, and/or a MHC protein; in an aspect, the nucleic acid may comprise one or more nucleic acid sequences; The said nucleic acid can be delivered into tumor cells and/or cancer cells and cause the tumor cells and/or cancer cells to express specific targets (e.g., antigenic epitope peptides or immunogens) that can be recognized by immune cells (e.g., the naturally occurring immune cells of the subject or adoptive transferred immune cells of the subject); said labelling polypeptides comprise an antigenic epitope peptide; in an aspect, the said labelling polypeptide may comprise multiple antigenic epitope peptides; in one aspect, the said MHC protein comprises a HLA class I protein; and (b) the second composition, the said second composition comprises a second active ingredient in a second druggable vehicle. The said the second active ingredient comprises immune cells purified from peripheral blood or from tumor tissue and are cultured in vitro (e.g., the subject's own T cells purified from peripheral blood or from tumor tissue of the subject and cultured in vitro); or TCR genetically modified immune cells (e.g., the subject's own immune cells with TCR receptor genetically modified using recombinant technology); Preferably, the second active ingredient contains TCR-modified T cells (e.g., the subject's own T cells with TCR receptor genetically modified using recombinant technology).

(2) According to the therapeutic agent described in (1), the said antigenic epitope peptide is originated from a protein present in nature, or an artificially synthesized amino acid sequence that does not exist in the nature; preferably, the said antigenic epitope peptide is derived from a protein present in nature including human-derived protein and the protein of other species except human.

(3) According to the therapeutic agent described in (1), the antigenic epitope peptide is derived from a tumor-associated antigen including the self-protein aberrantly expressed in tumor and/or cancer cells, or from a tumor-specific antigen including the mutant protein or peptide caused by genomic alteration or mutation of self-protein or peptide.

(4) According to the therapeutic agent described in (1), the said labelling polypeptide comprises an operably linked and tandem amino acid sequence (or short as operable and tandem amino acid sequence) as the following: a N-terminal signal peptide, one or more of the antigenic epitope peptides, and/or a C-terminal endoplasmic reticulum (ER) retention signal sequence. In an embodiment, when the labelling polypeptide comprises multiple antigenic epitope peptides, each of the two adjacent antigenic epitope peptides is connected by a self-cleaving linker peptide. Preferably, the N-terminal signal peptide is derived from Insulin-like peptide INSL5: 1-22 as shown in SEQ ID NO:1; Preferably, the self-cleaving linker peptide is a furin enzyme cleavage peptide Arg-X-[Lys/Arg]-Arg (X is any amino acid residue).

(5) According to the therapeutic agent described in (4), the said antigenic epitope peptide is originated from a tumor-associated antigen includes, but is not limited to, NY-ESO-1 157-165, NY-ESO-1 1-11, NY-ESO-1 53-62, NY-ESO-1 18-27, Her2/neu 369-377, SSX-2 41-49, MAGE-A4 230-239, MAGE-A10 254-262, MAGE-C2 336-344, MAGE-C2 191-200, MAGE-C2 307-315, MAGE-C2 42-50, MAGE-A1 120-129, MAGE-A1 230-238, MAGE-A1 161-169, KK-LC-1 76-84, p53 99-107, PRAME 301-309, Alpha fetoprotein 158-166, HPV16-E6 29-38, HPV16-E7 11-19, HPV16-E7 11-19, EBV-LMP1 51-59, and EBV-LMP1 125-133. In an aspect, the amino acid sequence of NY-ESO-1 157-165 is shown in SEQ ID NO: 2.

(6) According to the therapeutic agent described in (4), the said antigenic epitope peptide is derived from a tumor-specific antigen includes, but is not limited to, KRAS G12D 8-16, KRAS: G12D 7-16, KRAS:G12C 8-16, KRAS:G12A 8-16, KRAS: G12S 8-16, KRAS: G12R 8-16, KRAS: G12V 8-16, KRAS: G12V 7-16, KRAS: G12V 5-14, KRAS: G12V 11-19, KRAS: G12V 5-14, KRAS: Q61H 55-64, KRAS: Q61L 55-64, KRAS: Q61R 55-64, KRAS: G12D 5-14, KRAS: G1 3 D 5-14, KRAS: G12 A 5-14, KRAS: G12 C 5-14, KRAS: G12 S 5-14, KRAS: G12 R 5-14, KRAS: G12D 10-19, KRAS: G12D 10-18, TP53: V157G 156-164, TP53: R248Q 240-249, TP53: R248W 240-249, TP53: G245S 240-249, TP53: V157F 156-164, TP53: V157F 149-158, TP53: Y163C 156-164, TP53: R248Q 247-255, TP53: R248Q 245-254, TP53: R248W 245-254, TP53: G245S 245-254, TP53: G249S 245-254, TP53: Y22 0C 217-225, TP53: R175H 168-176, TP53: R248W 240-249, TP53: K132N 125-134, CDC73: Q254E 248-256, CYP2A6: N438Y 436-444, CTNNB1: T41A 41-49, CTNNB1: S45P 41-49, CTNNB1: T41A 34-43, CTNNB1:S37Y 30-39, CTNNB1:S33C 30-39, CTNNB1: S45P 40-49, EGFR: L858R 852-860, EGFR: T790M 790-799, PIK3CA: E542K 533-542, PIK3CA: H1047R 1046-1055, GNAS: R201H 197-205, CDK4:R24C 23-32, H3.3:K27M 26-35, BRAF: V600E591-601, CHD4: K73Rfs141-148, NRAS: Q61R 55-64, IDH1: R132H 126-135, TVP23C: C51Y:51-59, TVP23C: C51Y 42-51, and TVP23C: C51Y: 45-53. In an aspect, the amino acid sequence of KRAS: G12D 10-18 is shown in SEQ ID NO: 3.

(7) According to the therapeutic agent described in (1), the said nucleic acid encodes the labelling polypeptide, and the expression of the labelling polypeptide is controlled by an optional exogenous gene-expression regulatory element(s), or the druggable vehicle's own gene-expression regulatory element(s). The gene-expression regulatory elements include promoter(s), enhancer(s), silencer(s) and polyadenylation signal(s). Preferably, the nucleic acid encodes a labelling polypeptide and concurrently encodes an exogenous HLA protein that can present the said antigenic epitope peptide; the expression of HLA protein and the labelling polypeptide are under the control of separate promoters, or under the control of the same promoter while the HLA protein and the labelling polypeptide are operably connected by a self-cleaving linker peptide; Preferably, the self-cleaving linker peptide containing a furin enzyme cleavage peptide and a 2A peptide as shown in SEQ ID NO: 4.

(8) According to the therapeutic agent described in (1), the said nucleic acid encodes a human leukocyte antigen (HLA) protein, further specifically, the said HLA includes HLA-A, B, C. The expression of HLA protein is controlled by an optional exogenous gene-expression regulatory element(s), or the druggable vehicle's own gene-expression regulatory element(s). The gene-expression regulatory element(s) include promoter(s), enhancer(s), silencer(s) and polyadenylation signal(s).

(9) According to the therapeutic described in (7) and/or (8), the said nucleic acid encodes an exogenous HLA class I protein, including but not limited to a wild type HLA-A*02:01 protein as shown in SEQ ID NO: 5, and a mutant HLA-C*08:02 protein comprising E337V and I337T substitutions as shown in SEQ ID NO: 6; In an aspect, other HLA proteins encoded by the said nucleic acid include, but are not limited to, HLA-A*01:01 protein, HLA-A*02:03 protein, HLA-A*02:03 protein, HLA-A*03:01 protein, HLA-A*11:01 protein, HLA-A*24:02 protein, HLA-A*30:01 protein, HLA-A*68:01 protein, HLA-B*08:01 protein, HLA-B*14:02 protein, HLA-B*1501, HLA-B*58:01, HLA-C*07:01 protein, and HLA-C*01:02 protein. Preferably, the HLA-C, as shown in SEQ ID NO: 5 contains I337T point mutation, further preferably, the HLA-C contains I337T and E334V point mutations.

(10) According to the therapeutic agent described in (1), the said nucleic acid concurrently encodes an HLA protein and a beta-2 microglobulin protein. In an aspect, the beta-2 microglobulin is a human protein or a murine protein. Preferably, the expression of a HLA protein and a beta-2 microglobulin is controlled by the separate promoters, or under the control of the same promoter while the HLA protein and the beta-2 microglobulin are operably connected by a self-cleaving linker peptide, as shown in SEQ ID NO: 7 or in SEQ ID NO: 8.

(11) According to the therapeutic agent described in (1), the first composition and the second composition are present independently in the therapeutic agent and are not mixed with each other.

(12) According to the therapeutic agent described in (1), the said nucleic acid includes DNA or RNA; in an aspect, the said RNA comprises the messenger RNA (mRNA) that is transcribed by the said DNA.

(13) According to the therapeutic agent described in (1), the said first active ingredient is a recombinant virus, the genome of the recombinant virus comprises the said nucleic acid encoding the labelling polypeptide; In another aspect, the genome of the recombinant virus comprises the said nucleic acid encoding both the labelling polypeptide and a exogenous HLA protein; The recombinant viruses include a conditionally replication-competent virus or a replication-defective virus; preferably, the conditionally replication-competent virus is a oncolytic virus.

(14) According to the therapeutic agent described in (1), the said the first active ingredient is a recombinant virus, the genome of the recombinant virus comprises the said nucleic acid encoding an exogenous HLA protein; In another aspect, the genome of the recombinant virus comprises the said nucleic acid encoding both a HLA protein and a beta-2 microglobulin; The recombinant virus comprises a conditionally replication-competent virus or a replication-deficient virus; Preferably, the conditionally replication-competent virus is a oncolytic virus.

(15) According to the therapeutic agent described in (13) and/or (14), The said the replication-defective recombinant virus is derived from an adenovirus, an adeno-associated virus (AAV), a herpes simplex virus, a poxvirus, an influenza virus, an Alphavirus, or a murine respirovirus.

(16) According to the therapeutic agent described in (13), (14) and/or (15) the said the replication-defective recombinant virus is derived from a type 5 adenovirus; In an aspect, in the genome of the recombinant adenovirus, the E1 gene is deleted and replaced with the said the nucleic acid encoding a labelling polypeptide, or a labelling polypeptide and an exogenous HLA protein; In another aspect, the genome of the recombinant virus comprises the said nucleic acid encoding an exogenous HLA protein, or both a HLA protein and a beta-2 microglobulin; Preferably, the nucleic acid is controlled by optional exogenous gene-expression regulatory element(s), or the druggable vehicle's own gene-expression regulatory element(s).

(17) According to the therapeutic agent described in (13) and/or (14), the said conditionally replication-competent virus is a type of oncolytic virus that is derived from a wildtype or a recombinant virus with genetic mutations that allows it to acquire the capability to selectively replicate in tumor cells; Preferably, the oncolytic viruses include, but not limited to: adenovirus, poxviruses, herpes simplex virus, measles virus, Semliki forest virus, Indiana vesiculovirus, poliovirus, retrovirus, reovirus, senecavirus, Echovirus, coxsackievirus, Newcastle disease virus and Maraba virus.

(18) According to the therapeutic agent described in (13) and/or (14), the said oncolytic virus is derived from a type 5 adenovirus. Preferably, in the genome of the recombinant oncolytic adenovirus, the E1B-55K and E1B-19K genes are deleted while retaining the E1A gene as shown in SEQ ID NO: 34; In an aspect, the expression of E1A protein is controlled by optional exogenous gene-expression regulatory element(s), or the recombinant adenovirus' own gene-expression regulatory element(s); Preferably, the E1A protein is the type 5 adenovirus E1A-32 kDa protein as shown in SEQ ID NO: 9.

(19) According to the therapeutic agent described in (13), (14) and/or (18), at the region of the deleted E1B-55K and E1B-19K genes, the oncolytic adenovirus contains the said nucleic acid encoding a labelling polypeptide, or both the labelling polypeptide and an exogenous HLA protein; In another aspect, the genome of the recombinant virus contains the said nucleic acid encoding an exogenous HLA protein, or both an exogenous HLA protein and a beta-2 microglobulin; in an aspect, the nucleic acid is controlled by the optional exogenous gene-expression regulatory element(s), or the oncolytic adenovirus's own gene-expression regulatory element(s); preferably, the expression of said nucleic acid encoding peptide or protein is controlled by a native E1B promoter (including E1B TATA box sequence) and a Kozak sequence as shown in SEQ ID NO: 10, and by a native E1B polyadenylation signal sequence.

(20) According to the therapeutic agents described in (18) and/or (19), the said recombinant oncolytic adenovirus comprises E1A gene with mutation(s), where the mutant E1A protein cannot bind to pRb protein and STING protein; Preferably, the E1A protein contains a 24-base pair deletion (E1A 122-129) as shown in SEQ ID NO: 11, or the mutant E1A protein contains point mutations L122V, C124S and E126D as shown in SEQ ID NO: 12.

(21) According to the therapeutic agent described in (16) and/or (18), in the genome of the recombinant adenovirus, the E3 gene region is fully or partially deleted.

(22) According to the therapeutic agent described in (1) to (21), the said immune cells can specifically recognize the said antigenic epitope peptide that is presented by the said exogenous HLA protein; Preferably, the immune cells include native T cells or their precursor cells, activated T cells, NKT cells, or T cell lines.

(23) According to the therapeutic agent described in (1) to (22), the said first composition contains therapeutically effective dose of the DNA, or RNA.

(24) According to the therapeutic agent described in (13) and/or (14), the said first composition contains the therapeutically effective dose of the recombinant virus.

(26) According to the therapeutic agent described in (1), the second composition comprises the therapeutically effective dose of immune cells. Preferably, the second composition comprises the therapeutically effective dose of TCR genetically modified immune cells.

(26) According to the therapeutic agent described in (12), the said DNA or RNA is formulated and administered intratumorally;

(27) According to the therapeutic agent described in (14) and (15), the said the recombinant virus is formulated and administered intratumorally, intra-peritoneally, intrathecally or intravenously.

(28) According to the therapeutic agent described in (1), the said immune cells are formulated and administered through the routes as following: the intraarterial, intravenous, subcutaneous, intracutaneous, intratumoral, intra-lymphatic, intrathecal, intracerebrospinal, intra-bone marrow, intra-muscular or intra-peritoneal administration.

(29) According to the therapeutic agent described in (1), the said therapeutic agent contains the first composition and the second composition.

(30) The said application is the application of any one of the therapeutic agents described in (1)-(29) in the administration/preparation/manufacturing of drugs for the treatment of tumors and/or cancers.

(31) According to the application described in (30), the tumors and/or cancers described include, but not limited to: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, pheochromocytoma, prolactinoma, von Hippel-Lindau disease, Zollinger-Ellison syndrome, anal cancer, cholangiocarcinoma, bladder cancer, urethral cancer, glioma, neuroblastoma, meningioma, spinal cord tumor, Bone tumor, chondrosarcoma, Ewing's sarcoma, cancer of unknown primary site, carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, cardiac sarcoma, meningeal carcinomatosis, primary peritoneal carcinoma and malignant pleural mesothelioma.

(32) According to the labelling polypeptide described in (31), the labelling polypeptide comprises an operable and tandem amino acid sequence as the following: a N-terminal signal peptide, one or more of the antigenic epitope peptides, and/or a C-terminal endoplasmic reticulum (ER) retention signal sequence. In an aspect, when the labelling polypeptide comprises multiple antigenic epitope peptides, each of the two adjacent antigenic epitope peptides is connected by a self-cleaving linker peptide.

(33) According to the labelling polypeptide described in (32), the said antigenic epitope peptide is derived from tumor-associated antigens includes, but is not limited to, NY-ESO-1 157-165, Her2/neu 369-377, NY-ESO-1 1-11, NY-ESO-1 53-62, NY-ESO-1 18-27, SSX-2 41-49, MAGE-A4 230-239, MAGE-A10 254-262, MAGE-C2 336-344, MAGE-C2 191-200, MAGE-C2 307-315, MAGE-C2 42-50, MAGE-A1 120-129, MAGE-A1 230-238, MAGE-A1 161-169, KK-LC-1 76-84, p53 99-107, PRAME 301-309, Alpha fetoprotein 158-166, HPV16-E6 29-38, HPV16-E7 11-19, HPV16-E7 11-19, EBV-LMP1 51-59, EBV-LMP1 125-133, KRAS: G12D 8-16, KRAS: G12D 7-16, KRAS: G12C 8-16, KRAS:G12A 8-16, KRAS: G12S 8-16, KRAS: G12R 8-16, KRAS: G12R 8-16, KRAS: G: G: G: G 12V 8-16, KRAS: G12V 7-16, KRAS: G12V 5-14, KRAS: G12V 11-19, KRAS: G12V 5-14, KRAS: Q61H 55-64, KRAS: Q61L 55-64, KRAS: Q61L 55-64, KRAS: Q66 1R 55-64, KRAS: G12D 5-14, KRAS: G13D 5-14, KRAS: G12A 5-14, KRAS: G12C 5-14, KRAS: G12S 5-14, KRAS: G12R 5-14, KRAS: G12D 10-19, KRAS S: G12D 10-18, TP53: V157G 156-164, TP53: R248Q 240-249, TP53: R248W 240-249, TP53: G245S 240-249, TP53: V157F 1566F-164, TP53: V157F 149-158, TP53: Y163C 156-164, TP53: R248Q 247-255, TP53: R248Q 245-254, TP53: R248W 245-254, TP53: T53: G244S-254 54, TP53: G249S 245-254, TP53: Y240C 217-225, TP53: R175H 168-176, TP53: R248W 240-249, TP53: K132N 125-134, CDC73: Q25E24-25 6, CYP2A6: N438Y 436-444, CTNNB1: T41A 41-49, CTNNB1: S45P 41-49, CTNNB1: T41A 34-43, CTNNB1: S37Y 30-39, CTNNB1: S3C 30-39, CTNNB1: S3C 30-39, CTNNB1: S45P 40-49, EGFR: L858R 852-860, EGFR: T790M 790-799, PIK3CA: E542K 533-542, PIK3CA: H1047R 1046-1055, GNAS: R201H 197-255, CDK4:R24C 23-32, H3.3: K27M 26-35, BRAF: V600E 591-601, CHD4 K73 Rfs 141-148, NRAS Q61R 55-64, IDH1:R132H 126-135, TVP23C: C51Y 42-51, or TVP23C: C51Y: 45-53.

(34) According to the labelling polypeptide described in (32), the said amino acid sequence of the labelling polypeptide has at least 98% as shown in SEQ ID NO: 13 or SEQ ID NO:14; Preferably, the amino acid sequence of the labelling polypeptide is as shown in SEQ ID NO: 13 or SEQ ID NO:14.

(35) A separated nucleic acid encoding the labelling polypeptide described in any one of (33)-(34).

(36) According to the nucleic acid described in (35), the nucleic acid encodes a labelling polypeptide and concurrently encodes a exogenous HLA protein that can present the said antigenic epitope peptide; the expression of HLA protein and the labelling polypeptide are under the control of the separate promoters, or under the control of the same promoter while the HLA protein and the labelling polypeptide are operably connected by a self-cleaving linker peptide.

(37) According to the nucleic acid described in (35), the nucleic acid encodes an exogenous HLA Class I protein; In an aspect, the HLA Class I protein includes HLA-A, B, C.

(38) According to the HLA Class I protein described in (37), the said nucleic acid encodes an exogenous HLA class I protein, including a wild type HLA-A*02:01 protein as shown in SEQ ID NO: 5, or a mutant HLA-C*08:02 protein comprising the E337V and I337T substitutions as shown in SEQ ID NO: 6; The other HLA proteins encoded by the said nucleic acid include, but are not limited to, HLA-A*01:01 protein, HLA-A*02:03 protein, HLA-A*02:03 protein, HLA-A*03:01 protein, HLA-A*11:01 protein, HLA-A*24:02 protein, HLA-A*30:01 protein, HLA-A*68:01 protein, HLA-B*08:01 protein, HLA-B*14:02 protein, HLA-B*1501, HLA-B*58:01, HLA-C*07:01 protein, HLA-C*01:02 protein. Preferably, the HLA-C, as shown in SEQ ID NO: 6 contains the I337T point mutation, further preferably, the HLA-C contains the I337T and E334V point mutations.

(39) A separated nucleic acid encoding any one of the HLA class I protein described in (37) and (38).

(40) According to the nucleic acid described in (39), the said nucleic acid concurrently encodes a HLA protein and a beta-2 microglobulin protein. In an aspect, the beta-2 microglobulin is a human protein or a murine protein. Preferably, the expression of a HLA protein and a beta-2 microglobulin is controlled by the separate promoters, or under the control of the same promoter while the HLA protein and the beta-2 microglobulin are operably connected by a self-cleaving linker peptide; Preferably, the nucleic acid encodes a HLA-A*2-01 protein and a beta-2 microgloglulin as shown in SEQ ID NO: 7, or a HLA-C*08:02 proteins and a beta-2 microglobulin as shown in SEQ ID NO: 8.

(41) According to the nucleic acid described in (35) and/or (39), the said nucleic acid includes DNA or RNA; the said RNA comprises messenger RNA (mRNA) that is transcribed by the said DNA.

(42) According to the nucleic acid described in (41), the said nucleic acid is DNA, its nucleotide sequence is shown in SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 or SEQ ID NO: 23.

(43) A separated recombinant druggable vehicle comprises the nucleic acid described in any one of the nucleotide sequences described in any one of (32)-(42) and/or its complementary sequence.

(44) A separated recombinant virus comprises the nucleic acid described in any one of the nucleotide sequences described in any one of (32)-(42); The recombinant virus includes a conditionally replication-competent virus or a replication-deficient virus, preferably, the conditionally replication-competent virus is an oncolytic virus.

(45) According to the recombinant virus described in (44), the said the replication-defective recombinant virus is derived from an adenovirus, an adeno-associated virus (AAV), a herpes simplex virus, a poxvirus, an influenza virus, an Alphavirus, or a murine respirovirus.

(46) According to the recombinant virus described in (45), the said replication-defective recombinant virus is derived from a type 5 adenovirus; In an aspect, in the genome of the recombinant adenovirus, the E1 gene is deleted and replaced with the said nucleic acid encoding a labelling polypeptide, or a labelling polypeptide and an exogenous HLA protein; In another aspect, the genome of the recombinant virus comprises the said nucleic acid encoding an exogenous HLA protein, or both a HLA protein and a beta-2 microglobulin; Preferably, the nucleic acid is controlled by the optional exogenous gene-expression regulatory elements, or the druggable vehicle's own gene-expression regulatory elements.

(47) According to the recombinant virus described in (44), the said conditionally replication-competent virus is a type of oncolytic virus that is originated from a wildtype or a recombinant virus with genetic mutations that acquires the capability to selectively replicate in tumor cells; Preferably, the oncolytic viruses include, but not limited to: adenovirus, poxviruses, herpes simplex virus, measles virus, Semliki forest virus, Indiana vesiculovirus, poliovirus, retrovirus, reovirus, senecavirus, Echovirus, coxsackievirus, Newcastle disease virus or Maraba virus.

(48) According to the recombinant virus described in (44), the said oncolytic virus is originated from type 5 adenovirus. Preferably, in the genome of the recombinant oncolytic adenovirus, the E1B-55K and E1B-19K genes are deleted while retaining E1A gene; the expression of E1A protein is controlled by the optional exogenous gene-expression regulatory elements, or the recombinant adenovirus' own gene-expression regulatory elements. Preferably, the E1A protein is the type 5 adenovirus E1A-32 kDa protein as shown in SEQ ID NO: 9.

(49) According to the recombinant virus described in (49), at the region of the deleted E1B-55K and E1B-19K genes, the oncolytic adenovirus contains the said nucleic acid encoding the labelling polypeptide, or both the labelling polypeptide and an exogenous HLA protein; In another aspect, the genome of the recombinant virus contains the said nucleic acid encoding an exogenous HLA protein, or both an exogenous HLA protein and a beta-2 microglobulin; In an aspect, the nucleic acid is controlled by the optional exogenous gene-expression regulatory elements, or the druggable vehicle's own gene-expression regulatory elements; Preferably, the expression of said nucleic acid encoding peptide or protein is controlled by a native E1B promoter (including E1B TATA box sequence and Kozak sequence) as shown in SEQ ID NO: 10, and by a native E1B polyadenylation signal sequences.

(50) According to the recombinant virus described in (44) and/or (49), the said recombinant oncolytic adenovirus comprises a E1A gene with mutations, where the mutant E1A protein cannot bind to pRb protein and STING protein; Preferably, the E1A protein contains a 24-base pair deletion (E1A 122-129 deletion) as shown in SEQ ID NO: 11, or the mutant E1A protein contains the point mutations at L122V, C124S and E126D as shown in SEQ ID NO: 12.

(51) According to the recombinant virus described in (46) and/or (48), in the said the genome of the recombinant adenovirus, the E3 gene region is fully or partially deleted.

(52) A drug combination for the treatment of tumors and/or cancers, including:
The first vehicle, the first vehicle comprises the first composition in any of the therapeutic agents described in any one of (1)-(30);
The second vehicle, the second vehicle comprises the first composition in any of the therapeutic agents described in (1)-(30);
The first vehicle and the second vehicle are separated; and a manual of the timing and manner of drug administering is provided.

(53) The application of the nucleic acid described in any one of (35)-(42) to prepare or manufacture drugs for the treatment or prevention of tumors and/or cancers.

(54) The application of the recombinant druggable vehicle described in (43) to prepare or manufacture drugs for the treatment or prevention of tumors and/or cancers.

(55) The application of the recombinant virus described in any one of (44)-(51) to prepare or manufacture drugs for the treatment or prevention of tumors and/or cancers.

(56) The application of the drug combination described in (52) to prepare or manufacture drugs for the treatment or prevention of tumors and/or cancers.

(57) According to the application described in any of (53)-(56), the said tumors and/or cancers are any applicable tumors and/or cancers, include but not limited to: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, pheochromocytoma, prolactinoma, von Hippel-Lindau disease, Zollinger-Ellison syndrome, anal cancer, cholangiocarcinoma, bladder cancer, urethral cancer, glioma, neuroblastoma, meningioma, spinal cord tumor, bone tumor, chondrosarcoma, Ewing's sarcoma, cancer of unknown primary site, carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, cardiac sarcoma, meningeal carcinomatosis, primary peritoneal carcinoma or malignant pleural mesothelioma.

(58) A method to treat tumors and/or cancers, including:
Treat the tumor and/or cancer patients with the first composition in any of the therapeutic agents described in (1), (2), (3), (4), (5), (6), (7), (12), (13), (14), (16), (17), (18), (19), (20), (21), (22), (23), (24), (25), (26), (27), (28), (29); and,
Treat the tumor and/or cancer patients with the second composition in any of the therapeutic agents described in (1)-(30).

(59) A method to treat a tumor and/or cancer patient, including:
Treat the tumor and/or cancer patients with the first composition in any of the therapeutic agents described in (1), (8), (9), (10), (11), (12), (13), (15), (16), (17), (18), (19), (20), (21), (22), (23), (23), (24), (25), (26), (27), (28), (29); Preferably, the tumor cells and/or cancer cells express the tumor antigens, including and not limited to, NY-ESO-1, Her2/neu, SSX-2, MAGE-C2, MAGE-A1, M-2433-233, MAGE-A10 254-262, KK-LC-1, p53, PRAME, Alpha fetoprotein, HPV6-E6, HPV16-E7, EBV-LMP1, KRAS: G12D, KRAS: G12C, KRAS: G12A, KRAS: G12S, KRAS: G12R, KRAS: G12R, KRAS: G12R, KRAS: G122 V, KRAS: Q61H, KRAS: Q61L, KRAS: Q61R, KRAS: G13D, TP53: V157G, TP53: V157F, TP53: R248Q, TP53: R248W, TP53: G245S, TP53: Y163C, TP53: G249S, TP53: Y240C, TP53: R175H, TP53: K132N, CDC73: Q254E, TPP2A6: N438Y, CTNN1: T41A, CTNNB1: S45P, CTNNB1: S37Y, CTNNB1: S33C, EGFR: L858R, EGFR: T790M, PIK3CA: E542K, PIK3CA: H1047R, GNAS: R201H, CDK4:R24, R24C H3. 3:K28M, BRAF: V600E, CHD4 K73Rfs, NRAS Q61R, IDH1:R132H, or TVP23C: C51Y; and, treat the tumor and/or cancer patients with the second composition in any of the therapeutic agents described in (1)-(30).

(60) Preferably, according to the methods described in (58) and/or (59), the drug administering is applied successively as the following steps:
  a) administer the first composition in the said therapeutic agent to the tumor and/or cancer patient;
  b) After applying the first composition, administer the second composition in the said therapeutic agent to the tumor and/or cancer patient.

(61) According to the method described in (58) and/or (59), the said tumors and/or cancers include but not limited: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, Pheochromocytoma, Prolactinoma, von Hippel-Lindau disease, Zollinger-Ellison syndrome, anal cancer, Cholangiocarcinoma, bladder cancer, urethral cancer, glioma, neuroblastoma, meningioma, spinal cord tumor, Bone tumor, chondrosarcoma, Ewing's sarcoma, cancer of unknown primary site, Carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, Multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, Cardiac Sarcoma, Meningeal carcinomatosis, primary peritoneal carcinoma or malignant pleural mesothelioma.

Compared to the existing technology, the present invention has the following advantages and positive effects:

The invention can not only improve the anti-tumor function of the adoptive transferred T cells, including the TCR genetically modified T cells, but also expand the application scope of the adoptive T-cell therapy against tumors and/or cancers. The present invention help to resolve the major problems that challenge the adoptive T cell therapy, such as uneven expression of tumor antigens that is caused by tumor heterogeneity or the aberrant processing and presenting of tumor antigenic peptides by MHC molecules due to the deficient antigen presenting machinery in tumor cells. More importantly, the invention can circumvent the MHC restriction and expand the scope of application of adoptive T cell therapy to the patients who harbor a tumor antigen but do not have the HLA allele that is required to present the antigenic epitope peptide derived from the tumor antigen.

Specifically, the present invention designs a nucleic acid encoding an artificial peptide (the said labelling polypeptide) comprising one or more antigenic epitope peptides derived from a tumor antigen. Delivering the said nucleic acid into tumor cells can increase the presentation of the tumor antigenic peptide/MHC complexes on the surface of tumor cells, which enhances the recognition sensitivity of the adoptively transferred tumor antigen-specific T cells. The invention also discloses a nucleic acid encoding an exogenous HLA protein. Expression of the exogenous HLA protein in tumor cells not only solves the problem of low or deficient expression of endogenous HLA, but also enables the tumor antigenic epitope which cannot be presented by the endogenous HLA Class I molecule to be presented by the exogenous HLA. Subsequently, the tumor cells presenting the tumor antigenic epitope in the context of exogenous HLA can be recognized and killed by the adoptively transferred T cells that can recognize the tumor antigen in the context of the exogenous HLA. Moreover, because of the absence of tumor antigen in the normal cells, adoptively transferred T cells will not target normal cells even in case the nucleic acid encoding exogenous HLA protein is delivered into normal cells, which augments the safety of adoptive T cell therapy.

In addition, the present invention uses oncolytic virus as a vector to deliver the nucleic acid encoding the labelling polypeptide or the exogenous HLA protein into tumor cells. the anti-tumor function of the adoptive T cells can be enhanced not only by the elevating presentation of the specific antigenic peptide/MHC complexes on tumor cells, but also by the relief of immunosuppression in tumor microenvironment due to the infection of viruses. On the other hand, when the oncolytic virus is not able to complete replication cycles and produce sufficient number of progeny virus to lyse tumor cells, the adoptively transferred T cells can eliminate those tumor cells and release tumor antigens to further activate endogenous anti-tumor immunity. Therefore, combination adoptive T cell therapy and oncolytic virus will achieve a synergistic anti-tumor effect.

The present invention provides a novel approach to treat cancers and/or tumors.

38)) is flanked with the 5' native E1B promoter (E1B pro) and 3' pIX gene region including a native E1B/IX poly A signal sequence (E1B/IX pA). In an aspect, the E1B gene region is deleted.

Figure 1A:
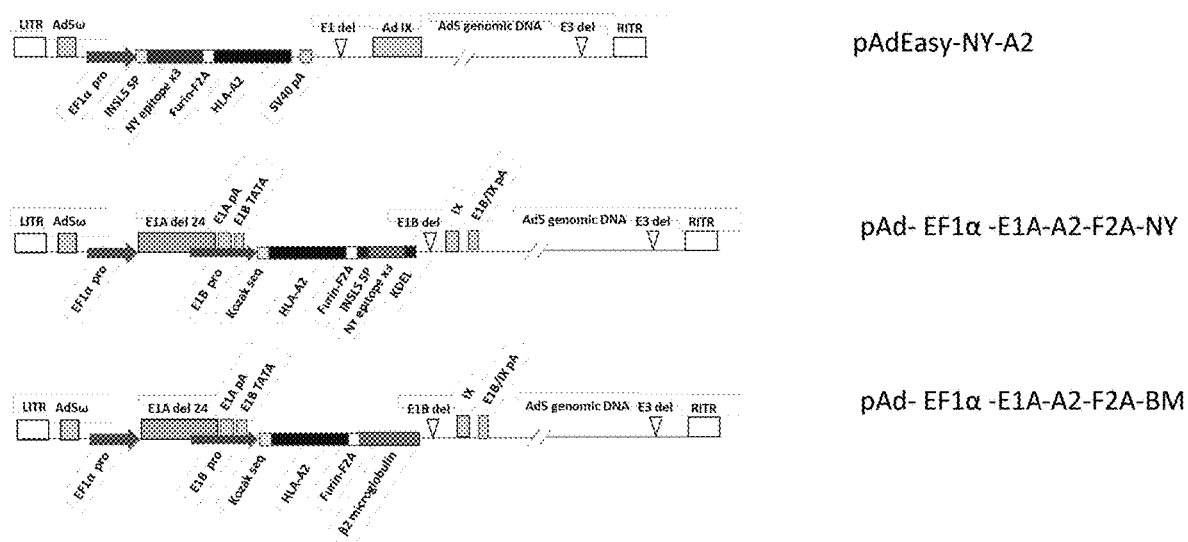
FIG. 1A shows the schematic representations of the recombinant adenovirus constructs described herein. pAdEasy-EF1 α-NY-A2 represents the replication-defective adenovirus vector that expresses the said labelling polypeptide containing NY-ESO-1 157-165 epitope peptide and the HLA-A2 protein. The backbone of the construct is derived from genomic DNA of type 5 adenovirus with deletions of E1 region (E1 del) and E3 region (E3 del). In the E1A region, an expression unit is incorporated. The expression unit comprises a labelling polypeptide encoding sequence including a INSL5 signal peptide (INSL5 SP), three NY-ESO-1 157-165 epitope peptide connected with furin cleavage site (NY epitope x3), a linker peptide (Furin-F2A) and a HLA-A2 protein, the expression unit is flanked with a EF1 α promoter (EF1 α pro) and a SV40 poly (A) signal sequence (SV40 pA). LITR and RITR represent left end inverted terminal repeats (ITRs) and right end inverted terminal repeats respectively. pAd-EF1α-E1Ad24-A2-F2A-NY and pAd-EF1α-E1Ad24-A2-F2A-BM represent the conditionally replication-competent adenovirus vector that contains an HLA-A2 gene with a nucleic acid encoding the said labelling polypeptide containing NY-ESO-1 157-165 epitope peptide, or with a human beta-2 microglobulin gene. The backbone of these constructs are the genomic DNA of type 5 adenovirus with deletions of E1 and E3 regions. At the E1A region, a mutant E1A gene with 122-129 deletion (E1A de124) is incorporated into and flanked with an EF1 α promoter and a native E1A poly A signal (E1A pA). A expression unit encoding a HLA-A2 and a labelling polypeptide with a ER retaining signal (KDEL (SEQ ID NO.
Figure 1B:
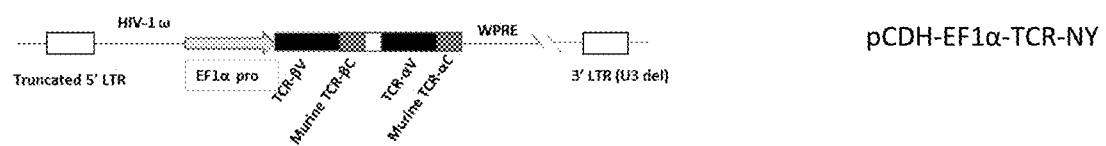

FIG. 1B shows the schematic representation of a lentiviral vector for the expression of TCR. pCDH-EF1α-TCR-NY represents a HIV-based lentivector that expresses TCR specific to NY-ESO-1 157-165 epitope peptide. A deletion in the enhancer of the U3 region (U3 del) ensures self-inactivation of the lentiviral construct. A TCR gene encoding a beta chain with the variable sequence (TCR-βV) and a murine constant sequence (Murine TCR-βC) and an alpha chain with the variable sequence (TCR-αV) and a murine constant sequence (Murine TCR-αC) is flanked with an EF1 α promoter and WPRE region.

Figure 1C:
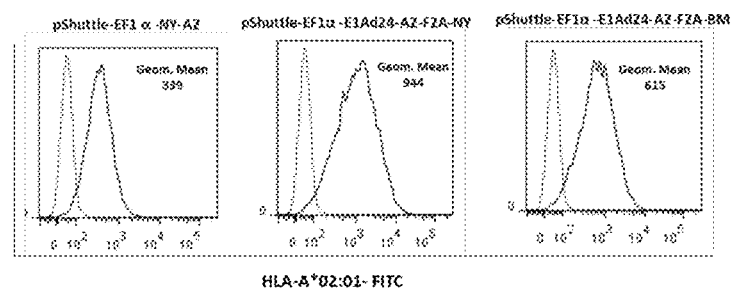

FIG. 1C shows the HLA-A2 expression by 293T cells after transfected with pShuttle vectors that expresses the said labelling polypeptide containing NY-ESO-1 157-165 epitope peptide and the HLA-A2 protein. 293T cells were stained with anti-HLA-A2 antibody labeled with FITC and analyzed with flow cytometry. The bold line shows the expression of HLA-A2 on 293T cells that are transduced with the vector encoding HLA-A2 protein. The gray line is the control 293T cells that were transduced with an empty vector. The mean fluorescence intensity (Geom Mean) of the gated population is shown on the flow cytometry graphs. The left graph shows the expression of HLA-A2 by 293T cells transduced with pShuttle-EF1 α-NY-A2, the middle graph shows the expression of HLA-A2 by 293T cells transduced with pShuttle-EF1α-E1Ad24-A2-F2A-NY and the right graph shows the expression of HLA-A2 by 293T cells transduced with pShuttle-EF1α-E1 Ad24-A2-F2A-BM.

Figure 1D:
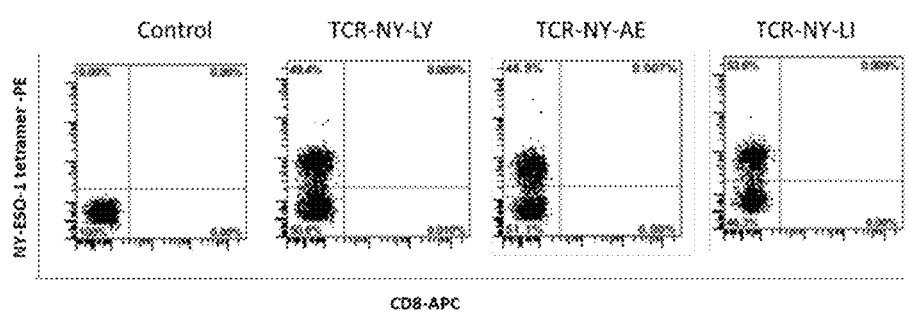

FIG. 1D shows the expression of NY-ESO-1 specific TCR by JRT cells after transfected with the lentivirus that express different TCRs specific to NY-ESO-1 157-165 epitope peptide in the context of HLA-A2. The JRT cells were transfected the recombinant lentivirus and analyzed in 7-10 days. JRT cells were stained with anti-CD8 antibody labelled with APC and the NY-ESO-1 157-165/HLA-A2 tetramer labelled with PE and analyzed by flow cytometry. The percentage of tetramer positive cells in the gated JRT cell population is shown on the flow cytometry graphs. The control group is the JRT cells that were not transduced with lentivirus; The 'TCR-NY-LY' group is the JRT cells transfected with the lentivirus generated from pCDH-EF1α-TCR-NY-LY; The 'TCR-NY-AE' group is the JRT cells transfected with the lentivirus generated from pCDH-EF1α-TCR-NY-AE and 'TCR-NY-L1' group is the JRT cells transfected with the lentivirus generated from pCDH-EF1α-TCR-NY-LI.

Figure 2A:
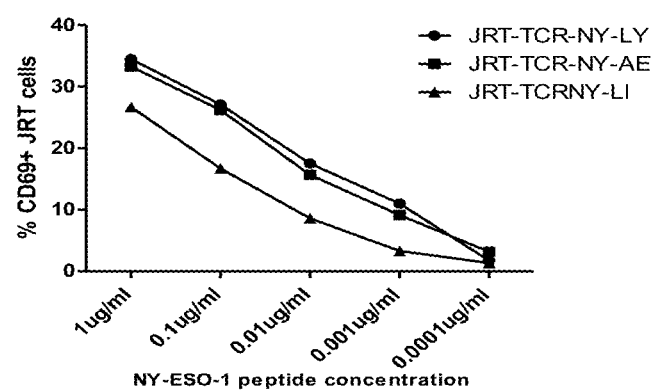

FIG. 2A shows the NY-ESO-1 specific TCRs can recognize NY-ESO-1 157-165 epitope peptide presented by HLA-A2 on T2 cells. JRT cells transduced with the recombinant lentivirus that were generated from pCDH-EF1α-TCR-NY-LY(JRT-TCR-NY-LY), pCDH-EF1α-TCR-NY-AE (JRT-TCR-NY-AE) or pCDH-EF1α-TCR-NY-LI (JRT-TCR-NY-LI) were cultured with T2 cells pulsed with 10× dilution series of NY-ESO-1 157-165 peptide starting from 1 ug/ml for 16 hours. The cells were harvested and stained with anti-CD69 antibodies to analyze the expression of CD69 by flow cytometry. X-axis is the target T2 cells pulsed with a series concentration of NY-ESO-1 157-165 peptide, Y-axis is the percentage of CD69+ cells in the gated JRT cells.

Figure 2B:
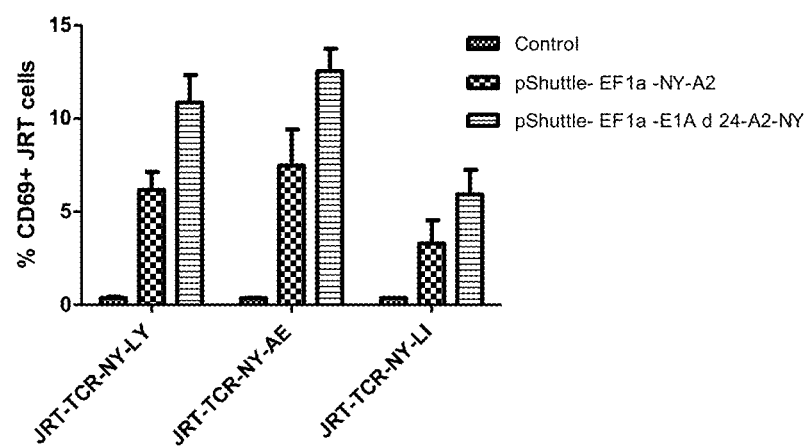

FIG. 2B shows that 293T cells expressing the labelling polypeptide containing NY-ESO-1 157-165 epitope peptide and HLA-A2 can activate the NY-ESO-1 specific TCRs on JRT cells. In the duplicated wells, JRT cells transduced with the recombinant lentivirus to express different TCRs specific to NY-ESO-1 were incubated with 293T cells transduced with either pShuttle-EF1a-NY-A2 or pShuttle-EF1a-E1A d 24-A2-NY for 16 hours, the cells were harvested and stained with anti-CD69 antibody to analyze the expression of CD69 by flow cytometry. X-axis shows JRT cells expressing different TCRs specific to NY-ESO-1, including JRT-TCR-NY-LY, JRT-TCR-NY-AE and JRT-TCR-NY-LI. Y-axis is the percentage of CD69+ cells in the gated JRT cells (mean±SD; n=2). The 'Control' bar represents the target 293T cells transduced with an empty pShuttle vector; 'pShuttle-EF1a-NY-A2' bar represents the target 293T cells transduced with pShuttle-EF1α-NY-A2 vector; 'pShuttle-EF1a-E1 Ad24-A2-NY' bar represents the target 293T cells transduced with pShuttle-EF1α-E1Ad24-A2-NY vector. The data was analyzed with Student's t test and ** represents $p<0.01$, * represents $p<0.05$.

Figure 2C:
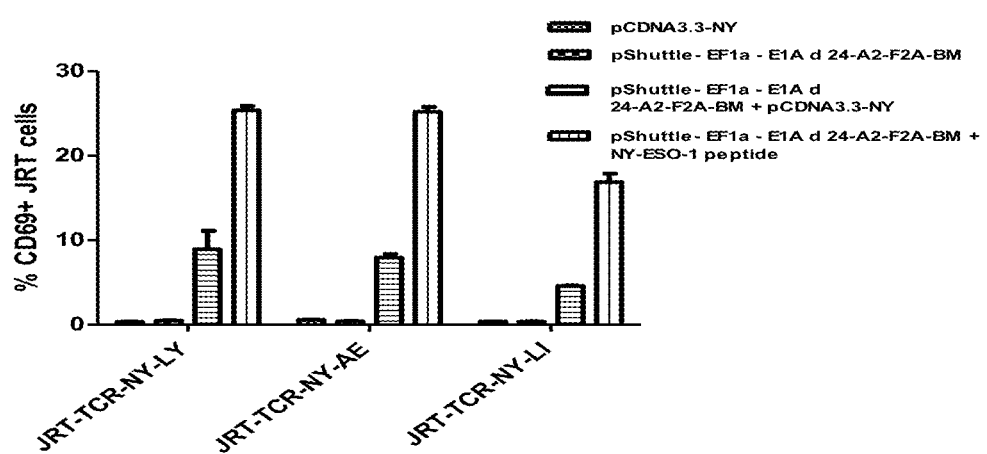

FIG. 2C shows that the exogenous HLA-A2 can present the NY-ESO-1 157-165 epitope peptide originated from NY-ESO-1 protein to activate the NY-ESO-1 specific TCRs on JRT cells. In duplicated wells, 293T cells were co-transfected with the pCDNA3.3 vector expressing full-length NY-ESO-1 protein (pCDNA3.3-NY) and the pshuttle vector expressing exogenous HLA-A2 protein (pShuttle-EF1-E1Ad24-A2-F2A-BM) were utilized as target cells to stimulate the JRT cells transduced with NY-ESO-1 specific TCRs. 293T cells transduced with pCDNA3.3-NY or pShuttle-EF1-E1Ad24-A2-F2A-BM alone as the negative control. 293T cells transduced with pShuttle-EF1-E1Ad24-A2-F2A-BM alone and pulsed with NY-ESO-1 157-165 epitope peptide at 1 ug/ml as the positive control. The cells were harvested in 16 hours, stained with anti-CD69 antibody and analyzed by flow cytometry. X-axis shows JRT cells expressing different TCRs specific to NY-ESO-1, including JRT-TCR-NY-LY, JRT-TCR-NY-AE and JRT-TCR-NY-LI. Y-axis is the percentage of CD69+ cells in the gated JRT cells (mean±SD; n=2). The 'pCDNA3.3-NY' bar represents the target 293T cells transduced with pCDNA3.3-NY alone; 'pShuttle-EF1a-E1A d 24-A2-F2A-BM' bar represents the target 293T cells transduced with pShuttle-EF1a-E1A d 24-A2-F2A-BM alone; 'pShuttle-EF1a-E1A d 24-A2-F2A-BM+pCDNA3.3-NY' bar represents the target 293T cells co-transduced with pShuttle-EF1a-E1A d 24-A2-F2A-BM and pCDNA3.3-NY; 'pShuttle-EF1a-E1A d 24-A2-F2A-BM+NY-ESO-1 peptide' represents the target 293T cells transduced with pShuttle-EF1a-E1A d 24-A2-F2A-BM and pulsed with NY-ESO-1 157-165 peptide. The data was analyzed with Student's t test and ** represents $p<0.01$, * represents $p<0.05$.

Figure 2D:
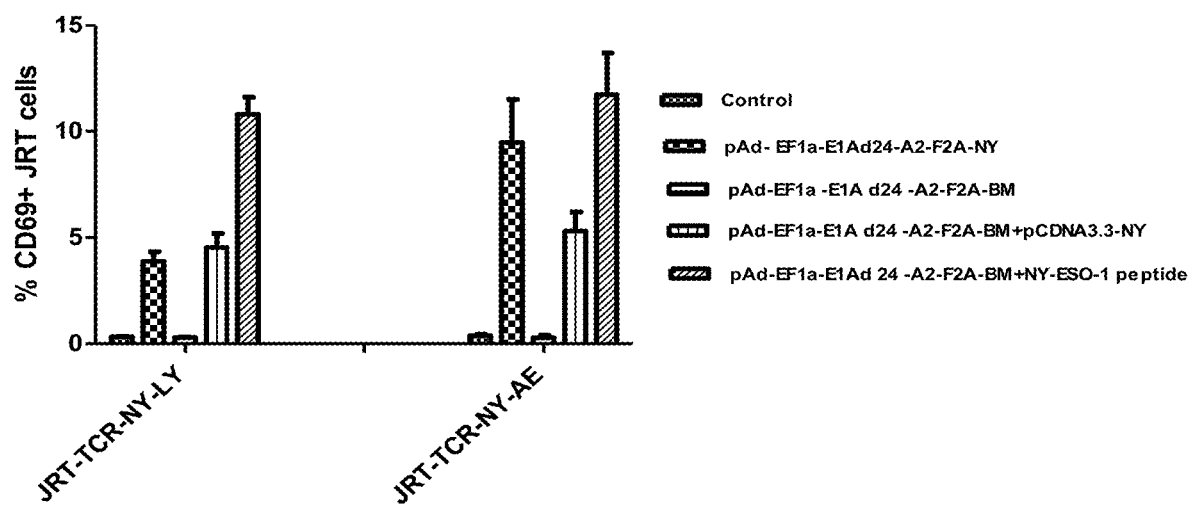

FIG. 2D shows that the nucleic acid encoding exogenous peptides and proteins in the recombinant adenovirus DNA can transduce 293T cells to express the labelling polypeptide containing NY-ESO-1 157-165 epitope peptide and exogenous HLA-A2. 293T cells were transduced with the recombinant adenovirus vector pAd-EF1a-E1A d 24-A2-NY and pAd-EF1a-E1A d 24-A2-BM and utilized as target cells to stimulate JRT cells expressing NY-ESO-1 specific TCRs. In duplicated wells, the mixed-culture cells were incubated for 16 hours and harvested to analyze the expression of CD69 by flow cytometry. X-axis shows JRT cells expressing different TCRs specific to NY-ESO-1, including JRT-TCR-NY-LY and JRT-TCR-NY-AE. Y-axis is the percentage of CD69+ cells in the gated JRT cells (mean±SD; n=2). The 'control' bar is 293T cells without transfection; 'pAd-EF1a-E1Ad24-A2-F2A-NY' and 'pAd-EF1a-E1A d24-A2-F2A-BM' bars represent the target 293T cells transduced with pAd-EF1a-E1Ad24-A2-F2A-NY or pAd-EF1a-E1A d24-

A2-F2A-BM respectively. 'pAd-EF1a-E1A d 24-A2-F2A-BM+pCDNA3.3-NY' bar represents the target 293T cells co-transduced with pAd-EF1a-E1A d 24-A2-F2A-BM and pCDNA3.3-NY; 'pAd-EF1a-E1A d 24-A2-F2A-BM+NY-ESO-1 peptide' represents the target 293T cells transduced with pAd-EF1a-E1A d 24-A2-F2A-BM and pulsed with NY-ESO-1 157-165 peptide. The data was analyzed with Student's t test and ** represents p<0.01, * represents p<0.05.

Figure 3:
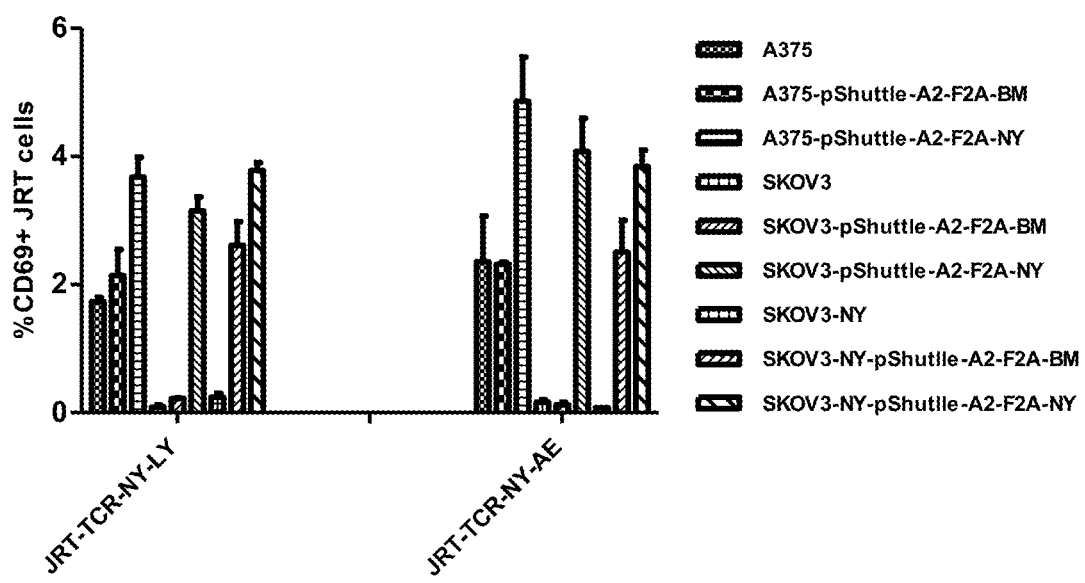

FIG. 3 shows that tumor cells can be sensitized by the labelling polypeptide containing NY-ESO-1 epitope peptides and exogenous HLA-A2 to be recognized by the NY-ESO-1 specific TCRs on JRT cells. Tumor cell lines A375, SKOV3 and SKOV3-NY (SKOV3 cells that were transduced with pCDNA3.3-NY and selected to stably express NY-ESO-1 protein) were transduced with pShuttle-A2-F2A-NY or pShuttle-A2-F2A-BM and utilized as target cells to stimulate JRT cells expressing NY-ESO-1 specific TCRs. In duplicated wells, tumor cells and JRT cells were mixed-culture for 16 hours, the cells harvested to analyze the expression of CD69 by flow cytometry. X-axis shows JRT cells expressing different TCRs specific to NY-ESO-1, including JRT-TCR-NY-LY and JRT-TCR-NY-AE. Y-axis is the percentage of CD69+ cells in the gated JRT cells (mean±SD; n=2). The 'A375', SKOV3' and SKOV3-NY' bars represent the target cells that were not transduced; the 'A375-pShuttle-A2-F2A-BM', SKOV3-pShuttle-A2-F2A-BM' and SKOV3-NY-pShuttle-A2-F2A-BM' bars represent the target tumor cells that were transduced with pShutlle-A2-F2A-BM; the 'A375-pShuttle-A2-F2A-NY', SKOV3-pShuttle-A2-F2A-NY' and SKOV3-NY-pShuttle-A2-F2A-NY' bars represent the target tumor cells that were transduced with pShutlle-A2-F2A-NY. The data was analyzed with Student's t test and ** represents p<0.01, * represents p<0.05.

Figure 4A:
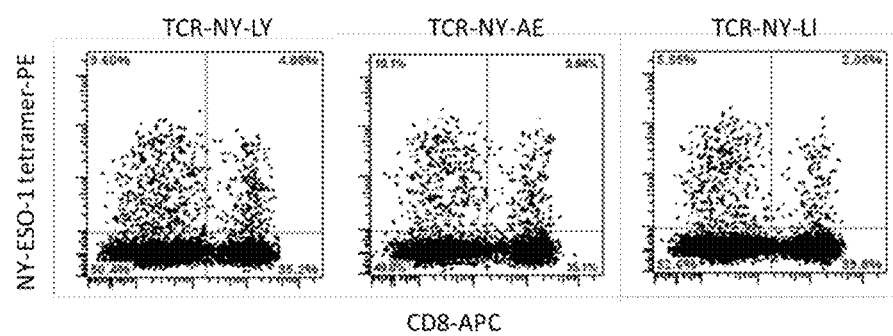

FIG. 4A shows that PBMCs transfected with the recombinant lentivirus encoding NY-ESO-1 specific TCRs can express the TCRs specific to NY-ESO-1 157-165 peptide in the context of HLA-A2. PBMC cells were infected with the fresh-made lentivirus encoding different NY-ESO-1 specific TCRs, including TCR-NY-LY, TCR-NY-AE and TCR-NY-LI. The cells were harvested in 7-10 days, stained with anti-CD8 antibody labelled with APC and the NY-ESO-1 157-165/HLA-A2 tetramer labelled with PE and analyzed by flow cytometry. The percentage of CD8+, tetramer+ cells and CD8–, tetramer+ cells in the gated lymphocyte population based on the forward and side scatters are shown on the flow cytometry graphs.

Figure 4B:
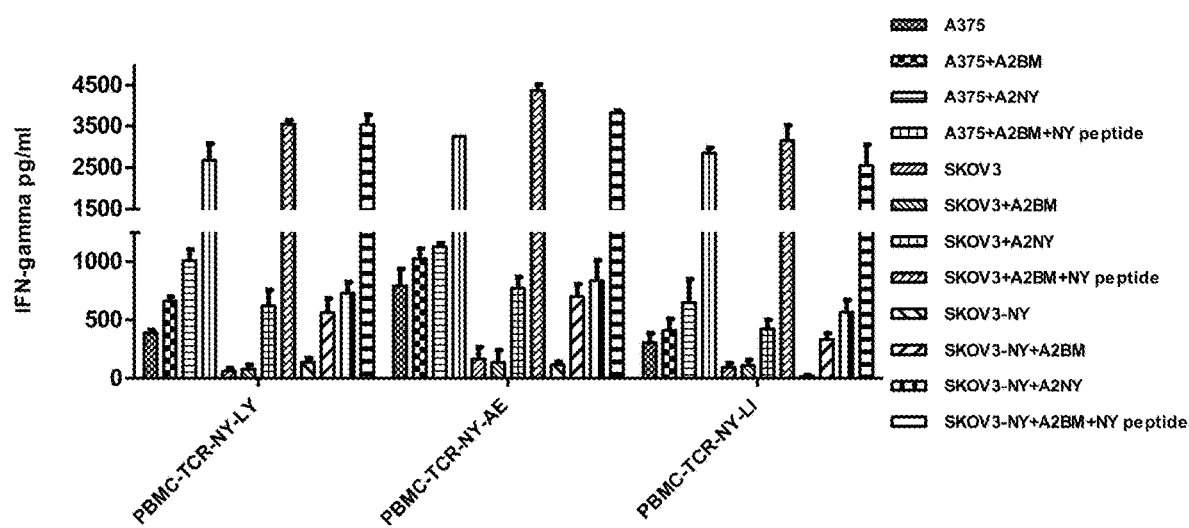

FIG. 4B shows that tumor cells can be sensitized by the labelling polypeptide containing NY-ESO-1 epitope peptides and/or exogenous HLA-A2 to be recognized by the NY-ESO-1 specific TCRs on primary T cells. Tumor cell lines A375, SKOV3 and SKOV3-NY were transduced with pShuttle-A2-F2A-NY or pShuttle-A2-F2A-BM and utilized as target cells to stimulate HLA-A2-PBMC cells expressing NY-ESO-1 specific TCRs. In duplicated wells, tumor cells and PBMC cells were mixed culture for 24 hours, the E:T ratio was 10:1. After incubation, the supernatant was harvested to assess the secretion of IFN-gamma by the T cells. X-axis shows PBMC cells expressing different TCRs specific to NY-ESO-1, including PBMC-TCR-NY-LY, PBMC-TCR-NY-AE and PBMC-TCR-NY-LI. Y-axis shows the concentrations of IFN-gamma produced by specific T cells (mean±SD; n=2). The 'A375', SKOV3' and SKOV3-NY' bars represent the target cells that were not transduced; the 'A375-A2BM', SKOV3-A2-BM' and SKOV3-NY-A2-BM' bars represent the target tumor cells that were transduced with pShutle-A2-F2A-BM; the 'A375-A2-NY', SKOV3-A2-NY' and SKOV3-NY-A2-NY' bars represent the target tumor cells that were transduced with pShutlle-A2-F2A-NY; the 'A375-A2BM+NY peptide', 'SKOV3-A2-BM+NY peptide' and 'SKOV3-NY-A2-BM+NY peptide' bars represent the target tumor cells that were transduced with pShutle-A2-F2A-BM and pulsed with NY-ESO-1 157-165 peptide at 1 ug/ml. The data was analyzed with Student's t test and ** represents p<0.01, * represents p<0.05.

Figure 4C:
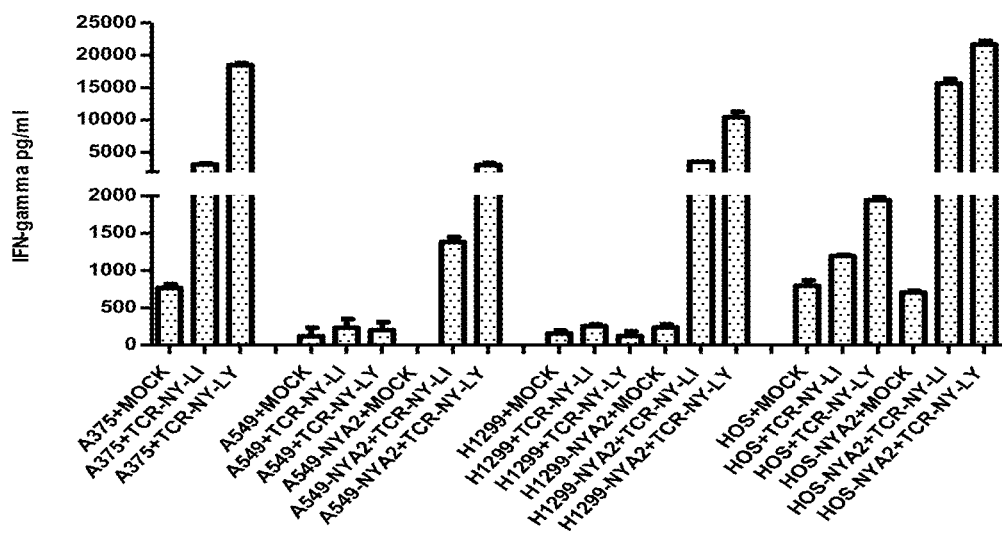

FIG. 4C shows that more tumor lines can be sensitized by the labelling polypeptide containing NY-ESO-1 epitope peptides and exogenous HLA-A2 to be recognized by the NY-ESO-1 specific TCRs on primary T cells. Tumor cell lines A549, H1299 and HOS-C1 were transduced with pShuttle-NY-A2 (A549-NYA2, H1299-NYA2 and HOS-NYA2 respectively) and utilized as target cells to stimulate PBMC cells transduced with NY-ESO-1 specific TCR genes. In triplicate wells, tumor cells and PBMC cells were mixed culture for 24 hours, the E:T ratio was 5:1. After incubation, the supernatant was harvested to assess the secretion of IFN-gamma by the T cells. X-axis shows the combination of effector cells and target cells, Y-axis shows the concentrations of IFN-gamma produced by specific T cells (mean±SD; n=3). The mock effector cells were PBMC cells transduced with an empty lentivirus. The other effector cells were PBMCs transduced with TCR-NY-LY gene and PBMCs transduced with TCR-NY-LI. The data was analyzed with Student's t test and ** represents p<0.01, * represents p<0.05.

DETAILED DESCRIPTION

The following explains in detail the specific embodiments and references to the figures of the present disclosure, but it is not the limitation of the present invention. Based on the basic principles of the present disclosure, the modifications or improvements made by the technical personnel in the field are within the scope of the present invention as long as they comply with the basic principles of the present disclosure.

The principles of the present disclosure include (1) to label the tumor/cancer cells with a labelling polypeptide comprising one or more antigenic epitope peptide(s) that can be recognized by a specific TCR, and/or an exogenous HLA protein that can present the said antigenic epitope peptide(s); the antigenic epitope peptide(s) either are delivered into tumor/cancer cells by the said labelling polypeptide or are derived from the endogenous tumor antigens, including the overexpressed tumor-associated antigens as well as tumor specific neoantigens that are generated from mutant self-proteins; (2) to eliminate the tumor cells that are labeled with the said labelling polypeptide and/or the exogenous HLA protein by the adoptively transferred immune cells that can specifically recognize the said antigenic epitope peptide(s) presented by the said HLA protein, preferably the immune cells are TCR genetically modified T cells. In the other aspect, utilizing oncolytic viruses described in the present disclosure as a vehicle to deliver the nucleic acid encoding the said labelling polypeptide and/or the exogenous HLA protein into tumor cells not only make the tumor cells become more sensitive to be targeted by the adoptively transferred T cells, but also augment the anti-tumor function of the adoptively transferred T cells in immunosuppressive tumor microenvironment.

Specifically, the present invention provides a therapeutic agent for the treatment of tumors and/or cancers, comprising:

(1) A therapeutic agent for the treatment of tumors and/or cancers, comprising:

(a) a first composition, the said the first composition comprises a first active ingredient located in a first druggable vehicle, the said the first active ingredient comprises or contains the nucleic acid encoding a labelling polypeptide, and/or an MHC protein; the said nucleic acid can be delivered into tumor cells and/or cancer cells and caused to express specific targets or target antigens that can be recognized by immune cells; the said labelling polypeptides comprise one or more antigenic epitope peptides; the said MHC protein comprise the HLA class I protein; and (b) a second composition, the said second composition comprises a second active ingredient. The said second active ingredient comprises immune cells purified from peripheral blood or from tumor tissue and are cultured in vitro; or TCR genetically modified immune cells; preferably, the second active ingredient contains TCR genetically modified T cells.

Degradation of tumor antigenic proteins is mediated by cytosolic and nuclear proteasomes, and the resulting peptides including antigenic epitope peptides are translocated into the endoplasmic reticulum (ER) where the epitope peptides, MHC class I molecules and β2-microglobulin are assembled to form the epitope peptide/MHC class I complexes. The epitope peptide/MHC complexes are presented on the surface of tumor cells and make them become the targets of T cells. The intact machinery of the class I antigen processing and presenting requires not only MEW class I molecules and β2-microglobulin but also other functional molecules such as TAP, immunoproteasomes, chaperone proteins and others. However, in the tumor cells, the expression or the function of these antigen processing and presenting related proteins are often aberrant and causes the immune escape from the T cell recognition and attack due to the deficient presentation of tumor antigenic epitope on tumor cell surface.

In the present invention, the said labelling polypeptide comprising a N-terminal signal peptide that can lead the antigenic epitope peptides (e.g., the entire labelling polypeptide) into endoplasmic reticulum where the epitope peptides are released by the cleavage of the linker peptide by the relevant enzymes in ER, and subsequently bind to the MEW class I molecules and β2-microglobulin to form peptide/MHC complexes that are presented on the cell surface. Therefore, once expressing the said labelling polypeptide the tumor cells with aberrant MEW class I antigen presenting machinery or even absent of tumor antigen expression can still be targeted by the adoptive T cell therapy.

MHC restriction is another issue encountered by adoptive T-cell therapy. Tumor antigen specific T cells recognize the antigenic epitope peptide presented on tumor cells only in the context of a particular MEW allele, which significantly limits the application scope of adoptive T cell therapy. In the present invention, the nucleoid acids encoding an exogenous HLA protein is delivered into tumor cells where the tumor antigenic epitope peptides that cannot be presented by endogenous autologous HLA protein will be presented by the exogenous HLA protein and make the tumor cells be recognized and killed by the adoptively transferred T cells that are specific to the tumor antigenic epitope in the context of the exogenous HLA. Therefore, if tumor cells overexpress a specific tumor-associated antigen or express a specific neoantigen, even though they do not possess the HLA allele that encodes endogenous HLA proteins that can present the tumor antigen epitope peptides, they still can become the target cells of the adoptive T cell therapy when the cognate exogenous HLA is expressed as described in the present disclosure. Moreover, even if the nucleoid acids encoding an exogenous HLA protein is unwantedly delivered into normal cells, the normal cells may escape the attack by the adoptively transferred T cells due to lacking tumor antigen, which may mitigate the possible safety concerns.

The amino acid sequence of the antigenic epitope peptide can be derived from a native protein, or from an artificial sequence that does not exist in nature, preferably, from a native protein including human proteins and proteins of other species other than humans. More preferably, the amino acid sequence of the antigenic epitope peptide is derived from the tumor-associated antigen or tumor-specific antigen including neoantigens.

In the present disclosure, tumor-associated antigen and tumor-specific antigen are sometimes referred to as tumor antigen.

In some embodiments, the said antigenic epitope peptide is typically between 8-11 amino acids in length and can be presented by MHC Class I molecules. In some embodiments, the antigenic epitope peptide is any one of the antigenic epitope peptides described in the Cancer Antigen Peptide Database. In an embodiment, the antigenic epitope peptides include NY-ESO-1 157-165 as shown in SEQ ID NO: 2, and also includes, but is not limited to, NY-ESO-1 1-11, NY-ESO-1 53-62, NY-ESO-1 18-27, Her2/neu 369-377, SSX-2 41-49, MAGE-A4 230-239, MAGE-A10 254-262, MAGE-C2 336-344, MAGE-C2 191-200, MAGE-C2 307-315, MAGE-C2 42-50, MAGE-A1 120-129, MAGE-A1 230-238, MAGE-A1 161-169, KK-LC-1 76-84, p53 99-107, PRAME 301-309, Alpha fetoprotein 158-166, HPV16-E6 29-38, HPV16-E7 11-19, HPV16-E7 11-19, EBV-LMP1 51-59, EBV-LMP1 125-133.

In an aspect, the said antigenic epitope peptide is derived from a neoantigen that is generated from the genetic mutation. Preferably, the antigenic epitope peptides comprising a point mutation include KRAS: G12D 10-18 as shown in SEQ ID NO: 3, and also include, but is not limited to, KRAS: G12D 7-16, KRAS: G12C 8-16, KRAS: G12A 8-16, KRAS: G12S 8-16, KRAS: G12R 8-16, KRAS: G12V 8-16, KRAS: G12V 7-16, KRAS: G12V 5-14, KRAS: G12V 11-19, KRAS: G12V 5-14, KRAS: Q61H 55-64, KRAS: Q61L 55-64, KRAS: Q61R 55-64, KRAS: G12D 5-14, KRAS: G13D 5-14, KRAS: G12A 5-14, KRAS: G12C 5-14, KRAS: G12S 5-14, KRAS: G12R 5-14, KRAS: G12D 10-19, KRAS: G12D 10-18, TP53: V157G 156-164, TP53: R248Q 240-249, TP53: R248W 240-249, TP53: G245S 240-249, TP53: V157F 156-164, TP53: V157F 149-158, TP53: Y163C 156-164, TP53: R248Q 247-255, TP53: R248Q 245-254, TP53: R248W 245-254, TP53: G245S 245-254, TP53: G249S 245-254, TP53: Y220C 217-225, TP53: R175H 168-176, TP53: R248W 240-249, TP53: K132N 125-134, CDC73: Q254E 248-256, CYP2A6: N438Y 436-444, CTNNB1: T41A 41-49, CTNNB1: S45P 41-49, CTNNB1: T41A 34-43, CTNNB1:S37Y 30-39, CTNNB1:S33C 30-39, CTNNB1: S45P 40-49, EGFR: L858R 852-860, EGFR: T790M 790-799, PIK3CA: E542K 533-542, PIK3CA: H1047R 1046-1055, GNAS: R201H 197-205, CDK4:R24C 23-32, H3. 3: K28M 27-36, BRAF: V600E 591-601, CHD4: K73Rfs 141-148, NRAS: Q61R 55-64, IDH1: R132H 126-135, TVP23C: C51Y:51-59, TVP23C: C51Y 42-51, TVP23C: C51Y:45-53.

In other embodiments, the said antigen epitope peptide is a peptide with 4-9 consecutive identical amino acids (e.g., 4, 5, 6, 7, 8 or 9 consecutive identical amino acids) with the antigen epitope peptide described above, and the said peptides is 8-11 amino acids in length.

In some embodiments, the labelling polypeptides comprising a N-terminal signal peptide that can lead the labelling polypeptide into endoplasmic reticulum and circumvent the antigen processing in cytoplasm and the access into ER without the help of TAP molecules. The said signal peptides include, but not limited to, INSL5: 1-22 as shown in SEQ ID NO:1.

In some embodiments, the said labelling polypeptide comprises multiple antigenic epitope peptides, and between each epitope peptide there is a self-cleaving linker peptide. The self-cleaving linker peptide includes an Arg-X-[Lys/Arg]-Arg (X is any amino acid residue) sequence that is recognized and cleaved at downstream by furin enzyme that is enriched in the Golgi apparatus and ER (Molecular Therapy 2007; 15(6): 1153-1159). Preferably, the amino acid sequence of self-cleaving linker peptide is Arg-Arg-Lys-Arg as shown in SEQ ID NO: 37. Once the said labelling polypeptide is imported into the ER by the said signal peptide, furin enzyme cleaves the Arg-X-[Lys/Arg]-Arg sequence and releases the said antigenic epitope peptide that subsequently binds to HLA molecules and beta2-microglobulin to form a HLA class I/peptide complex. The assembled complexes are transported to the tumor cell surface as the target of the specific T cells. Other enzymes including aminopeptidase and carboxypeptidase may also involve in the trimming process (also termed as cleaving process) to release the antigenic epitope peptides (J Immunol. 2009; 183 (9): 5526-5536). In one aspect, the furin enzyme cleavage peptide is Arg-Arg-Lys-Arg as shown in SEQ ID NO: 37.

In order to make the said labelling polypeptides stay in the endoplasmic reticulum (ER) to complete the trimming process and release the antigenic epitope peptides for binding to HLA class I molecules, an ER retention signal sequence is connected at C-terminal end of the labelling polypeptide. One type of ER retention signal sequence is Lys-Lys-X-X (X is any amino acid residue), preferably Lys-Asp-Glu-Leu as shown in SEQ ID NO: 38, that prevents the protein from being secreted from ER (Molecular Biology of the cell. 2003; 14 (3): 889-902). In one aspect, the ER retention signal sequence located on the C-terminal end of the said labelling polypeptide is the Lys-Asp-Glu-Leu as shown in SEQ ID NO: 38.

In an aspect, the said labelling polypeptide comprises operable and tandem amino acids which comprising the following: N-terminal signal peptide, one or more of the antigenic epitope peptides, and/or a C-terminal endoplasmic reticulum (ER) retention signal sequence. In an aspect, when the labelling polypeptide comprises multiple antigenic epitope peptides, each of the two adjacent antigenic epitope peptides is connected by a self-cleaving linker peptide as shown in SEQ ID NO: 13 or SEQ ID NO:14.

Preferably, the labelling polypeptide comprises N number of antigenic epitope peptides (preferably NY-ESO-1 157-165; or KRAS: G12D 10-18) connected by the self-cleaving peptide Arg-Arg-Lys-Arg as shown in SEQ ID NO: 37; In an aspect, N is an integer greater than or equal to 1, e.g., n=1, 2, 3, 4, 5, 6, 7, 8, 9, 10, 11, or 12, preferably, n=3. In an aspect, N is an integer between 1-20 (for example, an integer between 2-20), preferably, N is an integer between 1-10 (for example, an integer between 2-10).

The expression of HLA proteins is often aberrant in tumor cells caused by the Loss of Heterozygosity (LOH) that occurred in different tumor types from 65% to 90% (Immunol Today. 1997; 18:89-95). In addition, some cancer-driven gene mutations such as KRAS codon G12 mutations can also cause the deficient expression of HLA class I molecules in lung cancer cells (J Int Med Res. 2013; 41(5): 1473-83). Therefore, in some embodiments, the nucleic acid encodes both the labelling polypeptide and exogenous HLA protein, the nucleic acid encodes a labelling polypeptide and concurrently encodes an exogenous HLA protein that can present the said antigenic epitope peptide to the cell surface; the expression of HLA protein and the labelling polypeptide are under the control of the separate promoters, or under the control of the same promoter while the HLA protein and the labelling polypeptide are operably connected by a self-cleaving linker peptide. In an aspect, the promoter is a eukaryotic cell promoter, including a constitutive promoter or an inducible promoter. The said promoters include, but not limited to, PGK1 promoter, EF-1a promoter, CMV immediate early enhancer and promoter, SV40 promoter, UbC promoter, CAG promoter, TRE promoter, CamKIIa promoter, human beta actin promoter. The said self-cleaving linker peptides between the HLA protein and the labelling polypeptide are known in the art, such as 2A peptides, 2A peptides including but not limited to F2A peptides from foot-and-mouth disease virus and similar 2A peptides from other viruses (Sci Rep. 2017; 7:1-9).

In an aspect, the MHC protein is HLA class I protein, including HLA-A, B, C. Preferably, the HLA protein is HLA-A*02:01 protein and the amino acid sequence is as shown in SEQ ID NO: 5. Because the cytoplasmic tail of HLA-C protein contains a dihydrophobic (LI) internalization and lysosomal targeting signal and isoleucine at position 337 were key amino acids that affected the activity of this motif. Changing isoleucine at position 337 in the HLA-C tail to the threonine found in HLA-A and B tails (I337T) increased surface expression (J Immunol 2008, 180 (12) 7804-78170). Preferably, the amino acid sequence of HLA-C, as shown in SEQ ID NO: 6, contains a I337T point mutation and a E334V point mutation.

In some embodiments, the said nucleoid acids encoding a labelling polypeptide comprising one or more antigenic epitope peptide and an exogenous HLA protein that can present the said antigenic epitope peptide. Preferably, the combinations of the HLA protein and the labelling polypeptide are listed as following: HLA-A-02:01 protein with the labelling polypeptide comprising antigenic epitope peptide NY-ESO-1 157-165 as shown in SEQ ID NO: 24; HLA-C*08:02 protein comprising I337T and E334V mutations with the labelling polypeptide comprising antigenic epitope peptide KRAS: G12D 10-18 as shown in SEQ ID NO: 25; HLA-A-01:01 protein with the labelling polypeptide comprising antigenic epitope peptide KRAS: Q61H 55-64, KRAS: Q61L 55-64, or KRAS: Q61R 55-64; HLA-A-02:01, HLA-A-02:03 or HLA-A-02:06 protein with the labelling polypeptide comprising antigenic epitope peptide NY-ESO-1 157-165, Her2/neu 369-377, NY-ESO-1 1-11, NY-ESO-1 53-62, NY-ESO-1 18-27, SSX-2 41-49, MAGE-A4 230-239, MAGE-A10 254-262, MAGE-C2 336-344, MAGE-C2 191-200, MAGE-C2 307-315, MAGE-C2 42-50, MAGE-A1 120-129, MAGE-A1 230-238, MAGE-A1 161-169, KK-LC-1 76-84, p53 99-107, PRAME 301-309, Alpha fetoprotein 158-166, HPV16-E6 29-38, HPV16-E7 11-19, HPV16-E7 11-19, EBV-LMP1 51-59, EBV-LNIP1 125-133, KRAS: G12V 5-14, KRAS: G12D 5-14, KRAS: G13D 5-14, KRAS: G12A 5-14, KRAS: G12C 5-14, KRAS: G12S 5-14, KRAS: G12R 5-14, TP53: R248Q 247-255, TP53: R248Q 245-254, TP53: R248W 245-254, TP53: G245S 245-254, TP53: G249S 245-254, TP53: Y240C 217-225, TP53: R175H 168-176, CTNNB1: T41A 34-43, CTNNB1:S37Y 30-39, CTNNB1:S33C 30-39, EGFR: T790M 790-799, GNAS: R201H 197-205, CDK4:

R24C 23-32, H3. 3: K28M 27-36, TVP23C: C51Y 51-59 or CDC73:Q254E; The HLA-A-03:01 protein with the labelling polypeptide comprising antigenic epitope peptide KRAS: G12V 8-16, KRAS: G12V 7-16, CTNNB1: S45P 41-49, CTNNB1: S45P 40-49, BRAF: V600E 591-601 or TP53-V157G 156-164; The HLA-A11:01 protein with the labelling polypeptide comprising antigenic epitope peptide KRAS: G12D 8-16, KRAS: G12D 7-16, KRAS: G12C 8-16, KRAS: G12A 8-16, KRAS: G12S 8-16, KRAS: G12R 8-16, KRAS: G12V 8-16, KRAS: G12V 7-16, TP53: R248Q 240-249, TP53: R248W 240-249, TP53: G245S 240-249, TP53: V157F 156-164, TP53: V157F 149-158, TP53: Y163C 156-164, CTNNB1: T41A 41-49, CTNNB1: S45P 41-49, EGFR: L858R 852-860 or PIK3CA: E542K 533-542; The HLA-A24:02 protein with the labelling polypeptide comprising antigenic epitope peptide TP53: K132N 125-134; The HLA-A68:01 protein with the labelling polypeptide comprising antigenic epitope peptide TP53 R248W 240-249; The HLA-B-08:01 protein with the labelling polypeptide comprising antigenic epitope peptide CHD4 K73Rfs 141-148; The HLA-B-15: 01 protein with the labelling polypeptide comprising antigenic epitope peptide TVP23C: C51Y 42-51 or IDH1: R132H 126-135; The HLA-B58: 01 protein with the labelling polypeptide comprising antigenic epitope peptide TVP23C: C51Y 45-53; The HLA-C-01:02 protein comprising I337T and E334V mutations with the labelling polypeptide comprising antigenic epitope peptide KRAS: G12V 11-19; The HLA-C-07:01 protein comprising I337T and E334V mutations coding sequence with the labelling polypeptide with the labelling polypeptide comprising antigenic epitope peptide PIK3CA: H1047R 1046-1055; The HLA-C-08:02 protein comprising I337T and E334V mutations with the labelling polypeptide comprising antigenic epitope peptide KRAS: G12D 10-19 or KRAS: G12D 10-18.

In some embodiments, the said nucleic acid codes exogenous HLA Class I protein, specifically, the HLA includes HLA-A, B, C.

The HLA protein encoding sequence is expressed under the control of an optional exogenous gene expression regulatory elements, including promoter, enhancer, enhancers, silencers and polyadenylation signals, or the druggable vehicle's own gene-expression regulatory elements.

Preferably, the nucleic acid encode the exogenous HLA class I protein, including HLA-A*02:01 protein as shown in SEQ ID NO: 5, or HLA-C*08:02 protein comprising mutations with E337V and I337T substitutions as shown in SEQ ID NO: 6; The other HLA proteins encoded by the said nucleic acid include, but are not limited to, HLA-A*01:01 protein, HLA-A*02:03 protein, HLA-A*02:03 protein, HLA-A*03:01 protein, HLA-A*11:01 protein, HLA-A*24: 02 protein, HLA-A*30:01 protein, HLA-A*68:01 protein, HLA-B*08:01 protein, HLA-B*14:02 protein, HLA-B*1501, HLA-B*58:01, HLA-C*07:01 protein, HLA-C*01:02 protein. Preferably, the HLA-C, as shown in SEQ ID NO: 3 contains the I337T point mutation, further preferably, the HLA-C contains the I337T and E334V point mutations.

In an aspect, the nucleic acid encodes HLA protein and beta-2 microglobulin protein. The beta-2 microglobulin is a human protein or a murine protein. In some embodiments, preferably, the HLA protein and the beta-2 microglobulin are simultaneously expressed and controlled by the separate promoters, or under the control of the same promoter while the HLA protein and the beta-2 microglobulin are operably connected by a self-cleaving linker peptide, as shown in SEQ ID NO: 7 or in SEQ ID NO: 8.

In an aspect, preferably, in the therapeutic agent of the present invention, the first composition and the second composition are present separately in the therapeutic agent and are not mixed with each other.

In an aspect, preferably, in the therapeutic agent of the present invention, the nucleic acid comprises DNA or RNA; the RNA comprises the messenger RNA (mRNA) that is transcribed by the said DNA.

In one aspect, the first active ingredient is a recombinant virus, the genome of the recombinant virus comprises the said nucleic acid encoding a labelling polypeptide; In another aspect, the genome of the recombinant virus comprises the said nucleic acid encoding both a labelling polypeptide and a exogenous HLA protein; The recombinant viruses include the conditionally replication-competent virus or the replication-deficient virus; preferably, the conditionally replication-competent virus is an oncolytic virus.

In one aspect, the first active ingredient is a recombinant virus, the genome of the recombinant virus comprises the said nucleic acid encoding an exogenous HLA protein; In another aspect, the genome of the recombinant virus comprises the said nucleic acid encoding both HLA protein and a beta-2 microglobulin; The recombinant virus comprises a conditionally replication-competent virus or a replication-defective virus; In one aspect, preferably, the conditionally replication-competent virus is a oncolytic virus.

In one aspect, the replication-defective recombinant virus is a viral vector that is missing one or more necessary functional genes related to virus replication, proliferation and viral particle assembly. The viral vector cannot replicate within normal cells to form progeny viruses but can express the exogenous gene products. Preferably, the replication-defective recombinant viruses are derived from the said the replication-defective recombinant virus is derived from an adenovirus, an adeno-associated virus (AAV), a herpes simplex virus, a poxvirus, an influenza virus, an Alphavirus, or a murine respirovirus.

In one aspect, preferably, the replication-defective recombinant virus is derived from a type-5 adenovirus; In an aspect, in the genome of the recombinant adenovirus, the E1 gene is deleted and replaced with the said the nucleic acid encoding a labelling polypeptide, or a labelling polypeptide and an exogenous HLA protein; In another aspect, the genome of the recombinant virus comprises the said nucleic acid encoding an exogenous HLA protein, or both HLA protein and a beta-2 microglobulin; In an aspect, preferably, the nucleic acid is controlled by the optional exogenous gene-expression regulatory elements, or recombinant adenovirus' own gene-expression regulatory elements.

In one aspect, the oncolytic virus is a virus that preferentially or selectively replicate in tumor cells and subsequently kill infected tumor cells. The released progeny viruses help destroy the remaining tumor cells (Nat Biotechnol. 2012; 30 (7): 658-70). The said conditionally replication-competent virus is a type of oncolytic virus that is derived from a wildtype or a recombinant virus with genetic mutations that acquires the capability to selectively replicate in tumor cells; Preferably, the oncolytic viruses include, but not limited to: adenovirus, poxviruses, herpes simplex virus, measles virus, Semliki forest virus, Indiana vesiculovirus, poliovirus, retrovirus, reovirus, senecavirus, Echovirus, coxsackievirus, Newcastle disease virus and Maraba virus.

In an aspect, while the oncolytic virus can selectively replicate in the tumor cells, it cannot effectively replicate in normal cells and spread the virions to damage to normal tissue cells because normal cells have an intact defense mechanism against the oncolytic virus (Nat Rev Cancer.

2017; 17 (11): 633). The tumor selectivity of the oncolytic virus is improved with the genetic engineering technologies, and the exogenous genes can be supplemented into the viral genome to further implement its anti-tumor functions. In an aspect, in addition to its oncolytic effects, the oncolytic virus can also modulate tumor microenvironment, mainly by inducing the secretion of cytokines, chemokines, releasing tumor antigens or providing immune danger signals, thereby enhancing the local anti-tumor immune response (J. Clin. Invest. 2018; 128, 1258-1260). The first oncolytic virus that was approved for the treatment of cancer is an Ad5 adenovirus based recombinant adenovirus that has been engineered to remove E1B-55K gene that interacts with p53, which is frequently dysregulated in cancer cells (Hum Gene Ther. 2018; 29 (2): 151-159). In about 50% of patients with tumor cells that lose p53 function due to genetic mutations, the oncolytic adenovirus demonstrated oncolytic effects (Nat Med 1998; 4 (9): 1098-72). Another example of adenovirus based oncolytic virus was a mutant replication-competent virus comprising a 24 base pair deletion in E1A gene and the mutant E1A protein cannot form complex with the Rb protein (Ad-delta24). Thus the Ad-delta24 virus is unable to force the progression of infected normal cells in S phase that is required for its replication, but the mutant Ad-delta24 virus can replicate in tumor cells that the disruption of Rb cell cycle control can frequently occur. (Cell 2000; 100(1): 57-70). Another approach to implement the tumor selectivity of an oncolytic adenovirus is to use tumor-specific gene promoters to drive the expression of the viral proteins that are essential for adenovirus replication. For example, the use of the alpha-fetoprotein (AFP) gene promoter to drive E1A gene in hepatocellular carcinoma cells (Hum Gene Ther. 1999; 10: 1721-33); the use of the minimal enhancer/promoter of prostate-specific antigen (PSA) to drive E1A gene in prostate cancer cells (Cancer Res. 1997; 57 (13) 2559-63); the use of osteocalcin (hOC) promoter to drive both the early viral E1A and E1B gene in prostate cancer cells (Cancer Res. 2002; 62 (11): 3084-92) or the DF3/MUC1 promoter to drive expression of E1A in MUC-1-positive breast cancer (J Clin Invest. 2000; 106 (6): 763-71). The E2F1 promoter also can be used to drive E1A expression and make the oncolytic adenovirus only efficiently replicate in the tumor cells where the free E2F1 protein is abundant (Cancer Res. 2003; 63: 1490-1499).

Although genetic engineering enhanced the tumor selectivity of oncolytic adenoviruses, the cytolytic function of oncolytic adenovirus is unavoidably compromised. For example, The E1B-55K protein also modulates transport or cytoplasmic stabilization of viral and host cell mRNA, thus E1b55K-deleted oncolytic adenovirus may affect its function to replicate and kill the infected tumor cells (Viruses. 2015; 7 (11): 5767-5779). However, if E1B-55K is retained in the virus genome, and use tumor-specific expression promoter to drive E1A expression to achieve selective replication of the virus in tumor cells, the tumor selectivity of the oncolytic adenovirus may be compromised because E1B-55K can bind E4orf6 to form a E3 ubiquitin ligase complexes that mimic E1A Effects on E2F and cause the replication of the adenovirus in normal cells (mSphere. 2015; 1(1) pii: e00014-15). In the present disclosure, oncolytic viruses not only exert their oncolytic function to kill tumor cells, but also play a role to deliver the genes encoding the labelling polypeptide comprising antigenic epitope peptide and/or the exogenous HLA protein that present the antigenic epitope peptide on the surface of tumor cells, and make the them become the target of adoptively transferred T cells that can specifically recognize the antigenic epitope(s). On the other hand, the specific T cells will eliminate the tumor cells that could not complete the virus replication due to the compromised cytolysis function of the oncolytic virus such as E1B-55K deleted adenovirus. Thus, combination of adoptive T cell therapy with the oncolytic virus will achieve a synergistic anti-tumor effect.

In one aspect, the oncolytic virus is derived from type 5 recombinant adenovirus. Preferably, in the genome of the recombinant oncolytic adenovirus, the E1B-55K genes are deleted. Because E1B-19K inhibits both death receptor-induced and intrinsically induced apoptosis through p53-dependent and p53-independent mechanisms (Cell Death Differ 2006; 13:1371-7), thus preferably, in the genome of the recombinant oncolytic adenovirus, both E1B-55K gene and the E1B-19K gene are deleted; the E1A gene is retained in the genome of the recombinant oncolytic adenovirus and controlled by the optional exogenous gene-expression regulatory elements, or the recombinant adenovirus' own E1A gene-expression regulatory elements. Preferably, the E1A protein is the type 5 adenovirus E1A-32 kDa protein as shown in SEQ ID NO: 9.

In an embodiment, at the region of the deleted E1B-55K and E1B-19K genes, oncolytic adenovirus contains the said nucleic acid encoding the labelling polypeptide, or both the labelling polypeptide and the optional HLA protein; In another aspect, the genome of the recombinant virus comprises the said nucleic acid encoding the said HLA, or both the HLA protein and the beta-2 microglobulin; In an aspect, the nucleic acid is controlled by the optional exogenous promoter including, but not limited to, PGK1 promoter, EF-1a promoter, CMV immediate early enhancer and promoter, SV40 promoter, Ubc promoter, CAG Promoter, TRE promoter, CamKIIa promoter, human beta actin promoter; In an aspect, the nucleic acid is controlled by druggable vehicle's own gene-expression regulatory elements, preferably, by the native E1B promoter (including E1B TATA box sequence) and a Kozak sequence as shown in SEQ ID NO: 10, and by the native E1B polyadenylation signal sequence.

The said oncolytic adenovirus comprises a E1A gene encoding a mutant E1A protein with a deletion of a Leu-X-Cys-X-Glu (X is any amino acid residue) motif inE1A CR2 region. The Leu-X-Cys-X-Glu motif in E1A CR2 region is responsible for binding Rb1 protein. With the deletion of this motif the oncolytic adenovirus can replicate selectively in the tumor cells with aberrant Rb/E2F1 signaling pathway. Additionally, through the Leu-X-Cys-X-Glu motif in E1A protein can bind to STING protein and prevent activation of the cGAS-STING pathway (Science. 2015 Oct. 30; 350 (6260): 568-71). The removal of Leu-X-Cys-X-Glu motif or replacing it with Val-X-Ser-X-Asp (X is any amino acid residue) motif may unleash the ability of adenovirus to activate the DNA sensing pathway for induction of type I IFNs and thus enhance the induction of the endogenous tumor-specific T cells against the tumor antigens or the function of the adoptively transferred T cells to recognize the antigenic epitopes delivered by the said labelling polypeptide. If the Rb protein binding motif Leu-X-Cys-X-Glu (X is any amino acid residue) in E1A protein is replaced with Val-X-Ser-X-Asp (X is any amino acid residue) motif, the E1A loses its ability to bind to the Rb protein (J. Virol. 2015; 68, 6697-6709). Specially in an embodiment, a oncolytic adenovirus comprises E1A gene with a 24 base pair deletion that causes the encoding protein loss amino acid residues Leu-Thr-Cys-His-Glu-Ala-Gly-Phe (SEQ ID NO: 59) as shown in SEQ ID NO: 11. In another embodiment, the said amino acid encodes a mutant E1A protein containing point mutations at L122V, C124S and E126D as shown in SEQ ID NO: 12.

Preferably, the E1A gene of the recombinant oncolytic adenovirus is controlled by a tissue-specific promoter or tumor-specific promoter. The tissue-specific promoters or tumor-specific promoters include, but not limited to, the E2F-1 promoter, the human telomerase reverse transcriptase (hTERT) promoter, the tyrosinase promoter, the Minimal enhancer/promoter of Prostate-specific antigen, the alpha-fetoprotein (AFP) gene promoter, the osteocalcin (hOC) promoter, the DF3/MUC1 promoter and COX-2 promoter.

Preferably, the E3 gene of the recombinant oncolytic adenovirus is deleted in whole or in part. This can avoid the inhibition of E3-19K protein on the HLA class I antigen presentation pathway, so that the antigenic epitope peptide delivered by the said labelling polypeptide or the endogenous tumor antigen can be more effectively presented to the tumor cell surface. Moreover, E3-10. 4 K/14. 5 K stimulates the clearance from the cell surface and subsequent degradation of the receptors for Fas ligand and TRAIL, E3-14. 7 K functions as a general inhibitor of TNF-mediated apoptosis and blocks TRAIL-induced apoptosis (Int Rev Immunol. 2004; 23(1-2):75-111). The deletion of these E3 genes prevents tumor cells from escaping the killing by the adoptively transferred T cells. Since the ADP protein (E3-11.6K) is required for efficiently cell lysis and virus release, the E3 gene encoding ADP protein can be retained and driven by native or exogenous gene-expressing regulation elements.

In some embodiments, the said oncolytic adenoviruses with functional deletions of immunodominant T-cell epitopes of adenovirus proteins including E1A, E1B, Hexon proteins, Penton base proteins, fiber proteins, capsid protein IX, DNA polymerase, and DNA-binding protein (see patent literature WO2016178167A1). The deletion of the immunodominant T-cell epitopes from adenovirus proteins can facilitate the presentation of the antigenic epitope peptides on the said labelling polypeptide.

In the therapeutic agent described in the present disclosure, the second composition comprises the immune cells, preferably T cells, that can specifically recognize the antigenic epitope peptide that is delivered into tumor cells by the said labelling polypeptide or the endogenous tumor antigenic epitope that is presented by the exogenous HLA protein encoded by the said nucleoid acid. In an embodiment, the said immune cells are generated in vitro. The method to generate antigen-specific T cells in vitro has been established and known by the technical personals in the field. Preferably, naïve T cells are isolated from peripheral blood and stimulated with antigen-presenting cells pulsed with the said antigen epitope peptide at the concentration from 0.0001 ug/ml to 100 ug/ml for 1-7 days and are subsequently expanded with the culture medium supplemented with human IL-2, IL-7, IL-15 and/or IL-21. The antigen-presenting cells include dendritic cells, B cells, or macrophages that purified from blood and cultured in vitro or the artificial antigen-presenting cells that are engineered to express antigen-presenting molecules including, but not limited to, HLA class I protein, CD80, CD83, CD86, ICOSL and/or OX40L. In another embodiment, the immune cells are generated from tumor materials from patients. The tumor-infiltrating lymphocytes (TILs) are purified and stimulated with CD3/CD28 antibodies or the antigen-presenting cells pulsed with the said antigen epitope peptide at the concentration from 0.0001 ug/ml to 100 ug/ml and are subsequently expanded with the culture medium supplemented with human IL-2, IL-7, IL-15 and/or IL-21. In another embodiment, the immune cells are the T cells that are engineered to express the TCR that is specific to the said antigenic epitope. Preferably, the second composition comprises the TCR genetically modified immune cells; the types of immune cells modified to express exogenous TCR include naïve T-cells or their precursor cells, activated T cells, NKT cells, or T-cell lines. More preferably, the immune cell modified by the TCR gene is a CD3-positive T cell.

The said TCR that is used to modify T cells comprises at least one alpha chain and one beta chain; the alpha chain and the beta chain both contain a variable region and a constant region. The said TCR is able to specifically recognize the antigenic epitope peptide derived from the said labelling polypeptide or the endogenous tumor antigenic epitope that is presented by the exogenous HLA protein encoded by the said nucleoid acid.

Because the possible mispairing of the alpha/beta chains of exogenous TCR with the alpha/beta chains of endogenous TCR of the T cells may not only disrupt the expression of the properly paired exogenous TCR, but also cause the risk of off-targeting toxicity of the mis-paired TCR against self-proteins. Preferably, the constant regions of the TCR alpha chain and beta chain are modified to reduce or avoid the mispairing. There are two methods to modify the constant regions of the TCR. In one embodiment, an additional disulfide bond is introduced into native TCR by the site-directed mutagenesis to create the alpha chain with T48C mutation and the beta chain with S57C mutation. The method is described in the reference (Cancer Res. 2007 Apr. 15; 67 (8): 3898-903). In another embodiment, the human TCR constant region sequence is to replace fully or partially with the homologous constant region sequence of murine TCR, as described in the reference (Eur. J. Immunol. 2006 36: 3052-3059). Preferably, the human TCR constant region sequence is to replace fully or partially with the homologous murine TCR constant region sequence.

In an embodiment, the said TCR alpha chain and the beta chain are connected by a self-cleaving linker peptide. The term self-cleaving linker peptide refers to the peptide that allows multiple independent genes to be transcribed as a single mRNA. Upon translation, the self-cleaving linker peptide sequence causes a 'ribosome skip' generating two independent gene products. This type of self-cleaving linker peptides are derived from a 18-22 amino acid long viral oligopeptides, including, but not limited to, F2A (foot-and-mouth disease virus 2A peptide), T2A (Thosea asigna virus 2A-like peptide), P2A (porcine teschovirus-1 2A peptide) or E2A (equine rhinitis A virus 2A peptide). In another aspect, the self-cleaving linker peptides refers to a peptide comprising an Arg-X-Lys/Arg-Arg motif that can be cleaved by furin enzyme. Preferably, the self-cleaving linker peptides contains a F2A peptide and a furin-cutting motif sequence Arg-Arg-Lys-Arg (SEQ ID NO: 37).

In one embodiment, the TCR that is used to modified the said T cells specifically recognize NY-ESO-1 157-165 peptide in the context of HLA-A*02:01; specifically, the variable regions of alpha chain and beta chain are described in the reference disclosures (U.S. Pat. No. 8,143,376B2; U.S. Pat. No. 8,143,376B2) and the reference literature (J Immunol 2010; 184 (9), 4936-46). Preferably, the constant region sequence of the said TCR alpha chain and beta chain are fully replaced with the constant region sequence of murine TCR alpha chain and beta chain respectively; preferably, the said NY-ESO-1 157-165 peptide specific TCR alpha chain and beta chain are connected by a self-cleaving connected peptide comprising a furin enzyme cutting peptides and a F2A peptides. The amino acid sequences of the said TCR alpha chain and beta chain connected with a self-cleaving connected peptideare shown in SEQ ID NO: 26, 27 or 28.

In one embodiment, the TCR that is used to modify the said T cells specifically recognize KRAS: G12D 10-18 peptide in the context of HLA-C*08:0 2; specifically, the variable regions of alpha chain and beta chain are described in the reference disclosures (WO2018026691). Preferably, the constant region sequence of the said TCR alpha chain and beta chain are fully replaced with the constant region sequence of murine TCR alpha chain and beta chain respectively; Preferably, the said TCR alpha chain and beta chain are connected by the self-cleaving connected peptide comprising a furin enzyme cutting peptides and a F2A peptides. The amino acid sequence of the said TCR alpha chain and beta chain connected with a self-cleaving connected peptide is shown in SEQ ID NO: 29.

In one embodiment, the TCR that is used to modify the said T cells specifically recognize KRAS: G12D 10-19 peptide in the context of HLA-C*08:0 2; specifically, the variable regions of alpha chain and beta chain are described in the reference disclosure (WO2018026691).

In another embodiment, the TCR that is used to modify the said T cells specifically recognize KRAS: G12D 7-16 peptide in the context of HLA-A*11:01; specifically, the variable regions of alpha chain and beta chain are described in the reference disclosure (WO2016085904A1).

In one embodiment, the TCR that is used to modify the said T cells specifically recognize MAGE-A4 230-239 peptide in the context of HLA-A*02:01; specifically, the variable regions of alpha chain and beta chain are described in the reference disclosure (WO 2017174823A1).

In one embodiment, the TCR that is used to modify the said T cells specifically recognize MAGE-A10 254-262 peptide in the context of HLA-A*02:01; specifically, the variable regions of alpha chain and beta chain are described in the reference disclosure (WO2016055785).

In one embodiment, the TCR that is used to modify the said T cells specifically recognize alpha fetoprotein 158-166 peptide in the context of HLA-A*02:01; specifically, the variable regions of alpha chain and beta chain are described in the reference disclosure (US20160137715A1).

In one embodiment, the TCR that is used to modify the said T cells specifically recognize H3.3: K27M 26-35 peptide in the context of HLA-A*02:01; specifically, the variable regions of alpha chain and beta chain are described in the reference disclosure (US20170281742A1).

The present invention also includes a separate nucleic acid encoding at least one of an alpha chain and a beta chain of the said TCR; the T cell receptor can specifically recognize the antigenic epitope peptide on the said labelling polypeptide or the endogenous tumor antigenic epitope that is presented by the said exogenous HLA protein.

The nucleic acid is DNA or RNA.

In the specific embodiments, the nucleic acid encodes the said TCRs are shown in SEQ ID NOs: 30, 31, 32, or 33.

Wherein, the variable region encoding sequence of alpha chain is from human TCR; the constant region encoding sequence of alpha chain is from murine TCR.

Wherein, the variable region encoding sequence of beta chain is from human TCR; the constant region encoding sequence of beta chain is from murine TCR.

Wherein, the nucleic acid encoding the self-cleaving connected peptide such as a furin cleavage peptides and a F2A peptides.

The present invention also discloses a recombinant druggable vehicle comprising the nucleic acid (e.g., DNA) and/or its complementary sequence that encode TCR amino acid sequences described in the present invention.

Preferably, in the recombinant druggable vehicle, the nucleic acid encoding the said TCR are controlled by exogenous gene-expression regulatory elements including the promoter, enhancer, silencer and polyadenylation signal. The combination of the above regulatory elements facilitates the transcription and translation of genes and enhances the stability of mRNA.

The recombinant druggable vehicle can be any known druggable vehicle that can be used to deliver and/or express a nucleic acid molecule, including, but not limited to, plasmid or virus. The viral vectors include, but are not limited to (for example), retroviral vectors (derived from Moloney murine leukemia Virus), lentiviral vectors (derived from human immunodeficiency type I virus (HIV)). In an aspect, the vectors are recombinant vectors such as recombinant viral vectors. In an aspect, the said recombinant vectors comprising the TCR genes can be produced with the conventional recombinant technology in the art.

In one embodiment, the expression of TCR alpha and beta-chain genes on recombinant druggable vehicles can be driven by two different promoters including strong promoter, weak promoter, constitutive promoter, inducible promoter, tissue-specific promoter, or differentiation-specific promoter. The promoter can be from a viral source or a non-viral source (e.g., eukaryotic promoter), such as PGK1 promoter, EF-1a promoter, CMV immediate early enhancer and promoter, SV40 promoter, Ubc promoter, CAG Promoter, TRE promoter, CamKIIa promoter, human beta actin promoter. In some embodiments, when two promoters drive two genes, the dual promoters are arranged in the opposite orientation or in the same orientations.

In another embodiment, the expression of the said TCR alpha and beta-chain genes on recombinant druggable vehicles can be driven by the same promoter while they are operably connected by a nucleic acid encoding a self-cleaving linker peptide such as a furin cleavage peptides and a F2A peptides.

In other embodiments, the recombinant druggable vehicles comprise a nucleic acid encoding other functional molecules in addition to amino acid sequences of the said TCR alpha and beta-chain. In one embodiment, the other functional molecule is the fluorescent proteins (such as GFP proteins) for the tracking of the T cells in vivo. In another embodiment, the recombinant druggable vehicles comprise a suicide gene to improve the safety of the adoptive T cell therapy. The suicide gene is a genetically encoded molecule that allows selective destruction of adoptively transferred cells (Front. Pharmacol., 2014; 5(254):1-22). The suicide genes encoded molecules include, but not limited to, herpes simplex virus thymidine kinase, ganciclovir, cytosine deaminase, 5-fluorocytosin, 5-fluorouracil, inducible FAS, inducible Caspase9, truncated CD20, EGFR, c-myc or RQR8. The nucleic acid encoding suicide gene and the nucleic acid encoding the said TCR are controlled independently by the different promoters; or by the same promoter while the TCR gene and the suicide gene are connected with the said self-cleaving linker peptide described above.

Preferably, the first composition contains the therapeutically effective dose of the said DNA, or the therapeutic effective dose of the said mRNA.

Preferably, the first composition comprises the therapeutically effective dose of the said recombinant virus. More preferably, when the recombinant virus is the said recombinant oncolytic adenovirus, the oncolytic adenovirus is administered at a dose of 5×107-5×1012 vp/day, 1-2 times a day for 1-7 days continuously.

Preferably, the second composition comprises the second composition comprises the therapeutically effective dose of the said immune cells. More preferably, the second composition comprises the therapeutically effective dose of T cells modified by TCR gene. Further preferably, the TCR genetically modified T cells are administered with a total dose range of 1×10e3–1×10e9 cells/kg of weight per treatment course.

The said DNA or RNA can be formulated to administer intratumorally, for example, in the form of purified plasmids, liposome-encapsulated plasmids, nanoparticle-conjugated plasmids (nanoparticles are formed with Poly-L-Lysine, polyethylene, Chitosan or other polymers). The plasmids DNA is directly injected within the tumor; after DNA injection, electro-transportation can be applied to enhance the delivery of DNA into tumor cells.

The said the recombinant virus is formulated to administer intratumorally, intra-peritoneally, intrathecally, or intravenously.

The said immune cells are formulated and given through the routes as following: the intraarterial, intravenous, subcutaneous, intracutaneous, intratumoral, intra-lymphatic, intrathecal, intracerebrospinal, intra-bone marrow, intramuscular or intra-peritoneal administration.

Preferably, the said therapeutic agent consists of the first composition and the second composition.

The technical personnel in the field can understand that the therapeutic agent of the present invention may also comprise the druggable excipients and additives, including pharmaceutical or physiological vehicles, excipients, diluents (including normal saline or phosphate buffered saline); the additives include carbohydrates, lipids, peptides, amino acids, antioxidants, adjuvants, preservation agents and others known in the field.

The present invention also provides the applications of any said therapeutic agent in the preparation/manufacturing of drugs for the treatment of tumors and/or cancers.

The said tumors and/or cancers include: the tumors and/or cancers described include, but not limited: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, Pheochromocytoma, Prolactinoma, von Hippel-Lindau disease, Zollinger-Ellison syndrome, anal cancer, Cholangiocarcinoma, bladder cancer, urethral cancer, glioma, neuroblastoma, meningioma, spinal cord tumor, Bone tumor, chondrosarcoma, Ewing's sarcoma, cancer of unknown primary site, Carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, Multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, Cardiac Sarcoma, Meningeal carcinomatosis, primary peritoneal carcinoma and malignant pleural mesothelioma.

The present invention also provides a labelling polypeptide described above, and the exogenous HLA protein described above.

Preferably, at least 98% of the amino acid sequence of the labelling polypeptide is the same as the amino acid sequence shown in SEQ ID NOs:13 or 14; more preferably at least 98.5%, preferably at least 99%.

Preferably, the amino acid sequence of the exogenous HLA protein comprises the coding sequence of the HLA-A*2:01 protein as shown in SEQ ID NO: 5, or the HLA-C*08:02 protein comprising E337V and I337T point mutations as shown in SEQ ID NO: 6. The other HLA proteins include but not limited to, HLA-A*01:01 protein, HLA-A*02:03 protein, HLA-A*02:06 protein, HLA-A*03:01 protein, HLA-A*11:01 protein, HLA-A*24:02 protein, HLA-A*30:01 protein, HLA-A*68:01 protein, HLA-B*08:01 protein, HLA-B*14:02 protein, HLA-B*1501, HLA-B*58:01, HLA-C*07:01 protein, HLA-C*01:02 protein. Preferably, the HLA-C, as shown in SEQ ID NO: 6 contains the I337T point mutation, further preferably, the HLA-C contains the I337T and E334V point mutations.

The invention also provides an application of the nucleic acids, and/or its complementary sequence to prepare or manufacture drugs for the treatment or prevention of tumors and/or cancers.

The present invention also provides an application of the recombinant druggable vehicle to prepare or manufacture drugs for the treatment or prevention of tumors and/or cancers.

Preferably, in the recombinant druggable vehicle, the said nucleic acid are properly connected to a gene-expression regulatory element including the promoter, enhancer, silencer and polyadenylation signal. The gene-expression regulatory elements can facilitate the transcription and translation of genes and enhance the stability of mRNA The recombinant druggable vehicles include plasmids or viruses. The viral vectors include the conditionally replication-competent virus or the replication-deficient virus, preferably, the conditionally replication-competent virus is the oncolytic virus. The said the replication-defective recombinant virus is originated from adenovirus, adeno-associated virus (AAV), herpes simplex virus, poxvirus, influenza virus, Alphavirus, or murine respirovirus; the oncolytic viruses are originated from the viruses including but not limited: adenovirus, poxviruses, herpes simplex virus, measles virus, Semliki forest virus, Indiana vesiculovirus, poliovirus, retrovirus, reovirus, senecavirus, Echovirus, coxsackievirus, Newcastle disease virus or Maraba virus.

The said recombinant vectors comprising the said nucleic acid encoding the labelling polypeptide, and/or exogenous HLA protein can be produced with the conventional recombinant technologies in the art.

In other embodiments, the recombinant druggable vehicles in addition to comprising the nucleic acid described in the present invention, can also comprise the nucleic acid encode other functional molecules, such as reporting genes which can be applied to detect the cells that are transfected with the recombinant druggable vehicles, or the expression levels or activity of the encoded proteins. The detection technologies are the methods known in the field such as flow cytometry, immunohistochemistry analysis, Fluorescence in situ Hybridization, or PCR technology.

The present invention also provides an application of the nucleic acid to prepare or manufacture drugs for the treatment or prevention of tumors and/or cancers.

The invention also provides an application of the recombinant druggable vehicle to prepare or manufacture drugs for the treatment or prevention of tumors and/or cancers.

The present invention also provides an application of the recombinant virus to prepare or manufacture drugs for the treatment or prevention of tumors and/or cancers. The recombinant virus comprises a conditionally replication-competent virus or a replication-deficient virus, preferably, the conditionally replication-competent virus is an oncolytic virus as described above.

The invention also provides an application of the drug combination to prepare or manufacture drugs for the treatment or prevention of tumors and/or cancers, including:

The first vehicle, the first vehicle comprises the first composition in any of the therapeutic agents described in the present invention;

The second vehicle, the second vehicle comprises the second composition in any of the therapeutic agents described in the present invention;

The first vehicle and the second vehicle are separated; and a manual of the timing and manner of drug administering is provided.

The said tumors and/or cancers include but not limited: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, Pheochromocytoma, Prolactinoma, von Hippel-Lindau disease, Zollinger-Ellison syndrome, anal cancer, Cholangiocarcinoma, bladder cancer, urethral cancer, glioma, neuroblastoma, meningioma, spinal cord tumor, Bone tumor, chondrosarcoma, Ewing's sarcoma, cancer of unknown primary site, carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, cardiac sarcoma, meningeal carcinomatosis, primary peritoneal carcinoma and malignant pleural mesothelioma.

In some embodiments, if the first composition is any of the therapeutic agents described in (1), (2), (3), (4), (5), (6), (7), (12), (13), (14), (16), (17), (18), (19), (19)), (20), (21), (22), (23), (24), (25), (26), (27), (28), (29) or (30), according to the actual situation of the tumor and/or cancer patients, the patient with tumor and/or cancer described as following can be provided with the drug/treatment herein within the scope of the present invention: the said tumor and/or cancer cells express both the said tumor antigen and the said HLA protein that can present the antigenic epitope derived from the said tumor antigen; the said tumor and/or cancer cells express the said tumor antigen but do not express the said HLA protein; the said tumor and/or cancer cells express neither the said tumor antigen nor the said HLA protein.

In some embodiments, If the first composition is any of the therapeutic agents described in (1), (8), (9), (10), (11), (12), (13), (15), (16), (17), (18), (19), (20), (21), (22), (23), (24), (25), (26), (27), (28), (29) or (30), according to the actual situation of the tumor and/or cancer patients, the patient with tumor and/or cancer described as following can be provided with the drug/treatment herein within the scope of the present invention: the said tumor and/or cancer cells express both the endogenous tumor antigen and the HLA protein that can present the antigenic epitope peptide derived from the said tumor antigen; the said tumor and/or cancer cells should express the endogenous tumor antigen but do not express the HLA protein that can present the antigenic epitope peptide derived from the said tumor antigen More specifically, in an embodiment, the first composition of the therapeutic agent described above comprises HLA-A-02:01, HLA-A-02:03, or HLA-A-02:06, and is applied to treat the patients with tumor and/or cancer cells that express the tumor antigens including, but are not limited to, NY-ESO-1, Her2/neu, SSX-2, MAGE-C2, MAGE-A1, M-2433-233, MAGE-A10 254-262, KK-LC-1, p53, PRAME, Alpha fetoprotein, HPV6-E6, HPV16-E7, EBV-LMP1, KRAS: G12D, KRAS: G12C, KRAS: G12A, KRAS: G12S, KRAS: G12R, KRAS: G12R, KRAS: G12R, KRAS: G122 V, KRAS: Q61H, KRAS: Q61L, KRAS: Q61R, KRAS: G13D, TP53: V157G, TP53: V157F, TP53: R248Q, TP53: R248W, TP53: G245S, TP53: Y163C, TP53: G249S, TP53: Y240C, TP53: R175H, TP53: K132N, CDC73: Q254E, TPP2A6: N438Y, CTNN1: T41A, CTNNB1: S45P, CTNNB1: S37Y, CTNNB1: S33C, EGFR: L858R, EGFR: T790M, PIK3CA: E542K, PIK3CA: H1047R, GNAS: R201H, CDK4:R24, R24C H3.3:K28M, BRAF: V600E, CHD4 K73Rfs, NRAS Q61R, IDH1:R132H, and TVP23C: C51Y;

In another embodiment, the first composition of the therapeutic agent described above comprises HLA-A-03:01, and is applied to treat the patients with tumor and/or cancer cells that express the tumor antigens including, but are not limited to, KRAS: G12V, CTNNB1: S45P, CTNNB1: S45P, S45P, BRAF: V600E or TP53-V157G.

In another embodiment, the first composition of the therapeutic agent described above comprises HLA-A *11: 01, and is applied to treat the patients with tumor and/or cancer cells that express the tumor antigens including, but are not limited to, KRAS: G12D, KRAS:G12C, KRAS: G12A, KRAS: G12S, KRAS: G12R, KRAS: G12V, TP53: R248Q, TP53: R248W, TP53: G245S, TP53: V157F, TP53: Y163C, CTNNB1: T41A, CTNNB1: S45P, EGFR: L858R or PIK3CA: E542K.

In another embodiment, the first composition of the therapeutic agent described above comprises HLA-A*24: 02, and is applied to treat the patients with tumor and/or cancer cells that express the tumor antigens including, but are not limited to, TP53: K132N.

In another embodiment, the first composition of the therapeutic agent described above comprises HLA-A*68:01 and is applied to treat the patients with tumor and/or cancer cells that express the tumor antigens including, but are not limited to, TP53 R248W.

In another embodiment, the first composition of the therapeutic agent described above comprise HLA-B*08:01 and is applied to treat the patients with tumor and/or cancer cells that express the tumor antigens including, but are not limited to, CHD4 K73Rfs*129.

In another embodiment, the first composition of the therapeutic agent described above comprise HLA-B*15:01 and is applied to treat the patients with tumor and/or cancer cells that express the tumor antigens including, but are not limited to, TVP23C:C51Y or IDH1: R132H.

In another embodiment, the first composition of the therapeutic agent described above comprise HLA-B*58:01 and is applied to treat the patients with tumor and/or cancer cells that express the tumor antigens including, but are not limited to, TVP23C:C51Y.

In another embodiment, the first composition of the therapeutic agent described above comprise wild-type HLA-C*01:02 or HLA-C*01:02 comprising I337T and E334V point mutations, and is applied to treat the patients with tumor and/or cancer cells that express the tumor antigens including, but are not limited to, KRAS: G12V.

In another embodiment, the first composition of the therapeutic agent described above comprise wild-type HLA-C*07:01 or HLA-C*07:01 comprising I337T and E334V point mutations, and is applied to treat the patients with tumor and/or cancer cells that express the tumor antigens including, but are not limited to, PIK3CA: H1047R.

In another embodiment, the first composition of the therapeutic agent described above comprise wild-type HLA-C*08:02 or HLA-C*08:02 comprising I337T and E334V point mutations, and is applied to treat the patients with tumor and/or cancer cells that express the tumor antigens including, but are not limited to, KRAS: G12D.

The invention also provides a method to treat tumors and/or cancers, including:

Treat the tumor and/or cancer patients with the first composition of the therapeutic agent described in the present invention; and, Treat the tumor and/or cancer patients with the second composition in the therapeutic agent described in the present invention.

The first composition and second composition in the therapeutic agent can be administered simultaneously (e.g., as a mixture administering intratumorally); can be administered separately but simultaneously (e.g., administering the first composition intratumorally and the second composition intravenously); or can be administered successively (e.g., first administering the first composition, and subsequently the second composition; or first administering the second composition, and subsequently the first composition).

Preferably, the drug administration is applied successively as the following steps:
a) administer the first composition in the said therapeutic agent to the tumor and/or cancer patient;
b) After giving the first composition, administer the second composition in the said therapeutic agent to the tumor and/or cancer patient.

Preferably, the second composition of the therapeutic agent is administered to the tumor and/or cancer patient at the 1st-30th days after the application of the first composition.

The second composition of the therapeutic agent are administered to the tumor and/or cancer patient at the 1st-30th days after the application of the first composition refers as following: the time interval between the first application of the second composition and the first application of the first composition is 1-30 days (e. g; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days), or the time interval between the first application of the second composition and the most adjacent application of the first composition before the application of the second composition is 1-30 days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days). Preferably, the time interval between the first application of the second composition and the most adjacent application of the first composition before the application of the second composition is 3-14 days (e.g., 3, 4, 5, 6, 7, 8, 9, 10, 11, 12, 13, 14 days).

In a preferred embodiment of the present invention, the first composition comprises the recombinant oncolytic adenovirus. The said recombinant oncolytic adenovirus is applied with the dose of $5\times10^7$-$5\times10^{12}$ vp/day, 1-2 times per day for 1-7 days, or any integer value between the above range.

In a preferred embodiment of the present invention, the dose of the immune cells, specifically TCR-modified immune cells, is applied at a total dose range of $1\times10^3$-$1\times10^9$ cells/Kg weight for each course of treatment. Preferably, 1-3 times per day for 1-7 days, or any integer value between the above range. When treating each individual patient, a variety of factors are considered, such as age, body weight, general health, diet, route of administration, and the severity of cancer being treated.

In some embodiments, the method of treating tumors and/or cancers also includes the combination with other drugs or methods for the treatment of tumors and/or cancers in patients, and/or for modulating the patient's immune system to enhance the proliferation and function of the adoptively transferred T cells. The other drugs or methods include, but not limited to, chemotherapy drugs such as cyclophosphamide or fludarabine, radiation therapy, Immunosuppressive drug such as cyclosporine, thiopental, methotrexate, mycophenolate, and antibodies including anti-CD3, anti-IL-2, anti-IL-6, anti-IL-17 or anti-TNF-alpha.

In some embodiments, the method of treating tumors and/or cancers also includes the combination with the drugs to eliminate the adoptively transferred T cells with suicide genes as described above in case the T cells cause serious toxic side effects. The drug or reagents that can kill the T cells with suicide genes induced the chemical inducer of dimerization (CID) drugs, such as AP1903/rimiducid, ganciclovir, anti-CD20 antibody, anti-cMYC antibody, anti-EGFR antibody.

The said DNA or RNA can be formulated for the administering intratumorally, for example, in the form of purified plasmids, liposome-encapsulated plasmids, nanoparticle-conjugated plasmids (nanoparticles are formed with poly-L-lysine, polyethylene, chitosan or other polymers), the plasmids DNA is directly injected within the tumor; After DNA injection, electro-transportation can be applied to enhance the delivery of DNA into tumor cells.

The said recombinant virus is formulated to be administered intratumorally, intra-peritoneally, intrathecally, or intravenously.

The said immune cells are formulated and given through the routes as following: the intraarterial, intravenous, subcutaneous, intracutaneous, intratumoral, intra-lymphatic, intrathecal, intracerebrospinal, intra-bone marrow, intramuscular or intra-peritoneal administration.

The said tumors and/or cancers include but not limited: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, pheochromocytoma, prolactinoma, von Hippel-Lindau disease, Zollinger-Ellison syndrome, anal cancer, cholangiocarcinoma, bladder cancer, urethral cancer, glioma, neuroblastoma, meningioma, spinal cord tumor, bone tumor, chondrosarcoma, Ewing's sarcoma, cancer of unknown primary site, carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, cardiac sarcoma, meningeal carcinomatosis, primary peritoneal carcinoma and malignant pleural mesothelioma.

Definitions

The term "administering" (or any form of administration such as "administered") as used herein refers to the delivery to a subject of a therapeutic agent such as the compositions or pharmaceutical compositions described herein.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

"Aberrant expression" or "abnormal expression" means according to the invention that expression is altered, preferably increased, compared to the state in a non-tumorigenic normal cell or a healthy individual, i.e., in an individual not having a disease associated with aberrant or abnormal expression of a certain protein, e.g., a tumor-associated antigen. An increase in expression refers to an increase by at least 10%, in particular at least 20%, at least 50% or at least 100%, or more. In one embodiment, expression is only found in a diseased tissue, while expression in a healthy tissue is repressed.

The term "about" or "approximately" as used herein means within 20%, or in some instances within 10%, or in some instances within 5%, or in some instances within 1%, or in some instances within 0.1% of a given value or range, as such variations are appropriate to perform the disclosed methods or appropriate for the intended purposes of the disclosed compositions.

The term "an active ingredient" refers to ingredient in a pharmaceutical drug product composition that is biologically active or has intended pharmaceutical effects.

The term "adoptive cell transfer" or "adoptive cell therapy" or "ACT" refers to an immunotherapy approach where a subject or patient's own immune cells (e.g., autologous T cells), or immune cells from healthy donors (e.g., allogeneic T cells) are collected to treat their cancer. TCR-T cell therapy is a type of ACT.

The term "and/or" wherever used herein includes the meaning of "and", "or" and "all or any other combination of the elements connected by said term".

The term "anti-tumor" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "antibody," as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antigen" or "Ag" as used herein is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full-length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample or might be macromolecule besides a polypeptide. Such a biological sample can include, but is not limited to a tissue sample, a tumor sample, a cell or a fluid with other biological components.

The term "antigen presenting machinery" refers to the immunological molecules or cells that process and prepare antigens for presentation to T lymphocytes. The antigen presenting machinery involves two distinct pathways for processing of antigens from an organism's own (self) proteins or intracellular pathogens (e.g., viruses), or from phagocytosed pathogens (e.g., bacteria); subsequent presentation of these antigens on Class I or Class I major histocompatibility complex (MHC) molecules is dependent on which pathway is used. Both MHC Class I and II are required to bind antigen before they are stably expressed on a cell surface. MHC I antigen presentation typically involves the endogenous pathway of antigen processing and MHC II antigen presentation involves the exogenous pathway of antigen processing.

The term "autologous" refers to any material derived from the same individual to whom it is later to be reintroduced into the individual.

The term "β2 microglobulin" or "β2 microglobulin protein" is a component of MHC class I molecules, MHC class I molecules have α1, α2, and α3 proteins which are present on all nucleated cells (excludes red blood cells).[5][6] In humans, the β2 microglobulin protein is encoded by the B2M gene.

The term "C-terminal" (also known as C-terminus, carboxyl-terminus, carboxy-terminus, C-terminal tail, C-terminal end, or COOH-terminus) refers to the end of an amino acid chain (protein or polypeptide), terminated by a free carboxyl group (—COOH). When the protein is translated from messenger RNA, it is created from N-terminus to C-terminus. The convention for writing peptide sequences is to put the C-terminal end on the right and write the sequence from N- to C-terminus.

The term "cancer" refers to a disease characterized by the rapid and uncontrolled growth of aberrant cells. Cancer cells can spread locally or through the bloodstream and lymphatic system to other parts of the body. The term "cancer" is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, prostate, ovarian, cervical, skin, pancreatic, colorectal, renal, liver cancer, colon, brain, lymphatic, and blood origin. Examples of cancers include, but are not limited to, a fibrosarcoma, myosarcoma, liposarcoma, chondrosarcoma, osteogenic sarcoma, chordoma, angiosarcoma, endothelial sarcoma, lymphangiosarcoma, lymphangioendothelioma sarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, myelofibrosis, or Kaposi sarcoma.

The term "combination" as used herein refers to any arrangement possible of various components (e.g. an oncolytic virus and one or more substance effective in anticancer therapy). Such an arrangement includes a mixture of said components as well as separate combinations for concomitant or sequential administrations. The present invention encompasses combinations with different effective dose(s). It is appreciated that the optimal dose(s) of each component of the combination can be determined by the artisan skilled in the art.

The term "composition" or "pharmaceutical composition" as used herein refers to a chemical and/or biological composition suitable for administration to a subject or patient for intended pharmaceutical effects (e.g, prophylactic and therapeutic effects). Examples of compositions appropriate for such therapeutic applications include preparations for parenteral, subcutaneous, transdermal, intradermal, intramuscular, intracoronarial, intramyocardial, intracerebral, intratumoral, intraperitoneal, intravenous (e.g., injectable), or intratracheal administration, such as sterile suspensions, emulsions, and aerosols. Intratracheal administration can involve contacting or exposing lung tissue, e.g., pulmonary alveoli, to a therapeutic agent comprising a therapeutically effective amount of nucleic acid in a druggable vehicle and/or immune cells such as T cells such as TCR-modified T cells. In some cases, pharmaceutical compositions appropriate for therapeutic applications may be in admixture with one or more pharmaceutically acceptable excipients, diluents, or carriers such as sterile water, physiological saline, glucose or the like.

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues. "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

The term "conditionally replication-competent viruses" or "conditionally replication viruses" or "CRVs" refers to viruses are designed to be capable of selectively replicating in tumor cells, leading to their destruction, while sparing normal cells.

The term "constitutive promoter" refers to a nucleotide sequence which, when operably linked with a polynucleotide which encodes or specifies a gene product, causes the gene product to be produced in a cell under most or all physiological conditions of the cell.

The term "death receptor" refers to members of the tumor necrosis factor receptor superfamily characterized by a cytoplasmic region known as the "death domain" that enables the receptors to initiate cytotoxic signals when engaged by cognate ligands.

The term "obtained from", "originating" or "originate" or "derived" is used to identify the original source of a component (e.g. polypeptide, nucleic acid molecule, amino acid sequence) but is not meant to limit the method by which the component is made which can be, for example, by chemical synthesis or recombinant means.

The term "druggable" or "pharmaceutically acceptable" refers to suitable to be used for administering to a patient or subject to achieve the intended pharmaceutical or drug effect without undue adverse side effects (such as toxicity, stimulation and allergy), e.g., with a reasonable benefit/risk ratio.

As used herein, "druggable vehicle" or "pharmaceutically acceptable vehicle" or "pharmaceutically acceptable carrier" refers to a vehicle or carrier for administration of a therapeutic agent that is suitable for human and/or mammal without undue adverse side effects (such as toxicity, stimulation and allergy) with a reasonable benefit/risk ratio. As used herein, "druggable vehicle" includes any vehicle or vector that can be used to deliver and/or express nucleic acid, including, nanoparticle, lipid, plasmid, virus or cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom. A nucleic acid or nucleic acid sequence "encoding" a peptide refers to a nucleic acid containing the coding sequence for the peptide. An amino acid sequence "encoding" a peptide refers to an amino acid sequence containing the sequence of the peptide.

The term "endogenous" refers to any material from or produced inside an organism, cell, tissue or system.

The term "endoplasmic reticulum retention signal sequence" refers to the signal sequence that causes proteins to be retained in the endoplasmic reticulum, or ER, after folding as ER resident proteins. The classical ER retention signal is the C-terminal KDEL (Lys-Asp-Glu-Leu) (SEQ ID NO: 38) sequence.

The term "antigenic epitope", "epitope", or "antigenic determinant" refers to the part of an antigen that is recognized and bound by the immune system, specifically by antibodies, B cells, or T cells. The term "epitope peptide" or "antigenic epitope peptide" refers to the epitope or antigenic epitope in the form of a peptide.

The term "excipient" or "additive" when used herein is intended to indicate all substances in a pharmaceutical formulation which are not active ingredients such as, e.g., carriers (e.g., carrier DNA, plasmid, vector virus), binders, lubricants, thickeners, surface active agents, preservatives, emulsifiers, buffers, flavoring agents, or colorants.

The term "exogenous" refers to any material introduced from or produced outside an organism, cell, tissue or system. For example, the term "exogenous HLA protein" used herein refers to HLA protein from outside of the subject or patient and the 'exogenous HLA protein' may or may not be produced by the subject or patient's cell or tissue.

The term "endogenous" refers to any material from or produced inside an organism, cell, tissue or system.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

As used herein, "gene expression" refers to the process by which the genetic information in a gene, the sequence of DNA base pairs, is made into a functional gene product, such as protein or RNA. The basic process is that DNA is transcribed into RNA, which is then translated into protein.

The term "Human Leukocyte Antigen (HLA)" refers to a gene complex or system encoding the major histocompatibility complex (MHC) proteins in humans, which is also termed HLA protein" refers to the MHC proteins are cell surface proteins responsible for the regulation of the immune system in humans. The HLA gene complex resides on a 3 Mbp stretch within chromosome 6p21. HLA genes are highly polymorphic, which means they have many different alleles, allowing them to fine-tune the adaptive immune system. HLAs corresponding to MHC class I (A, B and C) present foreign antigens (e.g. viral antigens) from inside of the cell to T-lymphocytes. The HLA class I/antigenic peptide complexes can stimulate the cytotoxic T cells (also called CTLs), which in turn kill the target cells.

The term "HLA Class I protein" refers to human MHC Class I protein or molecule. MHC class I molecules are transmembrane proteins that consist of a single α-chain and associate with β2-microglobulin for proper folding and trafficking to the cell surface.

The term "immune cells" refers to the cells of the immune system which can be categorized as lymphocytes (T-cells, B-cells and NK cells), neutrophils, and monocytes/macrophages. These are all types of white blood cells.

The term "immune danger signal" refers to when tissue cells are distressed because of injury, infection and so on, they start to secrete or express on their surfaces molecules that signal "danger", or the components of invaded organism (e.g., virus DNA or RNA) are also sensitized as danger signals by the immune system.

The term "immunogen" refers to a specific type of antigen that is able to elicit an immune response.

The term "tumor microenvironment (TME)" or "immunosuppressive tumor microenvironment" refers to the environment around a tumor, including the surrounding blood vessels, immune cells, fibroblasts, signaling molecules and the extracellular matrix (ECM). The tumor and the surrounding microenvironment are closely related and interact constantly. Tumors can influence the microenvironment by releasing extracellular signals to suppress immune response, promoting tumor angiogenesis and inducing peripheral immune tolerance, while the immune cells in the microenvironment can affect the growth and evolution of cancerous cells.

Terms such as "increasing" or "enhancing" preferably relate to an increase or enhancement by about at least 5%, preferably at least 10%, preferably at least 20%, preferably at least 30%, more preferably at least 40%, more preferably at least 50%, even more preferably at least 80%, and most preferably at least 100%. These terms may also relate to circumstances, wherein at time zero there is no detectable signal for a certain compound or condition and at a particular time point later than time zero there is a detectable signal for a certain compound or condition.

The term "inducible promoter" refers to a nucleotide sequence which, when operably linked with a polynucleotide which encodes or specifies a gene product, causes the gene product to be produced in a cell substantially only when an inducer which corresponds to the promoter is present in the cell.

As used herein, the term "isolated" refers to a cell, protein, polypeptide, peptide, polynucleotide, vector, etc., that is removed from its natural environment (i.e. separated from at least one other component(s) with which it is naturally associated or found in nature).

Lentiviral vectors are a type of retrovirus that can infect both dividing and nondividing cells because their pre-integration complex (virus "shell") can get through the intact membrane of the nucleus of the target cell. Lentiviral vectors are derived from human immunodeficiency virus.

A "linker peptide" or "linker sequence" as used herein refers to is an amino acid sequence connecting two other amino acid sequences. For example, a part of the HLA class I protein may be connected with a part of a tumor-associated antigen sequence, e.g., an epitope sequence, via a linker sequence.

The term "loss of heterozygosity" or "LOH" refers to as the loss of one parent's contribution to the cell, can be caused by direct deletion, deletion due to unbalanced rearrangements, gene conversion, mitotic recombination, or loss of a chromosome (monosomy).

The term "major histocompatibility complex" or "MHC" refers to a set of genes that code for cell surface proteins essential for the acquired immune system to recognize foreign molecules in vertebrates, which in turn determines histocompatibility. The main function of MHC molecules is to bind to antigens derived from pathogens and display them on the cell surface for recognition by the appropriate T-cells. MHC molecules mediate interactions of leukocytes, also called white blood cells (WBCs), which are immune cells, with other leukocytes or with body cells. The MHC determines compatibility of donors for organ transplant, as well as one's susceptibility to an autoimmune disease via cross reacting immunization. The human MHC is also called the HLA (human leukocyte antigen) complex (often just the HLA). MHC is the tissue-antigen that allows the immune system (more specifically T cells) to bind to, recognize, and tolerate itself (auto-recognition). MHC is also the chaperone for intracellular peptides that are complexed with MHCs and presented to T cell receptors (TCRs) as potential foreign antigens. MHC interacts with TCR and its co-receptors to optimize binding conditions for the TCR-antigen interaction, in terms of antigen binding affinity and specificity, and signal transduction effectiveness.

The term "MHC class I protein" or "MHC class I molecule" refers to one of two primary classes of major histocompatibility complex (MHC) molecules or glycoproteins or proteins (the other being MHC class II) and are found on the cell surface of all nucleated cells in the bodies of vertebrates. MHC I proteins form a functional receptor on most nucleated cells of the body. Major histocompatibility complex (MHC) class I molecules are responsible for peptide epitope presentation to cytotoxic T cells. In humans, the human leukocyte antigen (HLA) system is a locus of genes that code for MHC class I and class II molecules. HLA-A, -B, and -C genes code for MHC class I (MHCI)

proteins. A peptide, typically 8-11 amino acids in length, will bind an MHCI molecule through interaction with a groove formed by two alpha helices positioned above an antiparallel beta sheet. Processing and presentation of peptide-MHC class I (pMHCI) molecules involve a series of sequential stages comprising: a) protease-mediated digestion of proteins; b) peptide transport into the endoplasmic reticulum (ER) mediated by the transporter associated with antigen processing (TAP); c) formation of pMHCI using newly synthesized MHCI molecules; and, d) transport of pMHCI to the cell surface. On the cell surface, pMHCI will interact with cytotoxic T cells via T cell receptors (TCRs). Following the intricate pMHCI-TCR interaction, identification of a non-self-antigen may result in cytotoxic T cell activation through a series of biochemical events mediated by associated enzymes, co-receptors, adaptor molecules, and transcription factors. An activated cytotoxic T cell will proliferate to produce a population of effector T cells expressing TCRs specific to the identified immunogenic peptide epitope. The amplification of T cells with TCR specificity to the identified non-self-epitope results in immune-mediated apoptosis of cells displaying the activating non-self-epitope.

The term "MHC protein" refers to the protein encoded by the MHC genes.

Immunosuppressive tumor microenvironment (TME). The ability of tumors to foster a tolerant microenvironment and the activation of a plethora of immunosuppressive mechanisms, which may act in concert to counteract effective immune responses, such as tumor-induced impairment of antigen presentation, the activation of negative costimulatory signals, and the elaboration of immunosuppressive factors.

The term "mutant" or "mutant type" refers to a strain, gene, or characteristic arising or resulting from an instance of mutation, which is generally an alteration of the DNA sequence of genome or chromosome of an organism.

The term "N-terminal signal peptide" refers to the signal peptide (usually 16-30 amino acids long) present at the N-terminus of the majority of newly synthesized proteins that are destined towards the secretory pathway. These proteins include those that reside either inside certain organelles (the endoplasmic reticulum, Golgi or endosomes), secreted from the cell, or inserted into most cellular membrane. Signal peptide function to prompt a cell to translocate the protein, usually to the cellular membrane.

The term "neoantigen" refers to newly formed antigens that have not been previously recognized by the immune system. Neoantigens can for example arise from altered tumor proteins formed as a result of tumor gene alterations, including point mutations, insertions/deletions, amplification/fusions, posttranslational modifications, or from viral proteins.

As used herein, "nucleic acid(s)" is interchangeable with the term "polynucleotide(s)" and generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations.

As used herein, the terms "nucleic acid encoding", "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

As used herein, the term "oncolytic virus" refers to a virus capable of selectively replicating in tumor cells (e.g. a proliferative cell such as a cancer cell) with the aim of slowing the growth and/or lysing said dividing cell, either in vitro or in vivo, while showing no or minimal replication in normal cells. Typically, an oncolytic virus contains a viral genome packaged into a viral particle (or virion) and is infectious (i.e. capable of infecting and entering into a host cell or subject). As used herein, this term encompasses DNA or RNA vector (depending on the virus in question) as well as viral particles generated thereof.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The term "one or more" refers to either one or a number above one (e.g. 2, 3, 4, 5, etc.).

The phrase "operably linked" or "operably connected" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide", "peptide" and "protein" refer to polymers of amino acid residues which comprise at least nine or more amino acids bonded via peptide bonds. The polymer can be linear, branched or cyclic and may comprise naturally occurring and/or amino acid analogs and it may be interrupted by non-amino acids. As a general indication, if the amino acid polymer is more than 50 amino acid residues, it is preferably referred to as a polypeptide or a protein whereas if it is 50 amino acids long or less, it is referred to as a "peptide".

The term "plasmid" refers to "extra" self-replicating genetic elements found in cells. Plasmids are used in genetic engineering to generate recombinant DNAs and as a mechanism to transfer genes between organisms.

Point mutation or substitution is a genetic mutation where a single nucleotide base is changed, inserted or deleted from a sequence of DNA or RNA.

The term "polyadenylation signal" or "polyadenylation signal sequence" or "polyadenotide signal" or "polyadenotide signal sequence" refers to the sequence motif recognized by the RNA cleavage complex, which varies between groups of eukaryotes. Most human polyadenylation signal contains the AAUAAA sequence.

As used herein, the terms "prevent" and "preventing" or "prevention" refer to prophylactic or preventive measures intended to inhibit undesirable physiological changes or the development of a disorder or condition. Preventing a disease or condition may comprise initiating the administration of T cells obtained according to a method provided herein at a time prior to the appearance or existence of the disease or condition (or a symptom thereof) such that the disease or condition, or its symptoms, pathological features, consequences, or adverse effects do not occur.

The term "promoter" refers to a DNA sequence recognized by the synthetic machinery of the cell, or introduced synthetic machinery, required to initiate the specific transcription of a polynucleotide sequence.

The term "receptor" as used herein refers to a molecule expressed on the surface of a cell, whereby said molecule is capable of binding a cellular ligand. A receptor-ligand binding as used herein is preferably capable of initializing or inhibiting biochemical pathways and/or signal cascades when the proper ligand is binding to the receptor.

The term "recombinant" refers to relating to or denoting an organism, cell, protein, genetic material, DNA, or RNA, formed using recombinant technology.

The term "recombinant DNA" refers to DNA or rDNA made by combining DNA from two or more sources. DNA fragments are cut out of their normal position in the chromosome using restriction enzymes (also called restriction endonucleases) and then inserted into other chromosomes or DNA molecules using enzymes called ligases.

The term "recombinant TCR" refers to TCR made through recombinant technology.

The term "replication capable" or "replication capable virus" as employed herein refers to a replication competent virus or a virus whose replication is dependent on a factor in the cancer cells, for example an upregulated factor.

The term "replication competent" or "replication competent virus" in the context of the present specification refers to a virus that possesses all the necessary machinery to replicate in cells in vitro and in vivo, i.e. without the assistance of a packaging cell line. A viral vector, for example deleted in at least the E1A region, capable of replicating in a complementary packaging cell line is not a replication competent virus in the present context.

The term "replication defective" or "replication defective virus" in the context of the present specification refers to a virus that requires a packaging cell line (comprising a transgene) to replicate.

The term "retroviral vector" refers to proviral sequences that can accommodate the gene of interest, to allow incorporation of both into the target cells. The vector may also contain viral and cellular gene promoters, such as the CMV promoter, to enhance expression of the gene of interest in the target cells.

The term "self-cleaving linker peptide" refers to a short peptide (e.g., 18-22 amino acids-long peptides) present in a protein (e.g., recombinant protein) which can trigger the self-cleaving of a protein in cell. The cleavage commences after the protein translation. The exact molecular mechanism of self-cleaving linker peptide is still uncertain. However, it is believed to involve ribosomal "skipping" of glycyl-prolyl peptide bond formation rather than true proteolytic cleavage.

Self-inactivating lentiviral vectors have been used to introduce genes into mature T cells to generate immunity to cancer through the delivery of chimeric antigen receptors (CARs) or cloned T-cell receptors.

The term "self-protein" refers to protein normally produced by a particular organism. A particular organism's immune system should be tolerant to self-proteins; if not, there is autoimmunity.

As used herein, the term "silencer" refers to a DNA sequence capable of binding transcription regulation factor, called repressors. DNA contains genes that provide the template to produce messenger RNA (mRNA). That mRNA is then translated into proteins. When a repressor protein binds to the silencer region of DNA, RNA polymerase is prevented from transcribing the RNA sequence into RNA. With transcription blocked, the translation of RNA into proteins is impossible. Thus, silencers prevent genes from being expressed as proteins.

The term "solid tumor" refers to abnormal mass of tissue or tumor that usually does not contain cysts or liquid areas. Solid tumors may be benign (not cancerous), or malignant (cancerous).

As used herein, the terms "subject" or "patient" are used interchangeably and can encompass any vertebrate including, without limitation, humans, mammals, reptiles, amphibians, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having a disease or condition such as cancer.

The term "suicide gene" refers to a gene coding for a protein able to convert a precursor of a drug into a cytotoxic compound. Suicide genes comprise but are not limited to genes coding protein having a cytosine deaminase activity, a thymidine kinase activity, an uracil phosphoribosyl transferase activity, a purine nucleoside phosphorylase activity and a thymidylate kinase activity. Examples of suicide genes and corresponding precursors of a drug comprising one nucleobase moiety are disclosed in the following table The term "surface expression" refers to the fusion of the protein of interest to a natural surface protein of the host cell. This results in the recombinant protein being transported to and subsequently displayed on the surface of the host.

The term "T cell" refers to a type of lymphocyte which develops in the thymus gland (hence the name) and plays a central role in the immune response. T cells can be distinguished from other lymphocytes by the presence of a T-cell receptor on the cell surface. Cytotoxic T cells or CD8+ T cells or killer cells" are able to directly kill virus-infected cells as well as cancer cells. CD8+ T cells are also able to utilize small signaling proteins, known as cytokines, to recruit other cells when mounting an immune response. Helper T cells or CD4+ T cells function by indirectly killing cells identified as foreign: they determine if and how other parts of the immune system respond to a specific, perceived threat.

The phrase "tandem" refers to the spatial relationship between two or more entities (e.g. polynucleotide such as DNA and polypeptide) are arranged in such a way that they are placed one behind another.

The term "target" as used herein refers to a molecule, such as a protein or peptide, cells, or tissues, or organisms against which an immune response is to be directed.

The term "target antigen" refers to any substance against which it is desirable to generate an immune response but generally, the target antigen is a protein or peptide. A target antigen may comprise a full-length protein or a fragment thereof that induces an immune response (i.e., an immunogenic fragment). A target antigen or fragment thereof may be modified, e.g., to reduce one or more biological activities of the target antigen or to enhance its immunogenicity.

The term "target cell" refers to any cell against which it is desirable to generate an immune response, or can be specifically recognized by an immune cells e.g. T cells.

The term "T-cell Receptor" or "TCR" as used herein refers to molecule found on the surface of T cells, or T lymphocytes, that is responsible for recognizing fragments of antigen as peptide bound to major histocompatibility complex (MHC) molecules.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), The Encyclopedia of Molecular Biology, published by Blackwell Science Ltd., 1994; and Robert A. Meyers (ed.), Molecular Biology and Biotechnology: a Comprehensive Desk Reference, published by VCH Publishers, Inc., 1995; and other similar references.

The term "therapeutic" as used herein means a treatment. A therapeutic effect is obtained by reduction, suppression, remission, alleviation, preventing or eradication of a disease state.

As used herein, the term "therapeutically effective dose" or "therapeutically effective amount" or "effective amount" or "effective dosage" refers to the amount which—alone or in combination with further dosages—results in a desired reaction or a desired effect. In the case of the therapy of a particular disease or a particular condition, the desired reaction relates to the inhibition of the progress of the disease. This may comprise the deceleration of the progress of the disease, in particular a disruption of the progression of the disease. The desired reaction for a therapy of a disease or a condition may also be the retardation of the occurrence or the inhibition of the occurrence of the disease or the condition. An effective amount of the composition according to the present invention is dependent on the condition or disease, the severity of the disease, the individual parameters of the patient, including age, physiological condition, height, and weight, the duration of the treatment, the type of an optionally accompanying therapy, the specific administration route, and similar factors. In case the reaction of a patient is insufficient with an initial dosage, multiple dosages or higher dosages (or higher effective dosages which may be achieved by a more localized administration route) may be applied.

The terms "treatment" (and any form of treatment such as "treat", "treating") refer to both therapeutic and prophylactic or preventive measures, where the objective is to prevent or slow down (lessen) an undesired physiological change or pathological disorder. Treating a cancer may include, without limitation, alleviating one or more clinical indications, decreasing tumor growth or tumor cell proliferation, reducing the severity of one or more clinical indications of a cancer condition, diminishing the extent of the condition, stabilizing the subject's disease state (i.e., not worsening), delay or slowing, halting, or reversing cancer progression, and bringing about partial or complete remission. Treating cancer also includes prolonging survival by days, weeks, months, or years as compared to prognosis if treated according to standard medical practice not incorporating T cells obtained according to a method provided herein. Subjects in need of treatment can include those already having or diagnosed with cancer, as well as those prone to, likely to develop, or suspected of having cancer (e.g., lymphoma or multiple myeloma) or an infection.

The term "tumor" refers to neoplastic cell growth and proliferation, whether malignant or benign, and all precancerous and cancerous cells and tissues.

The term "tumor antigen" refers to an antigenic substance produced in tumor cells, i.e., it triggers an immune response in the host. Tumor antigens are useful tumor markers in identifying tumor cells with diagnostic tests and are potential candidates for use in cancer therapy.

The term "tumor-associated antigen" refers to antigens that are present on some tumor cells and also on some normal cells.

"Tumor infiltrating lymphocyte (TIL)" refers to a subject's own naturally occurring T cells that have already infiltrated the subject's tumors. It can be harvested, activated, expanded and re-introduced, e.g., re-infused, into the subject, where they can seek out and destroy tumors as a part of cancer or tumor treatment.

The term "tumor specific antigen" refers to antigens that are present on tumor cells and not on any other cells.

The term "vector" refers to a nucleic acid molecule capable of transporting another nucleic acid to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

The term "viral vector" is defined as virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Cur. Opin. Biotechnol. 5:434-439 and Ying, et al. (1999) Nat. Med. 5(7):823-827.

The term "vp/day" refers to viral particle per day

The term "wild" or "wildtype" refers to a strain, gene, or characteristic which prevails in natural conditions, as distinct from an atypical mutant type.

EXAMPLES

The following examples further illustrate the invention but, of course, should not be construed as in any way limiting its scope. Unless otherwise specified, the experimental methods used in the following examples are performed using the experimental procedures, operations, materials, and conditions that are understood and routinely performed by technical personals in the art. For instance, the recombinant plasmids and viral vectors, or polypeptides and proteins can be recombinantly produced using the nucleic acids described herein using standard recombinant methods (Green and Sambrook, Molecular Cloning: A Laboratory Manual, 4th ed., Cold Spring Harbor Press, Cold Spring Harbor, NY, 2012).

The following materials and methods were employed for the experiments described in Examples 1-5. The percentage concentration (%) of each agent is the volume percentage concentration (% (weight/volume)) of the agent, unless otherwise specified below.

Materials and Methods

1. Cell Lines:

The cell line used to prepare the lentiviral particles or used as target cell is 293T cells (ATCC CRL-3216). The presenting cell line for presenting antigenic peptides is T2 cells (174xCEM.T2, ATCC CRL-1992). The cell line for TCR gene expression and functional analysis is JRT cells (J.RT3-T3.5, ATCC® TIB-153). Tumor cell lines that are used as target cells include: human melanoma cell line A375 (ATCC CRL-1619), human fibrosarcoma cell line HT1080 (ATCC CCL-121), human ovarian cancer cell line SKOV3 (ATCC HTB-77), human lung cancer cell line H1299 (ATCC CRL-5803), human osteosarcoma cell line HOS-C1 (ATCC CRL-1547), human lung cancer cell line A549 (ATCC CCL-185). The SKOV3 cell line expressing NY-ESO-1 protein or the mutant KRAS protein with G12D point mutation was generated by transfecting SKOV3 cells with the pCDNA3.3 plasmid (Thermo Fisher K830001) encoding NY-ESO-1 protein (pCDNA3.3-NY) or KRAS G12D protein (pCDNA3.3-kras/g12d) and selected with 500 µg/mL of geneticin (Thermo Fisher 10131027). NY-ESO-1 (or CTAG-1B) is a well-known cancer-testis antigen (CTAs) with over-expression in numerous cancer types. The method to make pCDNA3.3-NY is described below.

2. Cell Culture Medium:

293T cells are cultured in Dulbecco's Modified Eagle Medium (DMEM) with higher glucose (VWR cat #VWRL0101-0500) supplemented with 10% Fetal Bovine Serum, 2 mM L-glutamine. The other cells lines are cultured in RPMI-1640 complete medium (Lonza, cat #12-115F) supplemented with Fetal Bovine Serum (ATCC 30-2020), 2 mmol/L L-glutamic acid, 1× Essential Amino Acids 50× (Invitrogen 11130-051), 1× Streptomycin/Penicillin 100× (Invitrogen 15140-122), 1x Sodium pyruvate 100× (Invitrogen 11360-070), and 1×2-mercaptoethanol 1000× (Thermo fisher 21985023).

3. Peripheral Blood:

The human peripheral blood products of the healthy donors were from Stanford Blood Center. The peripheral blood mononuclear cells (PBMCs) were generated from the residual leukocytes via pheresis (LRS chamber, product code A1012) with the Ficoll-Paque PLUS density gradient media (GE healthcare17144002) according to manufacturer's instruction.

4. Preparation of Target Cells Expressing Exogenous Proteins:

293T cells or the tumor cells are transfected with Lipofectamine 3000 (Thermo Fisher L3000015) according to manufacturer's instructions. The expression plasmids include the plasmids encoding the said labelling polypeptide, the exogenous HLA protein, or the amino acid sequences described in the present disclosure. The methods to make the plasmids are described below. If the plasmids containing the adenovirus genome are used to transfect 293T cells, the plasmids are pre-digested with PacI enzyme (New England Biolabs, R0547S) in order to release the adenovirus genome. The cells that transiently express the exogenous protein can be used as target cells 48-72 hours after transfection. To generate the stable SKOV3 cell line expressing NY-ESO-1 protein or the mutant KRAS protein with G12D point mutation, SKOV3 cells are cultured with the medium supplemented 500 µg/mL of geneticin 72 hours after transfection with the plasmid encoding the respective protein.

5. Preparation of the T Cells Expressing the Recombinant TCR:

To generate activated human T cells for expressing the TCR, the PBMC cells in 24-well plate were cultured with RPMI-1640 complete medium supplemented with 2 µg/ml of anti-human CD3 antibody (Biolegend 317303) and 2 µg/ml of anti-human CD28 antibody (Biolegend 302914) for 24 hours or the PBMC are treated with the human T-CD3/CD8 magnetic beads (Thermo Fisher 11131D) according to manufacturer's instructions. After 24 hours, the cells are cultured with RPMI-1640 complete medium supplemented with IL-2 100 IU/ml, IL-7 5 ng/ml, IL-15 5 ng/ml. To generate T cell line for expressing the TCR, the JRT (J.RT3-T3.5) cells that are a beta-chain-deficient mutant derived from a Jurkat cell line are cultured with RPMI-1640 complete medium. To infect the T cells with the lentivirus encoding the said TCR, the activated PBMC or the JRT cells were resuspended with 1 ml of freshly-made lentiviral supernatant in 24-well plate, and Polybrene (Santa Cruz Biotechnology sc-134220) was added at a final concentration of 5-8 µg/ml. The cells were centrifuged at 1000 g and 32° C. for 2 hours. After 6 hours, the medium was changed to RPMI-1640 complete medium supplemented with IL-2 100 IU/ml, IL-7 5 ng/ml, IL-15 5 ng/ml. The cells could also be transfected by using a RetroNectin Dish (RetroNectin Pre-coated Dish, 35 mmq) (Takara T110A) according to the manufacturer's instructions.

6. Cell Phenotype Analysis by Flow Cytometry:

To analyze the expression of TCR by PBMC or JRT cells transfected with lentiviruses encoding the exogenous TCR, the cells are resuspended in DPBS buffer (2.7 mM KCl, 1.5 mM KH2PO4, 136.9 mM NaCl, 8.9 mM Na2HPO4·7H2O, pH 7.4) with 1% FBS and stained with APC labeled anti-human CD8 antibody (Biolegend 300912) and the iTag Tetramer/PE-HLA-A*02:01 NY-ESO-1 (SLLMWITQC (SEQ ID NO: 2)) (MBL International TB-M011-1). The flow cytometer is a MACSQuant Analyzer 10 (Miltenyi Biotec Corporation), and the results are analyzed by Flowjo software (Flowjo Corporation). To analyze the expression of HLA-A2 by 293T cells transfected with the plasmids encoding HLA-A2 protein, the cells are stained with FITC anti-human HLA-A2 Antibody (Biolegend 343303) and analyzed by flow cytometry.

7. T Cell Functional Analysis:

To assess the specificity and function of the TCR expressed by JRT cells, CD69 expression after antigen stimulation was evaluated by flow cytometry according to the method in the art (Cytometry. 1996; 26(4):305-10). Briefly, in the duplicated wells of 96-well plate, TCR-gene modified JRT cells are co-cultured with the target cells for 16 hours, for example, mixed culture with T2 cells pulsed with antigenic peptide at different concentrations, 293T cells or tumor cells transduced with the nucleic acids described in the present disclosure. The cells are stained with anti-CD69 antibody (Biolegend 310905) and CD69+ JRT cell frequency is analyzed by flow cytometry according to the manufacturer's instructions. To assess the specificity and function of the TCR that was transduced into PBMCs, secretion of IFN-gamma by specific T cells after antigen stimulation was measured by an IFN-gamma ELISA (enzyme-linked immunosorbent assay). Briefly, in the duplicated or tripled wells of 96-well plate, TCR-gene modified PBMCs are co-cultured with the target cells described above, The cell supernatants are collected in 18-24 hours for IFN-gamma ELISA assays by using the IFN-gamma ELISA Read-Set-Go kit (eBioscience 88-7316) or human IFN-gamma DuoSet ELISA kit (R&D Systems DY285B) according to the manufacturer's instructions.

8. Preparation of the Recombinant TCR Lentiviral Vector:

The said TCR genes were cloned into a replication defective lentiviral vector pCDH-EF1α-MCS-PGK-GFP (System Biosciences CD811A-1). The vector pCDH-EF1α-MCS without GFP was generated by removing the PGK promoter and the GFP gene on the vector pCDH-EF1α-MCS-PGK-GFP. The sequences of the TCR-alpha-V-D-J regions and TCR-beta-V-D-J regions specific to NY-ESO-1 157-165 epitope peptide in the context of HLA-A*02:01 were determined according to the sequences described in reference disclosures U.S. Pat. No. 8,143,376B2 (denoted as TCR-NY-LY), WO2018099402A1 (denoted as TCR-NY-LI), or the reference literature J Immunol 2010; 184 (9), 4936-46 (denoted as TCR-NY-AE). The sequences of the TCR-alpha-V-D-J regions and TCR-beta-V-D-J regions specific to KRAS: G12D 10-18 peptide in the context of HLA-C*08:0 2 is determined according to the sequences described in reference disclosures WO2018026691 (denoted as TCR-RAS G12D). The sequences of mouse TCR-alpha constant chain and mouse TCR-beta constant chain are determined according to the reference sequences (GeneBank KU254562 and EF154514.1 respectively). The nucleic acids that comprise a TCR β chain with the mouse TCR-beta constant chain, a TCR α chain with the mouse TCR-alpha constant chain and a linker nucleic acid encoding a furin enzyme cleavage peptides, and a F2A peptide between the TCR alpha and beta chains and are shown in SEQ ID NOs: 30, 31, 32 or 33 and were synthesized by Integrated DNA Technologies or LifeSct LLC. The synthesized nucleic acids were cloned into the multi-cloning site downstream of the EF-1α promoter of the lentiviral vector pCDH-EF1α-MCS-PGK-GFP or pCDH-EF1α-MCS without GFP according to the manufacturer's instructions. The lentiviral vector expressing a TCR against NY-ESO-1 157-165 epitope was denoted as pCDH-EF1α-TCR-NY. The inserted nucleic acids are sequenced, and no errors and mutations are found. The lentiviral vector plasmids were transformed into the competent bacteria stellar (Takara Bio, 636763) to prepare plasmid stocks for making lentivirus particles.

9. Preparation of the Recombinant TCR Lentivirus Particles:

TCR lentivirus particles are generated from 293T or 293FT cells (Thermo Fisher R70007) that were transfected with lentiviral vector plasmids containing the said TCR gene. Briefly, 293T or 293FT cells growing in 6-well plate were co-transfected with the TCR lentiviral vector plasmid and the pPACKH1-lentivector packaging kit (System Biosciences LV500A-1) by using Lipofectaine 3000 transfection reagent (invitrogen, 11668019) according to the manufacturer's instructions. After 48 hours of culture, the supernatant was harvested and filtered through a 0.4 µm filter membrane. The virus supernatant was concentrated with Lenti-X™ Concentrator (Takara, 631231) according to the manufacturer's instructions. The fresh made TCR-lentivirus was used to infect JRT cells or the activated PBMC.

10. Preparation of the Expression Vector Encoding NY-ESO-1 Protein or the Mutant KRAS G12D Protein:

Total RNA that is purified from HT1080 cells (NY-ESO-1+, KRAS wild-type) with the PureLink™ RNA Mini Kit (Thermo Fisher 12183020) according to the manufacturer's instructions is used as a template to generates RT-PCR products with PrimeScript™ RT-PCR Kit (Takara RR014A). The NY-ESO-1 full length gene is generated by PCR with the primer pair: 5'-TATATAAGCAGAGCTGCCAC-CATGCAGGCCGAAGGCCGGGGCA-3' as shown in SEQ ID NO: 39 and 5'-TGATTGTCGACGCCCT-TAGCGCCTCTGCCCTGAGGGAGGCTG-3' as shown in SEQ ID NO: 40. The KRAS G12D full length gene is generated by PCR with the primer pair: 5'-ATGACT-GAATATAAACTTGTGGTAGTTG-GAGCTGACGGCGTAGGCAAGAGTGC CTTG-3' as shown in SEQ ID NO: 41 and 5'-TGATTGTCGACGCCCT-TACATAATTACACACTTTGTCTTTGACTTC-3' as shown in SEQ ID NO: 42. The resulting gene is cloned into the TOPO-cloning site of pCDNA3.3 vector (Thermo Fisher K830001) according to the manufacturer's instructions. The PCRs described in the present disclosure are performed with the NEBNext® High-Fidelity 2× PCR Master Mix (New England Biolabs M0541L) according to the manufacturer's instructions.

11. Preparation of Replication-Defective Recombinant Adenovirus Plasmid Encoding the Said Labelling Polypeptide and/or the Exogenous HLA Class I Molecule:

The replication-defective recombinant adenovirus system described in the present disclosure is based on the AdEasy system (Nature Protocols 2007; 2:1236-1247). The nucleic acids of the EF1α promoter are cloned from the pCDH-EF1α-MCS-PGK-GFP plasmid (System Biosciences, CD811A-1) by PCR with the primer pair: 5'-CTCAT-AGCGCGTAATGGCTCCGGTGCCCGTCAGTGGGCAG-3' as shown in SEQ ID NO: 43 and 5'-GAAT-TCGCTAGCTCTAGATCACGACACCTGAAATGGAAG-3' as shown in SEQ ID NO: 44 and are integrated into the pShuttle-CMV vector (Agilent technologies, cat #24007) to replace the CMV promoter to generate the pShuttle-EF1α vector. The cDNA encoding full length HLA-A*02:01 as shown in SEQ ID NO: 15 and the cDNA encoding human beta-2 microglobulin are generated from T2 cells and are cloned into the pcDNA3.3-TOPO vector according to the manufacturer's instructions. The nucleic acids encoding the labelling polypeptide comprising antigenic epitope peptide NY-ESO-1 157-165 as shown in SEQ ID NO: 22 and the nucleic acids encoding linker peptide as shown in SEQ ID NO: 36 are synthesized by the Integrated DNA Technologies. To make nucleic acids as shown in SEQ ID NO: 35 that encodes a labelling polypeptide that is connected a HLA-A*201 protein with a linker peptide, the procedure is as following: Using the synthesized nucleic acids encoding the labelling polypeptide as the template to perform a PCR with the primer pair 5'-AGAGCTAGCGAATTCAACAT-GAAAGGTTCCATCTTCAC-3' as shown in SEQ ID NO: 45 and 5'-ACACTGTGTAATCCACATCAATAGC-GATCTCTTTC-3' as SEQ ID NO: 46 to generate the nucleic acid segment encoding a labelling polypeptide with NY-ESO-1 157-165 (denoted as NY); Using the synthesized nucleic acids encoding linker peptide as the template to perform PCR with the primer pair: 5'-TGGATTA-CACAGTGTCGTCGTAAGCGATCCGGAAGCGGA-3' as shown in SEQ ID NO: 47 and 5'-CGCCATGACGGC-CATGGGCCCAGGGTTGGACTCGACGTC-3' as shown in SEQ ID NO: 48 to generate the nucleic acids encoding a linker peptide; and using the cDNA encoding full length HLA-A*02:01 to perform PCR with the primer pair: 5'-ATGGCCGTCATGGCGCCCCGA-3' as shown in SEQ ID NO: 49 and 5'-TCACACTTTACAAGCTGTGAGA-GACAC-3' as shown in SEQ ID NO: 50 to generate the HLA-A*201 gene (denoted as A2). Mix the above purified PCR products as the template to perform PCR with the primer pair: 5'-ATGAAAGGTTCCATCTTCACAT-TGTTTTTGTTC-3' as shown in SEQ ID NO: 51) and 5'-CGCCATGACGGC-CATGGGCCCAGGGTTGGACTCGACGTC-3' as shown in SEQ ID NO: 52 to generate the nucleic acids that encodes a labelling polypeptide that is connected an HLA-A*201 protein with a linker peptide. The resulting nucleic acids are cloned into the multiple cloning site of the pShuttle-EF1α vector to generate pShuttle-EF1α-NY-A2 with the conventional gene cloning technology in the art.

12. Preparation of Recombinant Adenovirus Plasmids

The pShuttle vectors are linearized with PmeI (NEB Biolabs, R0560s). After purification, the vector was transformed into the electrocompetent BJ5183-AD-1 bacterial strain (Agilent technologies, 200157) by delivering the pulse at 2,500 V, 200Ω and 25 μF in a Bio-Rad Gene pulser electroporator according to the manufacturer's instructions. The potential adenovirus recombinants are screened with PacI (NEB Biolabs R0547S) restriction digestion. The correct recombinants usually yield a large fragment (approximately 30 kb) and a smaller fragment of 3.0 or 4.5 kb.

13. Preparation of Conditionally Replication-Competent Adenovirus Plasmids Encoding the Said Labelling Polypeptide and/or the Exogenous HLA Class I Molecule:

To generate a pShuttle vector containing an adenovirus E1A and the nucleic acids encoding the said labelling polypeptide with a HLA molecule, both of which are driven by different exogenous promoters, the genomic DNA of the commercial oncolytic adenovirus (H101, Shanghai Three Dimensional Biotechnology) is used as a template to perform a PCR with the primer pair: 5'-GGAAGATCTGGACT-GAAAATGAG-3' as shown in SEQ ID NO: 53 and 5'-TGAGGTCAGATGTA ACCAAGATTA-3' as shown in SEQ ID NO: 54 to obtain E1A genomic DNA as shown in SEQ ID NO: 34. The resulted PCR fragment is purified and digested by BglII and then ligated to the BglII and EcoRV sites of the multiple cloning site on pShuttle-CMV vector (Agilent technologies 24007) to generate pShuttle-CMV-E1A-SV40polyA. To generate a pShuttle vector encoding a mutant E1A, for example an E1A with deletion of 24 nucleotides in E1A gene as shown in SEQ ID NO: 11, the pShuttle-CMV-E1A-SV40polyA plasmid is used as a template to perform the site-directed mutagenesis with the GeneArt Site-Directed Mutagenesis System (Thermo Fisher A13282). The resulting plasmid is denoted as pShuttle-CMV-E1A d 24-SV40polyA. With this plasmid as a template, PCR is performed with the primer pair: 5'-CGCGTCGACTACTGTAATAGTAATCAATTACG G-3' as shown in SEQ ID NO: 55 and 5'-GACGTCGACTAA-GATACATTGATGAGTTTGGAC-3' as shown in SEQ ID NO: 56. The resulting PCR segment is digested with SalI and cloned into the multiple cloning site of pShuttle-EF1α-NY-A2 vector to yield pShuttle-EF1α-NY-A2-CMV-E1A d 24. To generate a pShuttle vector containing an adenovirus E1A gene that is driven by an exogenous promoter and nucleic acids encoding a HLA molecule combined with the said labelling polypeptide or a HLA molecule combined with a beta-2 microglobulin that is driven by the native E1B promoter, the procedure is as following: Use the E1A genomic sequence encoding E1A protein contains a 24-base pair deletion (E1A 122-129 deletion) synthesized by Integrated DNA Technologies, as template to perform PCR with the primer pair: 5'-ATGAGACATATTATCTGCCACG-GAG-3' as shown in SEQ ID NO: 57 and 5'-CATGGTGGCGAGGTCAGATGTAAC-3' as shown in SEQ ID NO: 58 to obtain E1A d 24 sequence. The resulting E1A nucleic acid with 24-base pair deletion (denoted as E1A d 24) not only comprises the E1A coding region and the native E1A polyA signal sequence with E1A polyA adding site, but also comprise the native E1B promoter as shown in SEQ ID NO:10. A Kozak sequence is also introduced into the regulatory segment that drives the expression of downstream genes. Using the cDNA encoding full length HLA-A*02:01 or the cDNA encoding human beta-2 microglobulin as template to perform PCR, HLA-A*02:01 and beta-2 microglobulin gene segments were obtained. The synthesized mutant HLA-C*08:02 gene as shown in SEQ ID NO: 16 (denoted as C08), the synthesized nucleic acids encoding the labelling polypeptide containing NY-ESO-1 157-165 epitope peptides as shown in SEQ ID NO: 22 (denoted as NY) or containing KRAS: G12D 10-18 as shown in SEQ ID NO: 23 (denoted as RAS), or the synthesized nucleic acids encoding the linker peptide as shown in SEQ ID NO: 36 (dented as F2A) are used as template to perform PCR to obtain the respective gene segments. The combination of nucleic acid segments including E1A d 24-A2-F2A-NY, E1A d 24-008-F2A-RAS, E1A d 24-A2-F2A-BM and E1A d 24-008-F2A-BM were generated by using the In-Fusion HD Cloning Plus kit (Takara 638909) according to the manufacturer's instructions. The resulting gene combinations were cloned into downstream of EF1α promoter in a pShuttle-EF1α vector to generate pShuttle-EF1α-E1A d 24-A2-F2A-NY, pShuttle-EF1α-E1A d 24-008-F2A-RAS, pShuttle-EF1α-E1A d 24-008-F2A-BM, and pShuttle-EF1α-E1A d 24-A2-F2A-BM respectively. To generate recombinant adenovirus plasmids, the pShuttle vectors were linearized with PmeI and transformed into the electrocompetent BJ5183-AD-1 by delivering the pulse at 2,500 V, 200 S2 and 25 μF in a Bio-Rad Gene pulser electroporator as described above. The resulted recombinant adenovirus plasmids are denoted as pAd-EF1α-E1A Δ 24-A2-F2A-NY, pAd-EF1α-E1A-008-F2A d 24-RAS, pAd-EF1α-E1A d 24-008-F2A-BM, and pAd-EF1α-E1A d 24-A2-F2A-BM.

14. Preparation of the Recombinant Adenovirus Encoding the Said Labelling Polypeptide and/or the Exogenous HLA Class I Molecule:

The recombinant adenovirus plasmids are digested with Pac I (NEB Biolabs R0547S) to release the adenovirus genomic DNA. The linearized plasmids are purified with phenol/chloroform extraction and used to transfect ADENO-X 293 cells (Takara 632271) with Lipofectaine 3000 transfection reagent (Thermo Fisher L3000001) according to the instructions of the manufacturer. The transfected cells are maintained in the 37° C., 5% CO2 incubator for 14-20 days until cytopathic effect (CPE) can be observed. Four freeze-thaw-vortex cycles are performed to release adenoviruses from the cells and to obtain the viral particles. It usually takes two to four rounds of amplification to generate a large-scale preparation of high-titer viruses. The procedure for preparation of large-scale adenovirus follows the method described in the reference (Nat Protoc 2007; 2 (5), 1236-47). The adenovirus titer is determined by Adeno-X GoStix kit (Takara 632270) according to the manufacturer's instructions. To infect the target cell with the recombinant adenovirus, based on the defined MOI (multiplicity of infection) that refers to the number of infected viral particles per cell, the quantity of the virus titer and number of the target cells are determined. Usually the expression of the exogenous genes can be detected 3-4 days after infection.

Example 1

This example demonstrates that exogenous genes can be efficiently expressed by the gene constructs described in the present disclosure, including the adenoviral vectors that contain the nucleic acids encoding said labelling polypeptide and/or the exogenous HLA class I molecule; and the lentiviral vector that contains the nucleic acids encoding T cell receptor. FIG. 1A shows the schematic representations of the constructs described in the present disclosure. The pAdEasy-EF1α-NY-A2 is the replication-defective adenovirus vector that expresses the said labelling polypeptide containing NY-ESO-1 157-165 epitope peptide shown in SEQ ID NO: 13 and the HLA-A2 protein as shown in shown in SEQ ID NO: 5. The expression unit comprising nucleic acids encoding the labelling polypeptide and a HLA-A2 gene connected with a Furin-F2A linker is flanked with an exogenous EF-1α promoter and a SV40 poly(A) signal sequence. The pAd-EF1α-E1A-A2-F2A-NY is the conditionally replication-competent adenovirus vector that contains an HLA-A2 gene and nucleic acids encoding the said labelling polypeptide containing NY-ESO-1 157-165 epitope peptide. The pAd-EF1α-E1A-A2-F2A-BM is the conditionally replication-competent adenovirus vector that contains an HLA-A2 gene and a human beta-2 microglobulin gene. Both pAd-EF1a-E1Ad24-A2-F2A-NY and pAd-EF1α-E1Ad24-A2-F2A-BM constructs have a mutant E1A gene encoding the E1A protein containing a deletion of 24 residues as shown in SEQ ID NO:11 and are flanked by exogenous EF-1α promoters and native E1A poly(A) signal sequences. In these two conditionally replication-competent constructs, the E1B gene region is deleted and incorporate the nucleic acids encoding the labelling polypeptide and the other exogenous genes into this region and utilize the native E1B regulatory elements, including the native E1B promoter and E1B/IX poly(A) signal to drive the expression of the exogenous genes. FIG. 1B shows the schematic representing the lentiviral vectors pCDH-EF1α-TCR-NY-LY, pCDH-EF1α-TCR-NY-AE and pCDH-EF1α-TCR-NY-LI that contain various NY-ESO-1 specific TCR genes encoding the TCR polypeptides as shown in SEQ ID NO:26, 27 and 28 respectively. The constant regions of both the TCR beta chain and alpha chain are replaced with the murine TCR constant sequence. The TCR beta chain and alpha chain that are connected with a cleavable furin-F2A linker sequence are flanked by EF-1α promoters and the lentiviral postertranscriptional regulatory elements (WPRE).

To assess if the exogenous genes can be expressed by the recombinant constructs, HLA-A2 negative 293T cells were transduced with the pShuttle vectors containing the expression units EF1 α-NY-A2, EF1α-E1 Ad24-A2-F2A-NY, or EF1α-E1 Ad24-A2-F2A-BM that are flanked by stretches of genomic sequence homologous to type 5 adenovirus at each end. The cells were stained with anti-HLA-A2 antibody and the expression of HLA-A2 was assessed by flow cytometry. FIG. 1C shows that 293T cells that were transduced with all three constructs containing HLA-A2 gene could express HLA-A2, which demonstrate that the regulatory elements in the constructs were functional to drive the expression of exogenous polypeptide and HLA-A2 protein was released from the polypeptide by the cleavage at the furin-F2A linker. The fluorescence intensity of HLA-A2 expression on the 293T cells transduced with pShuttle-EF1 α-NY-A2 was lower than the intensity of 293T cells transduced with pShuttle-EF1α-E1Ad24-A2-F2A-NY and pShuttle-EF1α-E1Ad24-A2-F2A-BM, which suggested that the native E1B promoter and E1B poly (A) signal might be more efficient to drive the expression of exogenous genes in the context of adenovirus genome.

To assess if the TCR could be expressed by the recombinant lentivirus, the lentivirus expresses a NY-ESO-1 specific TCR that was prepared by transfecting 293T cells with pCDH-EF1α-TCR-NY vectors and utilized to infect JRT cells. The infected JRT cells were stained with anti-CD8 antibody and NY-ESO-1 157-165/HLA-A2 tetramer that can specifically bind to the TCRs that specifically recognize the NY-ESO-1 157-165 in the context of HLA-A2. FIG. 1D shows that JRT cells transduced with the lentiviruses express various TCRs were able to bind the NY-ESO-1 157-165/HLA-A2 tetramer, which demonstrated that the TCR alpha and beta chain were expressed by the recombinant lentivirus. In addition, the alpha and beta chains were separated by the cleavage at the furin-F2A linker and paired with murine constant region to form a TCR/CD3 complexes and expressed on the surface of JRT cells.

Example 2

This example demonstrates that once the labelling polypeptide and the exogenous HLA class I protein are expressed by the vector constructs described in the present disclosure, the antigenic epitope peptide can be released from the labelling polypeptide and presented by the exogenous HLA class I molecules to form an antigenic peptide/HLA class I complex that is recognized by the specific TCR.

To assess the ability of TCRs on the surface of JRT cells to specifically recognize the antigenic epitope peptides that are presented by the exogenous HLA class I molecules, JRT cells were transduced with the recombinant lentivirus that were generated from 293T cells co-transfected with pCDH-EF1α-TCR-NY-LY, pCDH-EF1α-TCR-NY-AE or pCDH-EF1α-TCR-NY-LI with the packaging vectors described above. The transfected JRT cells were cultured with T2 cells pulsed with 10× dilution series of NY-ESO-1 157-165 peptide starting from 1 ug/ml. After antigen stimulation for 16-24 hours, the percentages of CD69+ JRT cells were analyzed by flow cytometry. FIG. 2 A shows that the TCR-gene transduced JRT cells expressed CD69 after stimulation with the antigenic peptide, which demonstrated JRT cells were activated by the NY-ESO-1 157-165 peptide presented by HLA-A2 and the activation was a dose-dependent response. With regards to the sensitivity of the TCR against NY-ESO-1 157-165 epitope, TCR-NY-LY and TCR-NY-AE are comparable but TCR-NY-LI is about 10-fold less sensitive in response to NY-ESO-1 157-165 peptides.

JRT cells transduced with the TCR specific to NY-ESO-1 157-165 peptide were utilized as effector cells to assess the presentation of the antigenic peptide on surface of target cells. The target cells were HLA-A2 negative and NY-ESO-1 negative 293T cells transduced with pShuttle-EF1α-NY-A2 or pShuttle-EF1α-E1A d 24-A2-NY. 293T cells transduced with an empty pShuttle vector were used as the control. FIG. 2. B shows that 293T cells transduced with either pShuttle-EF1a-NY-A2 or pShuttle-EF1a-E1A d 24-A2-NY could activate JRT cells transduced with all three TCRs specific to NY-ESO-1 157-165 epitope. FIG. 2.B also shows that JRT cells transduced with all three NY-ESO-1 157-165 specific TCRs could be activated by 293T cells transduced with pShuttle vectors containing either EF1 α-NY-A2 or EF1α-E1Ad24-A2-F2A-NY. Compared to the control target 293T transduced with empty pShuttle vector, the percentages of CD69+ JRT cells were significantly increased in the group with the target 293T cells expressing the said labelling polypeptide and HLA-A2 (Student's t-Test, p<0.01). The results demonstrate that the labelling polypeptide and exogenous HLA-A2 were expressed in 293T cells. The NY-ESO-1 157-165 epitope specific TCRs on JRT cells could recognize NY-ESO-1 157-165 peptides that were released from the labelling polypeptide and presented by HLA-A2 on 293T cell surface. In the group with JRT cells expressing TCR-NY-LY and TCR-NY-AE as effectors, the target 293T cells transduced with pShuttle-EF1α-E1 Ad24-A2-F2A-NY were able to induce a significantly high percentage of CD69+ JRT cells, comparing to the target 293T cells transduced with pShuttle-EF1 α-NY-A2 (Student's t-Test, p<0.05). This result was correlated to the higher expression of HLA-A2 on 293T cells transduced with pShuttle-EF1α-E1Ad24-A2-F2A-NY, which suggested that the native E1B promoter and E1B poly (A) signal could efficiently drive the expression of exogenous genes when the expression unit was flanked by adenovirus genomic DNA.

To assess the function of the exogenous HLA class I molecule that were expressed by the gene constructs described in the present disclosure to present the antigenic epitope peptides that were derived from endogenous antigenic proteins, 293T cells were co-transduced with pCDNA3.3-NY and pShuttle-EF1a-E1A d 24-A2-F2A-BM and utilized as target cells. pCDNA3.3-NY encodes a full-length NY-ESO-1 protein and makes 293T cells express NY-ESO-1 protein as an endogenous tumor antigen to yield the NY-ESO-1 157-165 epitope peptides. If the NY-ESO-1 antigen was processed through HLA class I antigen processing pathway and the NY-ESO-1 157-165 peptides were presented by the exogenous HLA-A2, the target cells could be recognized by the TCRs expressed by JRT cells. 293T cells transduced with either pCDNA3.3-NY or pShuttle-EF1a-E1A d 24-A2-F2A-BM alone were set as negative control targets. FIG. 2.C shows that 293T cells transduced with pShuttle-EF1a-E1A d 24-A2-F2A-BM alone could not activate the NY-ESO-1 specific TCRs expressed by JRT cells. However, when the target cells were pulsed with NY-ESO-1 157-165 peptide at 1 ug/ml, a large percentage of JRT cells with various TCRs could be induced to express CD69, which demonstrated that the exogenous HLA-A2 was expressed by the target cells and could present the antigenic peptide for the activation of T cells. Moreover, when the target cells express both NY-ESO-1 protein and HLA-A2 molecule, they could induce a significant percentage of CD69+ JRT cells in mixed culture with JRT cells transduced with NY-ESO-1 specific TCRs, compared to the negative control targets (Student's t-Test, p<0.05). This result demonstrated that NY-ESO-1 157-165 epitope peptide could be generated through endogenous HLA class I processing machinery and presented by exogenous HLA-A2. This also provides evidence that exogenous HLA class I molecule can be introduced into target cells as an allogeneic HLA to present the antigenic epitope peptides derived from endogenous proteins such as overexpressed tumor-associated antigens or neoantigens that are generated from the mutant proteins.

To further assess if the nucleic acids encoding the labelling polypeptide and/or HLA class I molecule within the frame of adenovirus genomic DNA could express the exogenous polypeptide and protein, the adenovirus vector pAd-EF1a-E1A d 24-A2-NY was digested with PacI to obtain adenovirus genomic DNA containing the nucleic acids encoding HLA-A2 protein and the labelling polypeptide with NY-ESO-1 157-165 epitope. pAd-EF1a-E1A d 24-A2-BM vector was also digested with PacI to obtain adenovirus genomic DNA that expresses exogenous HLA-A2 and beta2-microglobulin proteins. 293T cells were transfected with the adenovirus DNA derived from pAd-EF1a-E1A d 24-A2-NY and pAd-EF1a-E1A d 24-A2-BM and utilized as target cells 48 hours after transfection to stimulate JRT cells transduced with NY-ESO-1 specific TCRs, including JRT-TCR-NY-LY and JRT-TCR-NY-AE. FIG. 2. D shows that exogenous HLA-A2 was expressed by pAd-EF1a-E1A d24-A2-BM in 293T cells and was not only able to present the NY-ESO-1 157-165 peptide exogenously pulsed at 1 ug/ml in vitro, but was also able to present the NY-ESO-1 157-165 peptide derived from NY-ESO-1 protein that was introduced into 293T cells by the co-transfected pCDNA3.3-NY. JRT cells with NY-ESO-1 specific TCRs were activated by the NY-ESO-1 157-165 peptide/HLA-A2 complexes on target cells to express CD69 and the percentage of CD69+ JRT cells significantly increased compared to the control target cells transduced with pAd-EF1a-E1A d24-A2-BM alone (Student's t-Test, p<0.01). 293T cells transduced with the adenovirus DNA derived from pAd-EF1a-E1A d24-A2-NY that express both labelling polypeptide with NY-ESO-1 157-165 epitope and exogenous HLA-A2 could also activate the JRT cells with NY-ESO-1 specific TCRs. Compared to the target cells co-transduced with pCDNA3.3-NY/pAd-EF1a-E1A d24-A2-BM, the target cells transduced with pAd-EF1a-E1A d24-A2-NY activated a similar percentage of CD69+ JRT-TCR-NY-LY cells. Although more JRT-TCR-NY-AE cells were activated by the target cells with pAd-EF1a-E1A d24-A2-NY, there was no significant difference between the two target cells. These results demonstrated that if the HLA class I antigen processing and presentation machinery is intact in 293T cells, the antigenic epitope peptide can be generated from the endogenous proteins and presented efficiently by the exogenous HLA class I molecules that were introduced into cells by the vectors described in the present disclosure.

Example 3

This example demonstrates that the antigenic epitope peptide could be presented by the exogenous HLA class I molecule in tumor cells when tumor cells are transduced with the gene constructs containing the nucleic acid encoding the said labelling polypeptide and HLA class I protein as described in the present disclosure. The expression of the labelling polypeptide and exogenous HLA class I molecule sensitizes the tumor cells to be targets recognized by the specific TCR, no matter whether or not the tumor cells endogenously express the specific antigen or the HLA class I allele that presents the antigenic epitopes to the specific TCR. In addition, the expression of exogenous HLA class I protein in tumor cells made the tumor cells allogeneic, but more importantly, the exogenous HLA class I molecules could present the epitope peptide derived from endogenous antigenic proteins and activate the TCRs that specifically recognize the epitope in the context of a particular HLA class I allele.

A375 is a human melanoma cell line and represents the HLA-A2+ and NY-ESO-1+ tumor cells. SKOV3 is a human ovarian cancer cell line and represents the HLA-A2−, NY-ESO-1− double negative tumor cells. SKOV3 cells transduced with pCDNA3.3-NY and stably express NY-ESO-1 protein represent the HLA-A2 negative and NY-ESO-1 positive tumor cells. The tumor cells were transduced with pShuttle-EF1a-E1A d24-A2-NY or pShuttle-EF1a-E1A d24-A2-BM and were utilized as target cells to culture with JRT cells with NY-ESO-1 specific TCRs. The percentage of CD69+ cells represents the ability of the target cells to activate the TCRs on JRT cells.

FIG. 3. shows that both JRT-TCR-NY-LY and JRT-TCR-NY-AE can be activated by A375 cells, which demonstrated that NY-ESO-1 157-165 epitope peptide could be generated from the endogenous NY-ESO-1 protein and presented by its own HLA-A2 molecule. A375 cell transduced with pShuttle-EF1a-E1A d24-A2-BM could not significantly increase its sensitivity to be recognized by the specific TCRs although more HLA-A2 expressed in the cells, which suggested that the number of NY-ESO-1 157-165 peptide/HLA-A2 complexes presented on A375 cells was not limited by the quantity of HLA-A2 but the quantity of the NY-ESO-1 157-165 peptide processed by the HLA class I antigen processing machinery. The expression of TAP proteins in A375 was deficiently reduced as reported in a study (J Invest Dermatol, 2008; 128 (8), 1991-6), which supports this hypothesis. Comparing to the control A375 cells, A375 cells transduced with pShuttle-EF1a-E1A d24-A2-NY significantly increase the percentage of CD69+ JRT-TCR-NY-LY cells (Student's t-Test, p<0.05), which demonstrated that the said labelling polypeptide could circumvent the transporter associated with antigen processing (TAP) and deliver the antigenic peptide into the lumen of the endoplasmic reticulum (ER), where these peptides are loaded onto HLA class I molecules. The NY-ESO-1–/HLA-A2– double negative SKOV3 cells and the NY-ESO-1–/HLA-A2+ SKOV3 cells that were transduced with pShuttle-EF1a-E1A d24-A2-BM were not able to activate JRT-TCR-NY-LY and JRT-TCR-NY-AE as expected. pShuttle-EF1a-E1A d24-A2-NY could sensitize SKOV3 cells to be recognized by the NY-ESO-1 specific TCRs on JRT cells (Student's t-Test, p<0.01), which demonstrated that the said labelling polypeptide comprising an antigenic epitope combined with a HLA class I molecule that is able present the antigenic epitope peptide could universally sensitize tumor cells to be recognized by a specific TCR, regardless of the expression status of endogenous antigen or the matched HLA class I allele. SKOV3-NY cells transduced with pShuttle-EF1a-E1A d24-A2-BM could activate the NY-ESO-1 specific TCRs on JRT cells, which demonstrated that the exogenous HLA class I molecule that was introduced into tumor cells could sensitize the tumor cells to be recognized by the specific TCR provided that the tumor cells expressed the tumor antigen as the resource to generate the antigenic peptide. An intact antigen processing and presentation machinery in tumor cells is also required in order to process the antigenic epitope peptide for the presentation by the exogenous HLA class I molecule. More JRT-TCR-NY-LY cells were activated by the target cells SKOV3-NY-pShutlle-A2-F2A-NY than by the target cells SKOV3-NY-pShutlle-A2-F2A-BM (Student's t-Test, p<0.05), because more NY-ESO-1 157-165 peptides might be generated from both endogenous NY-ESO-1 protein and the labelling polypeptide.

Example 4

This example demonstrates that that tumor cells transduced with the nucleic acids encoding the said labelling polypeptide and/or exogenous HLA class I molecule can be sensitized to be recognized by the primary T cells that are transduced to express a specific TCR.

HLA-A2 negative PBMCs were transfected with the recombinant lentivirus that express the NY-ESO-1 specific TCR, including TCR-NY-LY, TCR-NY-AE or TCR-NY-LI. 7-10 days after transfection, the PBMCs were stained with anti-CD8-APC and NY-ESO-1 157-165 tetramer-PE. FIG. 4A shows that T cells transduced with all three TCR genes could express the NY-ESO-1 157-165 specific TCRs that were labelled by NY-ESO-1 157-165 tetramers. NY-ESO-1 157-165 tetramer positive cells were observed in both CD8+ and CD8– cell population. While the CD8+ cells were NY-ESO-1 specific CTLs, the CD8– cells were most likely CD4+ helper T cells that were transduced to express NY-ESO-1 specific TCR. This result demonstrated that the TCRs TCR-NY-LY, TCR-NY-AE and TCR-NY-LI had high binding affinity with the NY-ESO-1 157-165/HLA-A2 complexes and are independent of CD8 for the TCR-pMHC binding. The high-affinity TCRs are considered suitable for the development of adoptive T cell therapy against cancer (J Clin Invest 2019; 129 (1), 69-71). These PBMCs expressing NY-ESO-1 specific TCRs were utilized as effector cells to assess the sensitivity of tumor cells transduced to express the said labelling polypeptide and exogenous HLA class I molecule.

A375 cell line, SKOV3 cell line, and SKV3-NY cells that express full-length NY-ESO-1 proteins represent the tumor cells with NY-ESO-1 and HLA-A2 double positive, NY-ESO-1 and HLA-A2 double negative and NY-ESO-1 positive alone respectively. These cell lines were transduced with pShuttle-EF1a-E1A d24-A2-NY or pShuttle-EF1a-E1A d24-A2-BM and utilized as target cells to assess the function of the said labelling polypeptide and the exogenous HLA-A2 to sensitize tumor cells to be recognized by the specific TCRs expressed on primary T cells. PBMC transfected with the recombinant lentivirus were incubated with the target cells for 16-24 hours with a 10:1 E:T ratio. The secretion of IFN-gamma in the supernatant was assessed to evaluate the activation of T cells by the stimulation of target cells. FIG. 4B shows that all target cell lines transduced with pShuttle-EF1a-E1A d24-A2-BM could efficiently present the pulsed NY-ESO-1 156-165 peptide at 1 ug/ml to activate the TCRs expressed by T cells, which demonstrated that the exogenous HLA-A2 protein was expressed by the pShuttle-EF1a-E1A d24-A2-BM vector in various target cells and the NY-ESO-1 156-165/HLA-A2 complexes could be recognized by the primary T cells that were redirected to express NY-ESO-1 specific TCRs. A375 cells could be recognized by all three specific TCRs expressed by T cells. Both pShuttle-EF1a-E1A d24-A2-NY and pShuttle-EF1a-E1A d24-A2-BM could sensitize the A375 and SKOV3-NY cells to be recognized by the specific TCRs expressed by T cells. SKOV3 cells could only be sensitized by pShuttle-EF1a-E1A d24-A2-NY that provides both HLA-A2 molecule as well as the NY-ESO-1 157-165 epitope peptide. This result confirmed that the said labelling polypeptide containing antigenic epitope peptides as well as the exogenous HLA class I molecule could sensitize tumor cells to be recognized not only by JRT cell line expressing the specific TCR but also the primary T cells that were redirected to express the specific TCR and usually utilized for adoptive T cell therapy against cancer.

To assess if other types of tumor cells could be sensitized by being transduced with the nucleic acid encoding the said labelling polypeptide and/or exogenous HLA class I molecule, human lung cancer cell line H1299 (NY-ESO-1+/HLA-A2–), human osteosarcoma cell line HOS-C1(NY-ESO-1 low/HLA-A2+), and human lung cancer cell line A549 (NY-ESO-1–/HLA-A2–) were transduced with pShuttle-NY-A2 vector and utilized as target cells. PBMCs transduced with the recombinant lentivirus expressing TCR-NY-LY or TCR-NY-LI acted as effector cells. The mock cells were the PBMCs transduced with an empty lentivirus. The effector cells or the mock cells were incubated with the target cells for 24 hours at a 5:1 E:T ratio. The secretion of IFN-gamma in the supernatant was assessed with ELISA. As shown in FIG. 4C, a large amount of IFN-gamma was produced by the re-directed specific T cells with TCR-NY-LY or TCR-NY-LI after stimulation by the target cells transduced with pShuttle-NY-A2 compared to the control group with the mock T cells (Student's t-Test, p<0.01), which demonstrated that all tested tumor cells were able be sensitized by the labelling polypeptide containing NY-ESO-1 157-165 epitope peptides and the exogenous HLA-A2 protein to be recognized by the T cells expressing the NY-ESO-1 specific TCR.

CONCLUSION

The said labelling polypeptide containing the antigenic epitope peptides and/or the exogenous HLA class I molecule can sensitize tumor cells to be recognized by T cells expressing a specific TCR once the nucleic acids encoding these exogenous peptides or HLA class I proteins are delivered into tumor cells by a vehicle that can be a plasmid vector, a recombinant virus, a nanoparticle or naked DNA or RNA. The combination therapy for solid tumors, as suggested in the present disclosure, extend the application scope of adoptive T cell therapy to patients who normally may not be enrolled in trials due to unmatched HLA type despite their tumor expressing the particular tumor antigen. In theory, delivering nucleic acids encoding both the said labelling polypeptide comprising antigenic epitopes and the HLA class I molecule that can present the antigenic epitope peptide into tumor cells and sensitizing them to be recognized by the adoptively transferred T cells can be considered as a universal approach to treat a variety of tumors regardless of their HLA class I type and the antigen expression level in tumor cells. One possible toxicity that can occur is when normal cells unwantedly acquire the labelling nucleic acids and become the targets of the adoptively transferred T cells. This risk can be avoided or manageable if the delivery vehicle selectively targets tumor cells to express the labelling polypeptide or exogenous HLA molecule, such as using a conditionally replication-competent virus as suggested in the present disclosure. Practically, if the antigen processing and presentation machinery was deficient, which frequently occurs in tumor cells, transducing tumor cells to express the said labelling polypeptide comprising of an antigenic epitope as well as an HLA class I molecule that can present the antigenic epitope peptide would be an option to sensitize the tumor cells to become the target of adoptively transferred T cells. Moreover, the combination therapy, as suggested by the present invention, of delivering an allogenic HLA class I molecule into tumor cells to present the neo-epitopes that are originated from the most frequently mutated tumor-driven proteins such as KRAS or p53 but cannot be presented by endogenous HLA class I molecules and sensitizing the tumor cells to be recognized and eliminated by the adoptively transferred T cells would be a promising therapeutic approach to benefit more patients with cancer.

What is claimed is:

1. A therapeutic agent for the treatment of tumors and/or cancers of a subject, comprising:
   (a) a first pharmaceutical composition comprising a first active ingredient in a first druggable vehicle, wherein the first active ingredient comprises a nucleic acid encoding a labelling polypeptide;
   (b) a second pharmaceutical composition comprising a second active ingredient in a second druggable vehicle, wherein the second active ingredient comprises immune cells purified from peripheral blood or from tumor tissue and are cultured in vitro;
   wherein the nucleic acid when administered to the patient as part of the first pharmaceutical composition causes the tumor cells and/or cancer cells of the patient to express immunogens that can elicit an immune response of the immune cells;
   wherein the labelling polypeptide comprises three identical antigenic epitope peptides derived from a tumor-associated antigen of NY-ESO-1 157-165 (SEQ ID NO:2), and the immune cells comprise TCR-modified T cells that can specifically recognize and bind to the labelling polypeptide; and
   wherein the first active ingredient is a recombinant oncolytic adenovirus capable of selectively replicating in tumor cells.

2. The therapeutic agent of claim 1, wherein the labelling polypeptide comprises an operably linked and tandem amino acid sequence as the following: a N-terminal signal peptide, the three identical antigenic epitope peptides, and a C-terminal endoplasmic reticulum (ER) retention signal sequence Lys-Asp-Glu-Leu (SEQ ID NO: 38).

3. The therapeutic agent of claim 2, wherein the N-terminal signal peptide is derived from an Insulin-like peptide INSL5: 1-22 as shown in SEQ ID NO:1.

4. The therapeutic agent of claim 1, wherein each of the two adjacent antigenic epitope peptides is connected by a self-cleaving linker peptide.

5. The therapeutic agent of claim 4, wherein the self-cleaving linker peptide is a furin enzyme cleavage peptide Arg-X-[Lys/Arg]-Arg (X is any amino acid residue).

6. The therapeutic agent of claim 1, wherein the therapeutic agent further comprises gene-expression regulatory elements, wherein the gene-expression regulatory elements are exogenous gene-expression regulatory elements or the first active ingredient's own gene-expression regulatory elements; wherein the gene-expression regulatory elements comprise a promoter, an enhancer, a silencer and a polyadenylation signal.

7. The therapeutic agent of claim 1, the nucleic acid further encodes an exogenous HLA protein that can present the antigenic epitope peptide on the cell surfaces of the tumor and/or cancer.

8. The therapeutic agent of claim 7, wherein the HLA protein and the labelling polypeptide are operably connected by a self-cleaving linker peptide, wherein the expression of the HLA protein and the labelling polypeptide are under the control of separate promoters or under the control of the same promoter.

9. The therapeutic agent of claim 1, wherein the nucleic acid further encodes a human leukocyte antigen (HLA) protein; wherein the expression of HLA protein is controlled by exogenous gene-expression regulatory elements or the first active ingredient's own gene-expression regulatory elements.

10. The therapeutic agent of claim 1, wherein the genome of the recombinant oncolytic adenovirus has the E1B-55K and E1B-19K genes deleted while retaining the E1A gene as shown in SEQ ID NO: 34.

11. A method of treating tumors and/or cancers of a subject, comprising administering a therapeutically effective dose of the therapeutic agent of claim 1 to the subject.

12. The method of claim 11, wherein the tumors and/or cancers are selected from the group consisting of: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, pheochromocytoma, prolactinoma, von Hippel-Lindau disease, Zollinger-Ellison syndrome, anal cancer, cholangiocarcinoma, bladder cancer, urethral cancer, glioma, neuroblastoma, meningioma, spinal cord tumor, Bone tumor, chondrosarcoma, Ewing's sarcoma, cancer of unknown primary site, carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, cardiac sarcoma, meningeal carcinomatosis, primary peritoneal carcinoma and malignant pleural mesothelioma.

13. The method of claim 11, wherein the therapeutic agent is successively administered in the following steps:
   a) administering the first composition of the therapeutic agent to the subject;
   b) after administering the first composition, administering the second composition of the therapeutic agent to the subject;
   wherein the tumors and/or cancers are selected from the group consisting of: breast cancer, head and neck cancer, glioblastoma, synoviosarcoma, kidney cancer, sarcoma, melanoma, lung cancer, esophageal cancer, colon cancer, rectal cancer, brain cancer, liver cancer, bone cancer, choriocarcinoma, neuroendocrine tumor, pheochromocytoma, prolactinoma, von Hippel-Lindau disease, Zollinger-Ellison syndrome, anal cancer, cholangiocarcinoma, bladder cancer, urethral cancer, glioma, neuroblastoma, meningioma, spinal cord tumor, bone tumor, chondrosarcoma, Ewing's sarcoma, cancer of unknown primary site, carcinoid tumor, mesenchymal tumors, Paget's disease, cervical cancer, gallbladder cancer, eye cancer, Kaposi sarcoma, prostate cancer, testicular cancer, skin squamous cell carcinoma, mesothelioma, multiple myeloma, ovarian cancer, pancreatic cancer, penile cancer, pituitary carcinoma, soft tissue sarcoma, retinoblastoma, intestinal tumor, stomach/gastric cancer, thymus carcinoma, gestational trophoblastic neoplasia, endometrial cancer, vaginal cancer, vulvar cancer, mycosis fungoides, insulinoma, cardiac sarcoma, meningeal carcinomatosis, primary peritoneal carcinoma and malignant pleural mesothelioma.

* * * * *

SEQUENCE LISTING

```
<160> NUMBER OF SEQ ID NOS: 59

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-Terminal Signal Peptide of Insulin-Like
      Peptide INSL5

<400> SEQUENCE: 1

Met Lys Gly Ser Ile Phe Thr Leu Phe Leu Phe Ser Val Leu Phe Ala
1               5                   10                  15

Ile Ser Glu Val Arg Ser
            20

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: The amino acid sequence of NY-ESO1 157-165

<400> SEQUENCE: 2

Ser Leu Leu Met Trp Ile Thr Gln Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: The amino acid sequence of KRAS: G12D 10-18

<400> SEQUENCE: 3

Gly Ala Asp Gly Val Gly Lys Ser Ala
1               5

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: The self-cleaving linker peptide containing a
      furin enzyme cleavage peptide and a 2A peptid

<400> SEQUENCE: 4

Arg Ala Lys Arg Ser Gly Ser Gly Ala Pro Val Lys Gln Thr Leu Asn
1               5                   10                  15

Phe Asp Leu Leu Lys Leu Ala Gly Asp Val Glu Ser Asn Pro Gly Pro
            20                  25                  30

<210> SEQ ID NO 5
<211> LENGTH: 365
<212> TYPE: PRT
<213> ORGANISM: Homo sapiens
<220> FEATURE:
<223> OTHER INFORMATION: HLA-A*02:01 protein wild type

<400> SEQUENCE: 5

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220
```

```
Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
        260                 265                 270

Val Pro Ser Gly Gln Glu Gln Arg Tyr Thr Cys His Val Gln His Glu
    275                 280                 285

Gly Leu Pro Lys Pro Leu Thr Leu Arg Trp Glu Pro Ser Ser Gln Pro
290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
            325                 330                 335

Ser Asp Arg Lys Gly Gly Ser Tyr Ser Gln Ala Ala Ser Ser Asp Ser
                340                 345                 350

Ala Gln Gly Ser Asp Val Ser Leu Thr Ala Cys Lys Val
        355                 360                 365

<210> SEQ ID NO 6
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mutant HLA-C*08:02 protein comprising the
      E337V and I337T substitutions

<400> SEQUENCE: 6

Met Arg Val Met Ala Pro Arg Thr Leu Ile Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Gly Arg Gly Glu Pro Arg Phe Ile Ala
        35                  40                  45

Val Gly Tyr Val Asp Asp Thr Gln Phe Val Gln Phe Asp Ser Asp Ala
    50                  55                  60

Ala Ser Pro Arg Gly Glu Pro Arg Ala Pro Trp Val Glu Gln Glu Gly
65                  70                  75                  80

Pro Glu Tyr Trp Asp Arg Glu Thr Gln Lys Tyr Lys Arg Gln Ala Gln
                85                  90                  95

Thr Asp Arg Val Ser Leu Arg Asn Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asn Gln Phe Ala Tyr Asp Gly
    130                 135                 140

Lys Asp Tyr Ile Ala Leu Asn Glu Asp Leu Arg Ser Trp Thr Ala Ala
145                 150                 155                 160

Asp Lys Ala Ala Gln Ile Thr Gln Arg Lys Trp Glu Ala Ala Arg Glu
                165                 170                 175

Ala Glu Gln Arg Arg Ala Tyr Leu Glu Gly Thr Cys Val Glu Trp Leu
            180                 185                 190

Arg Arg Tyr Leu Glu Asn Gly Lys Lys Thr Leu Gln Arg Ala Glu His
        195                 200                 205
```

```
Pro Lys Thr His Val Thr His His Pro Val Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Glu Pro Leu Thr Leu Arg Trp Gly Pro Ser Ser Gln Pro
        290                 295                 300

Thr Ile Pro Ile Val Gly Ile Val Ala Gly Leu Ala Val Leu Ala Val
305                 310                 315                 320

Leu Ala Val Leu Gly Ala Val Met Ala Val Met Cys Arg Arg Lys
                325                 330                 335

Ser Ser Gly Gly Lys Gly Gly Ser Cys Ser Gln Ala Ala Ser Ser Asn
                340                 345                 350

Ser Ala Gln Gly Ser Asp Val Ser Leu Thr Ala Cys Lys Ala
                355                 360                 365

<210> SEQ ID NO 7
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HLA- A*02:01 protein and beta-2 microglobulin
      are connected with F2A

<400> SEQUENCE: 7

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
                35                  40                  45

Val Gly Tyr Val Asp Asp Thr Gln Phe Val Arg Phe Asp Ser Asp Ala
            50                  55                  60

Ala Ser Gln Arg Met Glu Pro Arg Ala Pro Trp Ile Glu Gln Glu Gly
65              70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
                100                 105                 110

Glu Ala Gly Ser His Thr Val Gln Arg Met Tyr Gly Cys Asp Val Gly
                115                 120                 125

Ser Asp Trp Arg Phe Leu Arg Gly Tyr His Gln Tyr Ala Tyr Asp Gly
        130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
                180                 185                 190
```

```
Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val Arg Ala Lys
        355                 360                 365

Arg Ser Gly Ser Gly Ala Pro Val Lys Gln Thr Leu Asn Phe Asp Leu
370                 375                 380

Leu Lys Leu Ala Gly Asp Val Glu Ser Asn Pro Gly Pro Met Ser Arg
385                 390                 395                 400

Ser Val Ala Leu Ala Val Leu Ala Leu Leu Ser Leu Ser Gly Leu Glu
                405                 410                 415

Ala Ile Gln Arg Thr Pro Lys Ile Gln Val Tyr Ser Arg His Pro Ala
            420                 425                 430

Glu Asn Gly Lys Ser Asn Phe Leu Asn Cys Tyr Val Ser Gly Phe His
        435                 440                 445

Pro Ser Asp Ile Glu Val Asp Leu Leu Lys Asn Gly Glu Arg Ile Glu
450                 455                 460

Lys Val Glu His Ser Asp Leu Ser Phe Ser Lys Asp Trp Ser Phe Tyr
465                 470                 475                 480

Leu Leu Tyr Tyr Thr Glu Phe Thr Pro Thr Glu Lys Asp Glu Tyr Ala
                485                 490                 495

Cys Arg Val Asn His Val Thr Leu Ser Gln Pro Lys Ile Val Lys Trp
            500                 505                 510

Asp Arg Asp Met
        515

<210> SEQ ID NO 8
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: A mutant HLA-C*08:02 protein comprising the
      E337V and I337T substitutions and beta-2 microglobulin are
      connected with F2A
```

<400> SEQUENCE: 8

```
Met Ala Val Met Ala Pro Arg Thr Leu Val Leu Leu Leu Ser Gly Ala
1               5                   10                  15
Leu Ala Leu Thr Gln Thr Trp Ala Gly Ser His Ser Met Arg Tyr Phe
            20                  25                  30
Phe Thr Ser Val Ser Arg Pro Gly Arg Gly Glu Pro Arg Phe Ile Ala
        35                  40                  45
Val Gly Tyr Val Asp Asp Thr Gln Phe Val Arg Phe Asp Ser Asp Ala
    50                  55                  60
Ala Ser Gln Arg Met Glu Pro Arg Ala Pro Trp Ile Glu Gln Glu Gly
65                  70                  75                  80
Pro Glu Tyr Trp Asp Gly Glu Thr Arg Lys Val Lys Ala His Ser Gln
                85                  90                  95
Thr His Arg Val Asp Leu Gly Thr Leu Arg Gly Tyr Tyr Asn Gln Ser
            100                 105                 110
Glu Ala Gly Ser His Thr Val Gln Arg Met Tyr Gly Cys Asp Val Gly
        115                 120                 125
Ser Asp Trp Arg Phe Leu Arg Gly Tyr His Gln Tyr Ala Tyr Asp Gly
    130                 135                 140
Lys Asp Tyr Ile Ala Leu Lys Glu Asp Leu Arg Ser Trp Thr Ala Ala
145                 150                 155                 160
Asp Met Ala Ala Gln Thr Thr Lys His Lys Trp Glu Ala Ala His Val
                165                 170                 175
Ala Glu Gln Leu Arg Ala Tyr Leu Glu Gly Thr Cys Val Glu Trp Leu
            180                 185                 190
Arg Arg Tyr Leu Glu Asn Gly Lys Glu Thr Leu Gln Arg Thr Asp Ala
        195                 200                 205
Pro Lys Thr His Met Thr His His Ala Val Ser Asp His Glu Ala Thr
    210                 215                 220
Leu Arg Cys Trp Ala Leu Ser Phe Tyr Pro Ala Glu Ile Thr Leu Thr
225                 230                 235                 240
Trp Gln Arg Asp Gly Glu Asp Gln Thr Gln Asp Thr Glu Leu Val Glu
                245                 250                 255
Thr Arg Pro Ala Gly Asp Gly Thr Phe Gln Lys Trp Ala Ala Val Val
            260                 265                 270
Val Pro Ser Gly Gln Glu Gln Arg Tyr Thr Cys His Val Gln His Glu
        275                 280                 285
Gly Leu Pro Lys Pro Leu Thr Leu Arg Trp Glu Pro Ser Ser Gln Pro
    290                 295                 300
Thr Ile Pro Ile Val Gly Ile Ile Ala Gly Leu Val Leu Phe Gly Ala
305                 310                 315                 320
Val Ile Thr Gly Ala Val Val Ala Ala Val Met Trp Arg Arg Lys Ser
                325                 330                 335
Ser Asp Arg Lys Gly Gly Ser Tyr Ser Gln Ala Ala Ser Ser Asp Ser
            340                 345                 350
Ala Gln Gly Ser Asp Val Ser Leu Thr Ala Cys Lys Val Arg Ala Lys
        355                 360                 365
Arg Ser Gly Ser Gly Ala Pro Val Lys Gln Thr Leu Asn Phe Asp Leu
    370                 375                 380
Leu Lys Leu Ala Gly Asp Val Glu Ser Asn Pro Gly Pro Met Ser Arg
385                 390                 395                 400
Ser Val Ala Leu Ala Val Leu Ala Leu Leu Ser Leu Ser Gly Leu Glu
                405                 410                 415
```

```
Ala Ile Gln Arg Thr Pro Lys Ile Gln Val Tyr Ser Arg His Pro Ala
            420                 425                 430

Glu Asn Gly Lys Ser Asn Phe Leu Asn Cys Tyr Val Ser Gly Phe His
            435                 440                 445

Pro Ser Asp Ile Glu Val Asp Leu Leu Lys Asn Gly Glu Arg Ile Glu
            450                 455                 460

Lys Val Glu His Ser Asp Leu Ser Phe Ser Lys Asp Trp Ser Phe Tyr
465                 470                 475                 480

Leu Leu Tyr Tyr Thr Glu Phe Thr Pro Thr Lys Glu Tyr Ala
                485                 490                 495

Cys Arg Val Asn His Val Thr Leu Ser Gln Pro Lys Ile Val Lys Trp
            500                 505                 510

Asp Arg Asp Met
            515

<210> SEQ ID NO 9
<211> LENGTH: 289
<212> TYPE: PRT
<213> ORGANISM: Human adenovirus 5
<220> FEATURE:
<223> OTHER INFORMATION: Type 5 Adenovirus E1A-32kDa protein wild type

<400> SEQUENCE: 9

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
                20                  25                  30

Pro Pro Pro Ser His Phe Glu Pro Thr Leu His Glu Leu Tyr Asp
            35                  40                  45

Leu Asp Val Thr Ala Pro Glu Asp Pro Asn Glu Glu Ala Val Ser Gln
50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
            115                 120                 125

Phe Pro Pro Ser Asp Asp Glu Asp Glu Glu Gly Glu Glu Phe Val Leu
            130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
            195                 200                 205

Met Ala Pro Ala Ile Leu Arg Arg Pro Thr Ser Pro Val Ser Arg Glu
            210                 215                 220

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
                245                 250                 255
```

```
Val Arg Val Gly Gly Arg Arg Gln Ala Val Glu Cys Ile Glu Asp Leu
            260                 265                 270

Leu Asn Glu Pro Gly Gln Pro Leu Asp Leu Ser Cys Lys Arg Pro Arg
        275                 280                 285

Pro

<210> SEQ ID NO 10
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: native E1B promoter (including E1B TATA box
      sequence and Kozak sequence) )

<400> SEQUENCE: 10
gtgtctagag aatgcaatag tagtacggat agctgtgact ccggtccttc taacacacct      60
cctgagatac acccggtggt cccgctgtgc cccattaaac cagttgccgt gagagttggt     120
gggcgtcgcc aggctgtgga atgtatcgag gacttgctta acgagcctgg gcaacctttg     180
gacttgagct gtaaacgccc caggccataa ggtgtaaacc tgtgattgcg tgtgtggtta     240
acgcctttgt ttgctgaatg agttgatgta agtttaataa agggtgagat aatgtttaac     300
ttgcatggcg tgttaaatgg ggcggggctt aaagggtata taatgcgccg tgggctaatc     360
ttggttacat ctgacctcgc caccatgg                                        388

<210> SEQ ID NO 11
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: (E1A protein contains a 24-base pair deletion
      (E1A 122-129))

<400> SEQUENCE: 11

Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
    50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Pro Ser Asp Glu Asp
        115                 120                 125

Glu Glu Gly Glu Glu Phe Val Leu Asp Tyr Val Glu His Pro Gly His
    130                 135                 140

Gly Cys Arg Ser Cys His Tyr His Arg Arg Asn Thr Gly Asp Pro Asp
145                 150                 155                 160
```

```
Ile Met Cys Ser Leu Cys Tyr Met Arg Thr Cys Gly Met Phe Val Tyr
            165                 170                 175

Ser Pro Val Ser Glu Pro Glu Pro Glu Pro Glu Pro Glu Pro Glu Pro
            180                 185                 190

Ala Arg Pro Thr Arg Arg Pro Lys Met Ala Pro Ala Ile Leu Arg Arg
            195                 200                 205

Pro Thr Ser Pro Val Ser Arg Glu Cys Asn Ser Ser Thr Asp Ser Cys
210                 215                 220

Asp Ser Gly Pro Ser Asn Thr Pro Pro Glu Ile His Pro Val Val Pro
225                 230                 235                 240

Leu Cys Pro Ile Lys Pro Val Ala Val Arg Val Gly Gly Arg Arg Gln
                245                 250                 255

Ala Val Glu Cys Ile Glu Asp Leu Leu Asn Glu Pro Gly Gln Pro Leu
            260                 265                 270

Asp Leu Ser Cys Lys Arg Pro Arg Pro
            275                 280
```

<210> SEQ ID NO 12
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mutant E1A protein contains the point
      mutations L122V, C124S and E126D

<400> SEQUENCE: 12

```
Met Arg His Ile Ile Cys His Gly Gly Val Ile Thr Glu Glu Met Ala
1               5                   10                  15

Ala Ser Leu Leu Asp Gln Leu Ile Glu Glu Val Leu Ala Asp Asn Leu
            20                  25                  30

Pro Pro Pro Ser His Phe Glu Pro Pro Thr Leu His Glu Leu Tyr Asp
            35                  40                  45

Leu Asp Val Thr Ala Pro Glu Asp Pro Asn Glu Glu Ala Val Ser Gln
50                  55                  60

Ile Phe Pro Asp Ser Val Met Leu Ala Val Gln Glu Gly Ile Asp Leu
65                  70                  75                  80

Leu Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Val Thr Ser His Asp Ala Gly
            115                 120                 125

Phe Pro Pro Ser Asp Asp Glu Asp Glu Glu Gly Glu Glu Phe Val Leu
            130                 135                 140

Asp Tyr Val Glu His Pro Gly His Gly Cys Arg Ser Cys His Tyr His
145                 150                 155                 160

Arg Arg Asn Thr Gly Asp Pro Asp Ile Met Cys Ser Leu Cys Tyr Met
                165                 170                 175

Arg Thr Cys Gly Met Phe Val Tyr Ser Pro Val Ser Glu Pro Glu Pro
            180                 185                 190

Glu Pro Glu Pro Glu Pro Glu Pro Ala Arg Pro Thr Arg Arg Pro Lys
            195                 200                 205

Met Ala Pro Ala Ile Leu Arg Arg Pro Thr Ser Pro Val Ser Arg Glu
210                 215                 220
```

-continued

Cys Asn Ser Ser Thr Asp Ser Cys Asp Ser Gly Pro Ser Asn Thr Pro
225                 230                 235                 240

Pro Glu Ile His Pro Val Val Pro Leu Cys Pro Ile Lys Pro Val Ala
            245                 250                 255

Val Arg Val Gly Gly Arg Arg Gln Ala Val Glu Cys Ile Glu Asp Leu
        260                 265                 270

Leu Asn Glu Pro Gly Gln Pro Leu Asp Leu Ser Cys Lys Arg Pro Arg
    275                 280                 285

Pro

<210> SEQ ID NO 13
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Labelling polypeptide containing NY-ESO-1 157-
      165

<400> SEQUENCE: 13

Met Lys Gly Ser Ile Phe Thr Leu Phe Leu Ser Val Leu Phe Ala
1               5                   10                  15

Ile Ser Glu Val Arg Ser Ser Leu Leu Met Trp Ile Thr Gln Cys Arg
            20                  25                  30

Arg Lys Arg Ser Leu Leu Met Trp Ile Thr Gln Cys Arg Arg Lys Arg
        35                  40                  45

Ser Leu Leu Met Trp Ile Thr Gln Cys Arg Arg Arg Lys Asp Glu
    50                  55                  60

Leu
65

<210> SEQ ID NO 14
<211> LENGTH: 69
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Labelling polypeptide containing KRAS: G12D 10-
      19

<400> SEQUENCE: 14

Met Lys Gly Ser Ile Phe Thr Leu Phe Leu Ser Val Leu Phe Ala
1               5                   10                  15

Ile Ser Glu Val Arg Ser Gly Ala Asp Gly Val Gly Lys Ser Ala Arg
            20                  25                  30

Arg Lys Arg Arg Arg Lys Arg Gly Ala Asp Gly Val Gly Lys Ser Ala
        35                  40                  45

Arg Arg Lys Arg Gly Ala Asp Gly Val Gly Lys Ser Ala Arg Arg Lys
    50                  55                  60

Arg Lys Asp Glu Leu
65

<210> SEQ ID NO 15
<211> LENGTH: 1098
<212> TYPE: DNA
<213> ORGANISM: Homo sapiens
<220> FEATURE:
<223> OTHER INFORMATION: cDNA encoding full length HLA-A*02:01

<400> SEQUENCE: 15

| | | | | | |
|---|---|---|---|---|---|
| atggccgtca | tggcgccccg | aaccctcgtc | ctgctactct | cgggggctct | ggccctgacc | 60 |
| cagacctggg | cgggctctca | ctccatgagg | tatttcttca | catccgtgtc | ccggcccggc | 120 |
| cgcggggagc | cccgcttcat | cgcagtgggc | tacgtggacg | acacgcagtt | cgtgcggttc | 180 |
| gacagcgacg | ccgcgagcca | gaggatggag | ccgcgggcgc | cgtggataga | gcaggagggt | 240 |
| ccggagtatt | gggacgggga | gacacggaaa | gtgaaggccc | actcacagac | tcaccgagtg | 300 |
| gacctgggga | ccctgcgcgg | ctactacaac | cagagcgagg | ccggttctca | caccgtccag | 360 |
| aggatgtatg | gctgcgacgt | ggggtcggac | tggcgcttcc | tccgcgggta | ccaccagtac | 420 |
| gcctacgacg | gcaaggatta | catcgccctg | aaagaggacc | tgcgctcttg | gaccgcggcg | 480 |
| gacatggcag | ctcagaccac | caagcacaag | tgggaggcgg | cccatgtggc | ggagcagttg | 540 |
| agagcctacc | tggagggcac | gtgcgtggag | tggctccgca | gatacctgga | gaacgggaag | 600 |
| gagacgctgc | agcgcacgga | cgcccccaaa | acgcatatga | ctcaccacgc | tgtctctgac | 660 |
| catgaagcca | cctgaggtg | ctgggccctg | agcttctacc | ctgcggagat | cacactgacc | 720 |
| tggcagcggg | atggggagga | ccagacccag | gacacggagc | tcgtggagac | caggcctgca | 780 |
| ggggatggaa | ccttccagaa | gtgggcggct | gtggtggtgc | cttctggaca | ggagcagaga | 840 |
| tacacctgcc | atgtgcagca | tgagggtttg | cccaagcccc | tcaccctgag | atgggagccg | 900 |
| tcttcccagc | ccaccatccc | catcgtgggc | atcattgctg | gctggttct | ctttggagct | 960 |
| gtgatcactg | gagctgtggt | cgctgctgtg | atgtggagga | ggaagagctc | agatagaaaa | 1020 |
| ggagggagct | actctcaggc | tgcaagcagt | gacagtgccc | agggctctga | tgtgtctctc | 1080 |
| acagcttgta | aagtgtga | | | | | 1098 |

<210> SEQ ID NO 16
<211> LENGTH: 1101
<212> TYPE: DNA
<213> ORGANISM: Homo sapiens

<400> SEQUENCE: 16

| | | | | | |
|---|---|---|---|---|---|
| atgcgggtca | tggcgccccg | aaccctcatc | ctgctgctct | cgggagccct | ggccctgacc | 60 |
| gagacctggg | cctgctccca | ctccatgagg | tatttctaca | ccgccgtgtc | ccggcccggc | 120 |
| cgcggagagc | cccgcttcat | cgcagtgggc | tacgtggacg | acacgcagtt | cgtgcagttc | 180 |
| gacagcgacg | ccgcgagtcc | aagaggggag | ccgcgggcgc | cgtgggtgga | gcaggagggg | 240 |
| ccggagtatt | gggaccggga | gacacagaag | tacaagcgcc | aggcacagac | tgaccgagtg | 300 |
| agcctgcgga | acctgcgcgg | ctactacaac | cagagcgagg | ccgggtctca | caccctccag | 360 |
| aggatgtatg | gctgcgacct | ggggcccgac | ggcgcctcc | tccgcgggta | taaccagttc | 420 |
| gcctacgacg | gcaaggatta | catcgccctg | aatgaggacc | tgcgctcctg | gaccgccgcg | 480 |
| gacaaggcgg | ctcagatcac | ccagcgcaag | tgggaggcgg | ccgtgaggc | ggagcagcgg | 540 |
| agagcctacc | tggagggcac | gtgcgtggag | tggctccgca | gatacctgga | gaacgggaag | 600 |
| aagacgctgc | agcgcgcgga | cacccaaag | acacacgtga | cccaccatcc | cgtctctgac | 660 |
| catgaggcca | cctgaggtg | ctgggccctg | ggcttctacc | ctgcggagat | cacactgacc | 720 |
| tggcagcggg | atggcgagga | ccaaactcag | gacaccgagc | ttgtggagac | caggccagca | 780 |
| ggagatggaa | ccttccagaa | gtgggcagct | gtggtggtgc | cttctggaga | agagcagaga | 840 |
| tacacgtgcc | atgtgcagca | cgaggggctg | ccagagcccc | tcaccctgag | atgggggcca | 900 |
| tcttcccagc | ccaccatccc | catcgtgggc | atcgttgctg | gcctggctgt | cctggctgtc | 960 |

| | |
|---|---|
| ctagctgtcc taggagctgt gatggctgtt gtgatgtgta ggaggaagag ctcaggtgga | 1020 |
| aaaggaggga gctgctctca ggctgcgtcc agcaacagtg cccagggctc tgatgtgtct | 1080 |
| ctcacagctt gtaaagccta a | 1101 |

<210> SEQ ID NO 17
<211> LENGTH: 1551
<212> TYPE: DNA
<213> ORGANISM: Homo sapiens

<400> SEQUENCE: 17

| | |
|---|---|
| atggccgtca tggcgccccg aaccctcgtc ctgctactct cgggggctct ggccctgacc | 60 |
| cagacctggg cgggctctca ctccatgagg tatttcttca catccgtgtc ccggcccggc | 120 |
| cgcggggagc cccgcttcat cgcagtgggc tacgtggacg acacgcagtt cgtgcggttc | 180 |
| gacagcgacg ccgcgagcca gaggatggag ccgcgggcgc cgtggataga gcaggagggt | 240 |
| ccggagtatt gggacgggga gacacggaaa gtgaaggccc actcacagac tcaccgagtg | 300 |
| gacctgggga ccctgcgcgg ctactacaac cagagcgagg ccggttctca caccgtccag | 360 |
| aggatgtatg gctgcgacgt ggggtcggac tggcgcttcc tccgcgggta ccaccagtac | 420 |
| gcctacgacg gcaaggatta catcgccctg aaagaggacc tgcgctcttg gaccgcggcg | 480 |
| gacatggcag ctcagaccac caagcacaag tgggaggcgg cccatgtggc ggagcagttg | 540 |
| agagcctacc tggagggcac gtgcgtggag tggctccgca gatacctgga aacgggaag | 600 |
| gagacgctgc agcgcacgga cgcccccaaa acgcatatga ctcaccacgc tgtctctgac | 660 |
| catgaagcca ccctgaggtg ctgggccctg agcttctacc ctgcggagat cacactgacc | 720 |
| tggcagcggg atggggagga ccagacccag gacacggagc tcgtggagac caggcctgca | 780 |
| ggggatggaa ccttccagaa gtgggcggct gtggtggtgc cttctggaca ggagcagaga | 840 |
| tacacctgcc atgtgcagca tgagggtttg ccaagcccc tcaccctgag atgggagccg | 900 |
| tcttcccagc ccaccatccc catcgtgggc atcattgctg gcctggttct ctttggagct | 960 |
| gtgatcactg gagctgtggt cgctgctgtg atgtggagga ggaagagctc agatagaaaa | 1020 |
| ggagggagct actctcaggc tgcaagcagt gacagtgccc agggctctga tgtgtctctc | 1080 |
| acagcttgta aagtgcgtgc caagcgatcc ggaagcggag cccctgtaaa gcagactttg | 1140 |
| aattttgacc ttctcaagtt ggcgggagac gtcgagtcca accctgggcc catgtctcgc | 1200 |
| tccgtggcct tagctgtgct cgcgctactc tctctttctg gcctggaggc tatccagcgt | 1260 |
| actccaaaga ttcaggttta ctcacgtcat ccagcagaga atggaaagtc aaatttcctg | 1320 |
| aattgctatg tgtctgggtt tcatccatcc gacattgaag ttgacttact gaagaatgga | 1380 |
| gagagaattg aaaagtgga gcattcagac ttgtctttca gcaaggactg gtctttctat | 1440 |
| ctcttgtact acactgaatt cacccccact gaaaaagatg agtatgcctg ccgtgtgaac | 1500 |
| catgtgactt tgtcacagcc caagatagtt aagtgggatc gagacatgta a | 1551 |

<210> SEQ ID NO 18
<211> LENGTH: 1554
<212> TYPE: DNA
<213> ORGANISM: Homo sapiens

<400> SEQUENCE: 18

| | |
|---|---|
| atgcgggtca tggcgccccg aaccctcatc ctgctgctct cgggagccct ggccctgacc | 60 |
| gagacctggg cctgctccca ctccatgagg tatttctaca ccgccgtgtc ccggcccggc | 120 |
| cgcggagagc cccgcttcat cgcagtgggc tacgtggacg acacgcagtt cgtgcagttc | 180 |

```
gacagcgacg ccgcgagtcc aagaggggag ccgcgggcgc cgtgggtgga gcaggagggg      240
ccggagtatt gggaccggga gacacagaag tacaagcgcc aggcacagac tgaccgagtg      300
agcctgcgga acctgcgcgg ctactacaac cagagcgagg ccgggtctca caccctccag      360
aggatgtatg gctgcgacct ggggcccgac gggcgcctcc tccgcgggta taaccagttc      420
gcctacgacg gcaaggatta catcgccctg aatgaggacc tgcgctcctg gaccgccgcg      480
gacaaggcgg ctcagatcac ccagcgcaag tgggaggcgg cccgtgaggc ggagcagcgg      540
agagcctacc tggagggcac gtgcgtggag tggctccgca gatacctgga gaacgggaag      600
aagacgctgc agcgcgcgga cacccaaaag acacacgtga cccaccatcc cgtctctgac      660
catgaggcca ccctgaggtg ctgggccctg gcttctaccc tgcggagat cacactgacc       720
tggcagcggg atggcgagga ccaaaactcag gacaccgagc ttgtggagac caggccagca     780
ggagatggaa ccttccagaa gtgggcagct gtggtggtgc cttctggaga agagcagaga     840
tacacgtgcc atgtgcagca cgaggggctg ccagagcccc tcaccctgag atggggccca     900
tcttcccagc ccaccatccc catcgtgggc atcgttgctg gcctggctgt cctggctgtc     960
ctagctgtcc taggagctgt gatggctgtt gtgatgtgta ggaggaagag ctcaggtgga    1020
aaaggaggga gctgctctca ggctgcgtcc agcaacagtg cccagggctc tgatgtgtct    1080
ctcacagctt gtaaagcccg tgccaagcga tccggaagcg agccccctgt aaagcagact    1140
ttgaattttg accttctcaa gttggcggga gacgtcgagt ccaaccctgg gcccatgtct    1200
cgctccgtgg ccttagctgt gctcgcgcta ctctctcttt ctggcctgga ggctatccag    1260
cgtactccaa agattcaggt ttactcacgt catccagcag agaatggaaa gtcaaatttc    1320
ctgaattgct atgtgtctgg gtttcatcca tccgacattg aagttgactt actgaagaat    1380
ggagagagaa ttgaaaaagt ggagcattca gacttgtctt tcagcaagga ctggtctttc    1440
tatctcttgt actacactga attcaccccc actgaaaaag atgagtatgc ctgccgtgtg    1500
aaccatgtga ctttgtcaca gcccaagata gttaagtggg atcgagacat gtaa          1554
```

<210> SEQ ID NO 19  
<211> LENGTH: 870  
<212> TYPE: DNA  
<213> ORGANISM: Human adenovirus 5  
<220> FEATURE:  
<223> OTHER INFORMATION: Type 5 adenovirus E1A-289R protein wild type

<400> SEQUENCE: 19

```
atgagacata ttatctgcca cggaggtgtt attaccgaag aaatggccgc cagtcttttg       60
gaccagctga tcgaagaggt actggctgat aatcttccac ctcctagcca ttttgaacca      120
cctacccttc acgaactgta tgatttagac gtgacggccc ccgaagatcc caacgaggag      180
gcggtttcgc agattttttcc cgactctgta atgttggcgg tgcaggaagg gattgactta     240
ctcactttc cgccggcgcc cggttctccg gagccgcctc acctttcccg gcagcccgag       300
cagccggagc agagagcctt gggtccggtt tctatgccaa ccttgtacc ggaggtgatc       360
gatcttacct gccacgaggc tggctttcca cccagtgacg acgaggatga agagggtgag      420
gagtttgtgt tagattatgt ggagcacccc gggcacggtt gcaggtcttg tcattatcac      480
cggaggaata cggggaccc agatattatg tgttcgcttt gctatatgag gacctgtggc      540
atgtttgtct acagtcctgt gtctgaacct gagcctgagc ccgagccaga accggagcct      600
gcaagaccta cccgccgtcc taaaatgcg cctgctatcc tgagacgccc gacatcacct      660
gtgtctagag aatgcaatag tagtacggat agctgtgact ccggtccttc taacacacct     720
```
cctgagatac acccggtggt cccgctgtgc cccattaaac cagttgccgt gagagttggt    780
gggcgtcgcc aggctgtgga atgtatcgag gacttgctta acgagcctgg gcaacctttg    840
gacttgagct gtaaacgccc caggccataa                                     870

<210> SEQ ID NO 20
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding E1A-289 protein
      containing a 24-base pair deletion (E1A 122-129)

<400> SEQUENCE: 20
atgagacata ttatctgcca cggaggtgtt attaccgaag aaatggccgc cagtcttttg     60
gaccagctga tcgaagaggt actggctgat aatcttccac ctcctagcca ttttgaacca    120
cctacccttc acgaactgta tgatttagac gtgacggccc ccgaagatcc caacgaggag    180
gcggtttcgc agattttcc cgactctgta atgttggcgg tgcaggaagg gattgactta    240 ctcactttc cgccggcgcc cggttctccg gagccgcctc acctttcccg gcagcccgag    300
cagccggagc agagagcctt gggtccggtt tctatgccaa accttgtacc ggaggtgatc    360
gatccaccca gtgacgacga ggatgaagag ggtgaggagt ttgtgttaga ttatgtggag    420
caccccgggc acggttgcag gtcttgtcat tatcaccgga ggaatacggg ggacccagat    480
attatgtgtt cgctttgcta tatgaggacc tgtggcatgt ttgtctacag tcctgtgtct    540
gaacctgagc ctgagcccga gccagaaccg gagcctgcaa gacctacccg ccgtcctaaa    600
atggcgcctg ctatcctgag acgcccgaca tcacctgtgt ctagagaatg caatagtagt    660
acggatagct gtgactccgg tccttctaac acacctcctg agatacaccc ggtggtcccg    720
ctgtgcccca ttaaaccagt tgccgtgaga gttggtgggc gtcgccaggc tgtggaatgt    780
atcgaggact tgcttaacga gcctgggcaa cctttggact tgagctgtaa acgccccagg    840
ccataa                                                              846

<210> SEQ ID NO 21
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding E1A -289R protein
      contains the point mutations L122V, C124S and E126D

<400> SEQUENCE: 21
atgagacata ttatctgcca cggaggtgtt attaccgaag aaatggccgc cagtcttttg     60
gaccagctga tcgaagaggt actggctgat aatcttccac ctcctagcca ttttgaacca    120
cctacccttc acgaactgta tgatttagac gtgacggccc ccgaagatcc caacgaggag    180
gcggtttcgc agattttcc cgactctgta atgttggcgg tgcaggaagg gattgactta    240 ctcactttc cgccggcgcc cggttctccg gagccgcctc acctttcccg gcagcccgag    300
cagccggagc agagagcctt gggtccggtt tctatgccaa accttgtacc ggaggtgatc    360
gatgttacct cccacgacgc tggctttcca cccagtgacg acgaggatga agagggtgag    420
gagtttgtgt tagattatgt ggagcacccc gggcacggtt gcaggtcttg tcattatcac    480

```
cggaggaata cggggggaccc agatattatg tgttcgcttt gctatatgag gacctgtggc    540
atgtttgtct acagtcctgt gtctgaacct gagcctgagc ccgagccaga accggagcct    600
gcaagaccta cccgccgtcc taaaatggcg cctgctatcc tgagacgccc gacatcacct    660
gtgtctagag aatgcaatag tagtacggat agctgtgact ccggtccttc taacacacct    720
cctgagatac acccggtggt cccgctgtgc cccattaaac cagttgccgt gagagttggt    780
gggcgtcgcc aggctgtgga atgtatcgag gacttgctta acgagcctgg gcaaccttgg    840
gacttgagct gtaaacgccc caggccataa                                       870
```

<210> SEQ ID NO 22
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding the labelling
      polypeptide containing NY-ESO-1 157-165

<400> SEQUENCE: 22

```
atgaaaggtt ccatcttcac attgttttg ttctccgtat tgttcgcaat cagcgaagtc    60
cgatcatccc tgttgatgtg gatcacgcag tgccgcagaa agaggtcact cttaatgtgg   120
ataacccaat gtaggcgaaa gagatcgcta ttgatgtgga ttacacagtg taggcgaagg   180
cggaaagacg agctttaa                                                  198
```

<210> SEQ ID NO 23
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding the labelling
      polypeptide containing KRAS: G12D 10-19

<400> SEQUENCE: 23

```
atgaaaggtt ccatcttcac attgttttg ttctccgtat tgttcgcaat cagcgaagtc    60
cgatcaggag ctgatggcgt aggcaagagt gcccgcagaa agaggcgcag aaagaggggg   120
gccgatggtg ttggaaagag cgctaggcgg aagaggggcg ccgatggtgt cggaaaaagc   180
gcgcggcgga aacgaaaaga cgagctttaa                                    210
```

<210> SEQ ID NO 24
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HLA-A*02:01 and the labelling polypeptide with
      NY-ESO-1 157-165 that are connected by a self-cleaving linker
      peptide F2A

<400> SEQUENCE: 24

```
Met Ala Val Met Ala Pro Arg Thr Leu Val Leu Leu Leu Ser Gly Ala
 1               5                  10                  15

Leu Ala Leu Thr Gln Thr Trp Ala Gly Ser His Ser Met Arg Tyr Phe
            20                  25                  30
```

```
Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
 50                  55                  60

Ala Ser Gln Arg Met Glu Pro Arg Ala Pro Trp Ile Glu Gln Glu Gly
 65                  70                  75                  80

Pro Glu Tyr Trp Asp Gly Glu Thr Arg Lys Val Lys Ala His Ser Gln
                 85                  90                  95

Thr His Arg Val Asp Leu Gly Thr Leu Arg Gly Tyr Tyr Asn Gln Ser
                100                 105                 110

Glu Ala Gly Ser His Thr Val Gln Arg Met Tyr Gly Cys Asp Val Gly
                115                 120                 125

Ser Asp Trp Arg Phe Leu Arg Gly Tyr His Gln Tyr Ala Tyr Asp Gly
            130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
                180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
            210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val Arg Ala Lys
            355                 360                 365

Arg Ser Gly Ser Gly Ala Pro Val Lys Gln Thr Leu Asn Phe Asp Leu
            370                 375                 380

Leu Lys Leu Ala Gly Asp Val Glu Ser Asn Pro Gly Pro Met Lys Gly
385                 390                 395                 400

Ser Ile Phe Thr Leu Phe Leu Phe Ser Val Leu Phe Ala Ile Ser Glu
                405                 410                 415

Val Arg Ser Ser Leu Leu Met Trp Ile Thr Gln Cys Arg Arg Lys Arg
            420                 425                 430
```

```
Ser Leu Leu Met Trp Ile Thr Gln Cys Arg Arg Lys Arg Ser Leu Leu
            435                 440                 445

Met Trp Ile Thr Gln Cys Arg Arg Arg Lys Asp Glu Leu
    450                 455                 460

<210> SEQ ID NO 25
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HLA-C*08:02 protein comprising I337T and E334V
      mutations with the labeling peptide comprising antigenic epitope
      peptide KRAS: G12D 10-18 that are connected by a self-cleaving
      linker peptide F2A

<400> SEQUENCE: 25

Met Arg Val Met Ala Pro Arg Thr Leu Ile Leu Leu Leu Ser Gly Ala
1               5                   10                  15

Leu Ala Leu Thr Glu Thr Trp Ala Cys Ser His Ser Met Arg Tyr Phe
            20                  25                  30

Tyr Thr Ala Val Ser Arg Pro Gly Arg Gly Glu Pro Arg Phe Ile Ala
        35                  40                  45

Val Gly Tyr Val Asp Asp Thr Gln Phe Val Gln Phe Asp Ser Asp Ala
    50                  55                  60

Ala Ser Pro Arg Gly Glu Pro Arg Ala Pro Trp Val Glu Gln Glu Gly
65              70                  75                  80

Pro Glu Tyr Trp Asp Arg Glu Thr Gln Lys Tyr Lys Arg Gln Ala Gln
                85                  90                  95

Thr Asp Arg Val Ser Leu Arg Asn Leu Arg Gly Tyr Tyr Asn Gln Ser
            100                 105                 110

Glu Ala Gly Ser His Thr Leu Gln Arg Met Tyr Gly Cys Asp Leu Gly
        115                 120                 125

Pro Asp Gly Arg Leu Leu Arg Gly Tyr Asn Gln Phe Ala Tyr Asp Gly
    130                 135                 140

Lys Asp Tyr Ile Ala Leu Asn Glu Asp Leu Arg Ser Trp Thr Ala Ala
145                 150                 155                 160

Asp Lys Ala Ala Gln Ile Thr Gln Arg Lys Trp Glu Ala Ala Arg Glu
                165                 170                 175

Ala Glu Gln Arg Arg Ala Tyr Leu Glu Gly Thr Cys Val Glu Trp Leu
            180                 185                 190

Arg Arg Tyr Leu Glu Asn Gly Lys Lys Thr Leu Gln Arg Ala Glu His
        195                 200                 205

Pro Lys Thr His Val Thr His His Pro Val Ser Asp His Glu Ala Thr
    210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Thr Leu Arg Trp Gly Pro Ser Ser Gln Pro
    290                 295                 300
```

-continued

```
Thr Ile Pro Ile Val Gly Ile Val Ala Gly Leu Ala Val Leu Ala Val
305                 310                 315                 320

Leu Ala Val Leu Gly Ala Val Met Ala Val Met Cys Arg Arg Lys
                325                 330                 335

Ser Ser Gly Gly Lys Gly Gly Ser Cys Ser Gln Ala Ala Ser Ser Asn
            340                 345                 350

Ser Ala Gln Gly Ser Asp Val Ser Leu Thr Ala Cys Lys Ala Arg Ala
            355                 360                 365

Lys Arg Ser Gly Ser Gly Ala Pro Val Lys Gln Thr Leu Asn Phe Asp
        370                 375                 380

Leu Leu Lys Leu Ala Gly Asp Val Glu Ser Asn Pro Gly Pro Met Lys
385                 390                 395                 400

Gly Ser Ile Phe Thr Leu Phe Leu Phe Ser Val Leu Phe Ala Ile Ser
                405                 410                 415

Glu Val Arg Ser Gly Ala Asp Gly Val Gly Lys Ser Ala Arg Arg Lys
            420                 425                 430

Arg Arg Arg Lys Arg Gly Ala Asp Gly Val Gly Lys Ser Ala Arg Arg
        435                 440                 445

Lys Arg Gly Ala Asp Gly Val Gly Lys Ser Ala Arg Arg Lys Arg Lys
    450                 455                 460

Asp Glu Leu
465

<210> SEQ ID NO 26
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NY-ESO-1 157-165 peptide specific TCR example
      #1, alpha chain and beta chain with murine constant region and
      connected with a self-cleaving linker peptide

<400> SEQUENCE: 26

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160
```

-continued

```
Leu Val Cys Leu Ala Arg Gly Phe Phe Pro Asp His Val Glu Leu Ser
            165                 170                 175
Trp Trp Val Asn Gly Lys Glu Val His Ser Gly Val Ser Thr Asp Pro
            180                 185                 190
Gln Ala Tyr Lys Glu Ser Asn Tyr Ser Tyr Cys Leu Ser Ser Arg Leu
            195                 200                 205
Arg Val Ser Ala Thr Phe Trp His Asn Pro Arg Asn His Phe Arg Cys
            210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
Ala Asp Cys Gly Ile Thr Ser Ala Ser Tyr Gln Gln Gly Val Leu Ser
            260                 265                 270
Ala Thr Ile Leu Tyr Glu Ile Leu Leu Gly Lys Ala Thr Leu Tyr Ala
            275                 280                 285
Val Leu Val Ser Thr Leu Val Val Met Ala Met Val Lys Arg Lys Asn
            290                 295                 300
Ser Arg Ala Lys Arg Ser Gly Ser Gly Ala Pro Val Lys Gln Thr Leu
305                 310                 315                 320
Asn Phe Asp Leu Leu Lys Leu Ala Gly Asp Val Glu Ser Asn Pro Gly
                325                 330                 335
Pro Met Glu Thr Leu Leu Gly Leu Leu Ile Leu Trp Leu Gln Leu Gln
            340                 345                 350
Trp Val Ser Ser Lys Gln Glu Val Thr Gln Ile Pro Ala Ala Leu Ser
            355                 360                 365
Val Pro Glu Gly Glu Asn Leu Val Leu Asn Cys Ser Phe Thr Asp Ser
            370                 375                 380
Ala Ile Tyr Asn Leu Gln Trp Phe Arg Gln Asp Pro Gly Lys Gly Leu
385                 390                 395                 400
Thr Ser Leu Leu Leu Ile Gln Ser Ser Gln Arg Glu Gln Thr Ser Gly
                405                 410                 415
Arg Leu Asn Ala Ser Leu Asp Lys Ser Ser Gly Arg Ser Thr Leu Tyr
            420                 425                 430
Ile Ala Ala Ser Gln Pro Gly Asp Ser Ala Thr Tyr Leu Cys Ala Val
            435                 440                 445
Arg Pro Leu Tyr Gly Gly Ser Tyr Ile Pro Thr Phe Gly Arg Gly Thr
            450                 455                 460
Ser Leu Ile Val His Pro Tyr Ile Gln Asn Pro Glu Pro Ala Val Tyr
465                 470                 475                 480
Gln Leu Lys Asp Pro Arg Ser Gln Asp Ser Thr Leu Cys Leu Phe Thr
            485                 490                 495
Asp Phe Asp Ser Gln Ile Asn Val Pro Lys Thr Met Glu Ser Gly Thr
            500                 505                 510
Phe Ile Thr Asp Lys Thr Val Leu Asp Met Lys Ala Met Asp Ser Lys
            515                 520                 525
Ser Asn Gly Ala Ile Ala Trp Ser Asn Gln Thr Ser Phe Thr Cys Gln
            530                 535                 540
Asp Ile Phe Lys Glu Thr Asn Ala Thr Tyr Pro Ser Ser Asp Val Pro
545                 550                 555                 560
Cys Asp Ala Thr Leu Thr Glu Lys Ser Phe Glu Thr Asp Met Asn Leu
                565                 570                 575
```

-continued

```
Asn Phe Gln Asn Leu Ser Val Met Gly Leu Arg Ile Leu Leu Leu Lys
                580                 585                 590
Val Ala Gly Phe Asn Leu Leu Met Thr Leu Arg Leu Trp Ser Ser
        595                 600                 605

<210> SEQ ID NO 27
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NY-ESO-1 157-165 peptide specific TCR example
      #2, alpha chain and beta chain with murine constant region and
      connected with a self-cleaving linker peptide

<400> SEQUENCE: 27

Met Ser Ile Gly Leu Leu Cys Cys Ala Ala Leu Ser Leu Leu Trp Ala
1               5                   10                  15
Gly Pro Val Asn Ala Gly Val Thr Gln Thr Pro Lys Phe Gln Val Leu
            20                  25                  30
Lys Thr Gly Gln Ser Met Thr Leu Gln Cys Ala Gln Asp Met Asn His
        35                  40                  45
Glu Tyr Met Ser Trp Tyr Arg Gln Asp Pro Gly Met Gly Leu Arg Leu
    50                  55                  60
Ile His Tyr Ser Val Ala Glu Gly Ile Thr Asp Gln Gly Glu Val Pro
65                  70                  75                  80
Asn Gly Tyr Asn Val Ser Arg Ser Thr Thr Glu Asp Phe Pro Leu Arg
                85                  90                  95
Leu Leu Ser Ala Ala Pro Ser Gln Thr Ser Val Tyr Phe Cys Ala Ser
            100                 105                 110
Ser Tyr Val Gly Asn Thr Gly Glu Leu Phe Phe Gly Glu Gly Ser Arg
        115                 120                 125
Leu Thr Val Leu Glu Asp Leu Arg Asn Val Thr Pro Pro Lys Val Ser
    130                 135                 140
Leu Phe Glu Pro Ser Lys Ala Glu Ile Ala Asn Lys Gln Lys Ala Thr
145                 150                 155                 160
Leu Val Cys Leu Ala Arg Gly Phe Phe Pro Asp His Val Glu Leu Ser
                165                 170                 175
Trp Trp Val Asn Gly Lys Glu Val His Ser Gly Val Ser Thr Asp Pro
            180                 185                 190
Gln Ala Tyr Lys Glu Ser Asn Tyr Ser Tyr Cys Leu Ser Ser Arg Leu
        195                 200                 205
Arg Val Ser Ala Thr Phe Trp His Asn Pro Arg Asn His Phe Arg Cys
    210                 215                 220
Gln Val Gln Phe His Gly Leu Ser Glu Glu Asp Lys Trp Pro Glu Gly
225                 230                 235                 240
Ser Pro Lys Pro Val Thr Gln Asn Ile Ser Ala Glu Ala Trp Gly Arg
                245                 250                 255
Ala Asp Cys Gly Ile Thr Ser Ala Ser Tyr Gln Gln Gly Val Leu Ser
            260                 265                 270
Ala Thr Ile Leu Tyr Glu Ile Leu Leu Gly Lys Ala Thr Leu Tyr Ala
        275                 280                 285
Val Leu Val Ser Thr Leu Val Val Met Ala Met Val Lys Arg Lys Asn
    290                 295                 300
```

```
Ser Arg Ala Lys Arg Ser Gly Ser Gly Ala Pro Val Lys Gln Thr Leu
305                 310                 315                 320

Asn Phe Asp Leu Leu Lys Leu Ala Gly Asp Val Glu Ser Asn Pro Gly
            325                 330                 335

Pro Met Glu Thr Leu Leu Gly Leu Leu Ile Leu Trp Leu Gln Leu Gln
                340                 345                 350

Trp Val Ser Ser Lys Gln Glu Val Thr Gln Ile Pro Ala Ala Leu Ser
            355                 360                 365

Val Pro Glu Gly Glu Asn Leu Val Leu Asn Cys Ser Phe Thr Asp Ser
        370                 375                 380

Ala Ile Tyr Asn Leu Gln Trp Phe Arg Gln Asp Pro Gly Lys Gly Leu
385                 390                 395                 400

Thr Ser Leu Leu Leu Ile Gln Ser Ser Gln Arg Glu Gln Thr Ser Gly
                405                 410                 415

Arg Leu Asn Ala Ser Leu Asp Lys Ser Ser Gly Arg Ser Thr Leu Tyr
            420                 425                 430

Ile Ala Ala Ser Gln Pro Gly Asp Ser Ala Thr Tyr Leu Cys Ala Val
        435                 440                 445

Arg Pro Thr Ser Gly Gly Ser Tyr Ile Pro Thr Phe Gly Arg Gly Thr
450                 455                 460

Ser Leu Ile Val His Pro Tyr Ile Gln Asn Pro Glu Pro Ala Val Tyr
465                 470                 475                 480

Gln Leu Lys Asp Pro Arg Ser Gln Asp Ser Thr Leu Cys Leu Phe Thr
                485                 490                 495

Asp Phe Asp Ser Gln Ile Asn Val Pro Lys Thr Met Glu Ser Gly Thr
            500                 505                 510

Phe Ile Thr Asp Lys Thr Val Leu Asp Met Lys Ala Met Asp Ser Lys
        515                 520                 525

Ser Asn Gly Ala Ile Ala Trp Ser Asn Gln Thr Ser Phe Thr Cys Gln
530                 535                 540

Asp Ile Phe Lys Glu Thr Asn Ala Thr Tyr Pro Ser Ser Asp Val Pro
545                 550                 555                 560

Cys Asp Ala Thr Leu Thr Glu Lys Ser Phe Glu Thr Asp Met Asn Leu
                565                 570                 575

Asn Phe Gln Asn Leu Ser Val Met Gly Leu Arg Ile Leu Leu Leu Lys
            580                 585                 590

Val Ala Gly Phe Asn Leu Leu Met Thr Leu Arg Leu Trp Ser Ser
        595                 600                 605
```

<210> SEQ ID NO 28
<211> LENGTH: 602
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: NY-ESO-1 157-165 peptide specific TCR example #3, alpha chain and beta chain with murine constant region and connected with a self-cleaving linker peptide

<400> SEQUENCE: 28

```
Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30
```

```
Glu Met Gly Gln Glu Val Thr Leu Arg Cys Lys Pro Ile Ser Gly His
             35                  40                  45

Asp Tyr Leu Phe Trp Tyr Arg Gln Thr Met Met Arg Gly Leu Glu Leu
 50                  55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
                 100                 105                 110

Ser Ser Leu Gly Ser Asn Glu Gln Tyr Phe Gly Pro Gly Thr Arg Leu
             115                 120                 125

Thr Val Thr Glu Asp Leu Arg Asn Val Thr Pro Pro Lys Val Ser Leu
             130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                 165                 170                 175

Trp Val Asn Gly Lys Glu Val His Ser Gly Val Ser Thr Asp Pro Gln
             180                 185                 190

Ala Tyr Lys Glu Ser Asn Tyr Ser Tyr Cys Leu Ser Ser Arg Leu Arg
             195                 200                 205

Val Ser Ala Thr Phe Trp His Asn Pro Arg Asn His Phe Arg Cys Gln
210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                 245                 250                 255

Asp Cys Gly Ile Thr Ser Ala Ser Tyr Gln Gln Gly Val Leu Ser Ala
                 260                 265                 270

Thr Ile Leu Tyr Glu Ile Leu Leu Gly Lys Ala Thr Leu Tyr Ala Val
             275                 280                 285

Leu Val Ser Thr Leu Val Val Met Ala Met Val Lys Arg Lys Asn Ser
             290                 295                 300

Arg Ala Lys Arg Ser Gly Ser Gly Ala Pro Val Lys Gln Thr Leu Asn
305                 310                 315                 320

Phe Asp Leu Leu Lys Leu Ala Gly Asp Val Glu Ser Asn Pro Gly Pro
                 325                 330                 335

Met Glu Thr Leu Leu Gly Val Ser Leu Val Ile Leu Trp Leu Gln Leu
                 340                 345                 350

Ala Arg Val Asn Ser Gln Gln Gly Glu Glu Asp Pro Gln Ala Leu Ser
                 355                 360                 365

Ile Gln Glu Gly Glu Asn Ala Thr Met Asn Cys Ser Tyr Lys Thr Ser
                 370                 375                 380

Ile Asn Asn Leu Gln Trp Tyr Arg Gln Asn Ser Gly Arg Gly Leu Val
385                 390                 395                 400

His Leu Ile Leu Ile Arg Ser Asn Glu Arg Glu Lys His Ser Gly Arg
                 405                 410                 415

Leu Arg Val Thr Leu Asp Thr Ser Lys Lys Ser Ser Ser Leu Leu Ile
                 420                 425                 430

Thr Ala Ser Arg Ala Ala Asp Thr Ala Ser Tyr Phe Cys Met Tyr Asp
             435                 440                 445
```

```
Gln Asn Gly Lys Ile Ile Phe Gly Lys Gly Thr Arg Leu His Ile Leu
    450                 455                 460
Pro Asn Ile Gln Asn Pro Glu Pro Ala Val Tyr Gln Leu Lys Asp Pro
465                 470                 475                 480
Arg Ser Gln Asp Ser Thr Leu Cys Leu Phe Thr Asp Phe Asp Ser Gln
                485                 490                 495
Ile Asn Val Pro Lys Thr Met Glu Ser Gly Thr Phe Ile Thr Asp Lys
                500                 505                 510
Thr Val Leu Asp Met Lys Ala Met Asp Ser Lys Ser Asn Gly Ala Ile
            515                 520                 525
Ala Trp Ser Asn Gln Thr Ser Phe Thr Cys Gln Asp Ile Phe Lys Glu
530                 535                 540
Thr Asn Ala Thr Tyr Pro Ser Ser Asp Val Pro Cys Asp Ala Thr Leu
545                 550                 555                 560
Thr Glu Lys Ser Phe Glu Thr Asp Met Asn Leu Asn Phe Gln Asn Leu
                565                 570                 575
Ser Val Met Gly Leu Arg Ile Leu Leu Leu Lys Val Ala Gly Phe Asn
                580                 585                 590
Leu Leu Met Thr Leu Arg Leu Trp Ser Ser
            595                 600

<210> SEQ ID NO 29
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: KRAS: G12D 10-18 peptide specific TCR example,
      alpha chain and beta chain with murine constant region and
      connected with a self-cleaving linker peptide

<400> SEQUENCE: 29

Met Gly Pro Gly Leu Leu Cys Trp Ala Leu Leu Cys Leu Leu Gly Ala
1               5                   10                  15
Gly Leu Val Asp Ala Gly Val Thr Gln Ser Pro Thr His Leu Ile Lys
            20                  25                  30
Thr Arg Gly Gln Gln Val Thr Leu Arg Cys Ser Pro Lys Ser Gly His
        35                  40                  45
Asp Thr Val Ser Trp Tyr Gln Gln Ala Leu Gly Gln Gly Pro Gln Phe
    50                  55                  60
Ile Phe Gln Tyr Tyr Glu Glu Glu Arg Gln Arg Gly Asn Phe Pro
65                  70                  75                  80
Asp Arg Phe Ser Gly His Gln Phe Pro Asn Tyr Ser Ser Glu Leu Asn
                85                  90                  95
Val Asn Ala Leu Leu Leu Gly Asp Ser Ala Leu Tyr Leu Cys Ala Ser
            100                 105                 110
Ser Leu Gly Glu Gly Arg Val Asp Gly Tyr Thr Phe Gly Ser Gly Thr
        115                 120                 125
Arg Leu Thr Val Val Glu Asp Leu Arg Asn Val Thr Pro Pro Lys Val
    130                 135                 140
Ser Leu Phe Glu Pro Ser Lys Ala Glu Ile Ala Asn Lys Gln Lys Ala
145                 150                 155                 160
Thr Leu Val Cys Leu Ala Arg Gly Phe Phe Pro Asp His Val Glu Leu
                165                 170                 175
```

```
Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
            210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
                260                 265                 270

Ser Ala Thr Ile Leu Tyr Glu Ile Leu Leu Gly Lys Ala Thr Leu Tyr
            275                 280                 285

Ala Val Leu Val Ser Thr Leu Val Val Met Ala Met Val Lys Arg Lys
            290                 295                 300

Asn Ser Arg Ala Lys Arg Ser Gly Ser Gly Ala Pro Val Lys Gln Thr
305                 310                 315                 320

Leu Asn Phe Asp Leu Leu Lys Leu Ala Gly Asp Val Glu Ser Asn Pro
                325                 330                 335

Gly Pro Met Arg Gln Val Ala Arg Val Ile Val Phe Leu Thr Leu Ser
                340                 345                 350

Thr Leu Ser Leu Ala Lys Thr Thr Gln Pro Ile Ser Met Asp Ser Tyr
            355                 360                 365

Glu Gly Gln Glu Val Asn Ile Thr Cys Ser His Asn Asn Ile Ala Thr
            370                 375                 380

Asn Asp Tyr Ile Thr Trp Tyr Gln Gln Phe Pro Ser Gln Gly Pro Arg
385                 390                 395                 400

Phe Ile Ile Gln Gly Tyr Lys Thr Lys Val Thr Asn Glu Val Ala Ser
                405                 410                 415

Leu Phe Ile Pro Ala Asp Arg Lys Ser Ser Thr Leu Ser Leu Pro Arg
                420                 425                 430

Val Ser Leu Ser Asp Thr Ala Val Tyr Tyr Cys Leu Val Gly Asp Met
            435                 440                 445

Asp Gln Ala Gly Thr Ala Leu Ile Phe Gly Lys Gly Thr Thr Leu Ser
            450                 455                 460

Val Ser Ser Ile Gln Asn Pro Glu Pro Ala Val Tyr Gln Leu Lys Asp
465                 470                 475                 480

Pro Arg Ser Gln Asp Ser Thr Leu Cys Leu Phe Thr Asp Phe Asp Ser
                485                 490                 495

Gln Ile Asn Val Pro Lys Thr Met Glu Ser Gly Thr Phe Ile Thr Asp
            500                 505                 510

Lys Thr Val Leu Asp Met Lys Ala Met Asp Ser Lys Ser Asn Gly Ala
            515                 520                 525

Ile Ala Trp Ser Asn Gln Thr Ser Phe Thr Cys Gln Asp Ile Phe Lys
            530                 535                 540

Glu Thr Asn Ala Thr Tyr Pro Ser Ser Asp Val Pro Cys Asp Ala Thr
545                 550                 555                 560

Leu Thr Glu Lys Ser Phe Glu Thr Asp Met Asn Leu Asn Phe Gln Asn
                565                 570                 575
```

```
Leu Ser Val Met Gly Leu Arg Ile Leu Leu Lys Val Ala Gly Phe
        580                 585                 590
Asn Leu Leu Met Thr Leu Arg Leu Trp Ser Ser
        595                 600
```

<210> SEQ ID NO 30
<211> LENGTH: 1824
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid: NY-ESO-1 157-165 peptide
      specific TCR example TCR-NY-LY, alpha chain and beta chain with
      murine constant region and connected with a self-cleaving linker
      peptide

<400> SEQUENCE: 30

```
atgagcatcg gcctcctgtg ctgtgcagcc ttgtctctcc tgtgggcagg tccagtgaat      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcagtt acgtcgggaa caccggggag     360
ctgttttttg gagaaggctc taggctgacc gtactggagg atctgagaaa tgtgactcca     420
cccaaggtct ccttgtttga gccatcaaaa gcagagattg caaacaaaca aaaggctacc     480
ctcgtgtgct tggccagggg cttcttccct gaccacgtgg agctgagctg gtgggtgaat     540
ggcaaggagg tccacagtgg ggtcagcacg gaccctcagg cctacaagga gagcaattat     600
agctactgcc tgagcagccg cctgagggtc tctgctacct tctggcacaa tcctcgcaac     660
cacttccgct gccaagtgca gttccatggg ctttcagagg aggacaagtg ccagagggc     720 tcacccaaac ctgtcacaca gaacatcagt gcagaggcct ggggccgagc agactgtggg     780
attacctcag catcctatca acaaggggtc ttgtctgcca ccatcctcta tgagatcctg     840
ctagggaaag ccaccctgta tgctgtgctt gtcagtacac tggtggtgat ggctatggtc     900
aaaagaaaga attcacgtgc caagcgatcc ggaagcggag ccctgtaaa gcagactttg     960 aattttgacc ttctcaagtt ggcgggagac gtcgagtcca accctgggcc catggagacc    1020
ctcttgggcc tgcttatcct ttggctgcag ctgcaatggg tgagcagcaa acaggaggtg    1080
acacagattc ctgcagctct gagtgtccca gaaggagaaa acttggttct caactgcagt    1140
ttcactgata gcgctattta caacctccag tggtttaggc aggaccctgg aaaggtctc    1200 acatctctgt tgcttattca gtcaagtcag agagagcaaa caagtggaag acttaatgcc    1260
tcgctggata atcatcagg acgtagtact ttatacattg cagcttctca gcctggtgac    1320
tcagccacct acctctgtgc tgtgaggccc tgtacggaga agctacat acctacattt    1380 ggaagaggaa ccagccttat tgttcatccg tatatccaga cccagaacc tgctgtgtac    1440 cagttaaaag atcctcggtc tcaggacagc accctctgcc tgttcaccga ctttgactcc    1500
caaatcaatg tgccgaaaac catggaatct ggaacgttca tcactgacaa actgtgctg    1560 gacatgaaag ctatggattc caagagcaat gggccattg cctggagcaa ccagacaagc    1620
ttcacctgcc aagatatctt caagagacc aacgccacct accccagttc agacgttccc    1680
tgtgatgcca cgttgaccga gaaagctt gaaacagata tgaacctaaa ctttcaaaac    1740
```

```
ctgtcagtta tgggactccg aatcctcctg ctgaaagtag cgggatttaa cctgctcatg    1800
acgctgaggc tgtggtccag ttga                                           1824
```

<210> SEQ ID NO 31
<211> LENGTH: 1824
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid: NY-ESO-1 157-165 peptide
      specific TCR example TCR-NY-AE, alpha chain and beta chain with
      murine constant region and connected with a self-cleaving linker
      peptide

<400> SEQUENCE: 31

```
atgagcatcg gcctcctgtg ctgtgcagcc ttgtctctcc tgtgggcagg tccagtgaat     60
gctggtgtca ctcagacccc aaaattccag gtcctgaaga caggacagag catgacactg    120
cagtgtgccc aggatatgaa ccatgaatac atgtcctggt atcgacaaga cccaggcatg    180
gggctgaggc tgattcatta ctcagttgct gaaggtatca ctgaccaagg agaagtcccc    240
aatggctaca atgtctccag atcaaccaca gaggatttcc cgctcaggct gctgtcggct    300
gctccctccc agacatctgt gtacttctgt gccagcagtt acgtcgggaa caccggggag    360
ctgttttttg gagaaggctc taggctgacc gtactggagg atctgagaaa tgtgactcca    420
cccaaggtct ccttgtttga gccatcaaaa gcagagattg caaacaaaca aaaggctacc    480
ctcgtgtgct tggccagggg cttcttccct gaccacgtgg agctgagctg gtgggtgaat    540
ggcaaggagg tccacagtgg ggtcagcacg gaccctcagg cctacaagga gagcaattat    600
agctactgcc tgagcagccg cctgagggtc tctgctacct tctggcacaa tcctcgcaac    660
cacttccgct gccaagtgca gttccatggg ctttcagagg aggacaagtg ccagagggc    720 tcacccaaac ctgtcacaca gaacatcagt gcagaggcct ggggccgagc agactgtggg    780
attacctcag catcctatca acaaggggtc ttgtctgcca ccatcctcta tgagatcctg    840
ctagggaaag ccaccctgta tgctgtgctt gtcagtacac tggtggtgat ggctatggtc    900
aaaagaaaga attcacgtgc caagcgatcc ggaagcggag cccctgtaaa gcagactttg    960
aattttgacc ttctcaagtt ggcgggagac gtcgagtcca accctggcc catggagacc   1020 ctcttgggcc tgcttatcct ttggctgcag ctgcaatggg tgagcagcaa acaggaggtg   1080
acacagattc ctgcagctct gagtgtccca gaaggagaaa acttggttct caactgcagt   1140
ttcactgata gcgctattta caacctccag tggtttaggc aggaccctgg aaaggtctc   1200 acatctctgt tgcttattca gtcaagtcag agagagcaaa caagtggaag acttaatgcc   1260
tcgctggata atcatcagg acgtagtact ttatacattg cagcttctca gcctggtgac   1320
tcagccacct acctctgtgc tgtgaggccc acatcaggag gaagctacat acctacattt   1380
ggaagaggaa ccagccttat tgttcatccg tatatccaga acccagaacc tgctgtgtac   1440
cagttaaaag atcctcggtc tcaggacagc accctctgcc tgttcaccga ctttgactcc   1500
caaatcaatg tgccgaaaac catggaatct ggaacgttca tcactgacaa actgtgctg   1560 gacatgaaag ctatggattc caagagcaat ggggccattg cctggagcaa ccagacaagc   1620
ttcacctgcc aagatatctt caagagacc aacgccacct accccagttc agacgttccc   1680
tgtgatgcca cgttgaccga gaaaagcttt gaaacagata tgaacctaaa ctttcaaaac   1740
```

```
ctgtcagtta tgggactccg aatcctcctg ctgaaagtag cgggatttaa cctgctcatg    1800
acgctgaggc tgtggtccag ttga                                            1824

<210> SEQ ID NO 32
<211> LENGTH: 1809
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid: NY-ESO-1 157-165 peptide
      specific TCR example TCR-NY-LI, alpha chain and beta chain with
      murine constant region and connected with a self-cleaving linker
      peptide

<400> SEQUENCE: 32
atgggctcct ggaccctctg ctgtgtgtcc ctttgcatcc tggtagcaaa gcacacagat     60
gctggagtta tccagtcacc ccggcacgag gtgacagaga tgggacaaga agtgactctg    120
agatgtaaac caatttcagg acacgactac ctttctggt acagacagac catgatgcgg    180
ggactggagt tgctcattta ctttaacaac aacgttccga tagatgattc agggatgccc    240
gaggatcgat tctcagctaa gatgcctaat gcatcattct ccactctgaa gatccagccc    300
tcagaaccca gggactcagc tgtgtacttc tgtgccagca gtttaggctc aacgagcag    360 tacttcgggc cggcaccag ctcacggtc acagaggatc tgagaaatgt gactccaccc    420
aaggtctcct tgtttgagcc atcaaaagca gagattgcaa acaaacaaaa ggctacctc    480 gtgtgcttgg ccaggggctt cttccctgac acgtggagc tgagctggtg ggtgaatggc    540
aaggaggtcc acagtggggt cagcacggac cctcaggcct acaaggagag caattatag    600 tactgcctga gcagccgcct gagggtctct gctaccttct ggcacaatcc tcgcaaccac    660
ttccgctgcc aagtgcagtt ccatgggctt tcagaggagg acaagtggcc agagggctca    720
cccaaacctg tcacacagaa catcagtgca gaggcctggg gccgagcaga ctgtgggatt    780
acctcagcat cctatcaaca agggtcttg tctgccacca tcctctatga gatcctgcta    840
gggaaagcca ccctgtatgc tgtgcttgtc agtacactgg tggtgatggc tatggtcaaa    900
agaaagaatt cacgtgccaa gcgatccgga agcggagccc tgtaaagca gactttgaat    960 tttgaccttc tcaagttggc gggagacgtc gagtccaacc ctgggcccat ggaaactctc    1020
ctgggagtgt ctttggtgat tctatggctt caactggcta gggtgaacag tcaacaggga    1080
gaagaggatc ctcaggcctt gagcatccag gagggtgaaa atgccaccat gaactgcagt    1140
tacaaaacta gtataaacaa tttacagtgg tatagacaaa attcaggtag aggccttgtc    1200
cacctaattt taatacgttc aaatgaaaga gagaaacaca gtggaagatt aagagtcacg    1260
cttgacactt ccaagaaaag cagttccttg ttgatcacgg cttcccgggc agcagacact    1320
gcttcttact tctgtatgta cgaccagaac ggcaagatca tctttggaaa agggacacga    1380
cttcatattc tccccaatat ccagaaccca gaacctgctg tgtaccagtt aaaagatcct    1440
cggtctcagg acagcaccct ctgcctgttc accgactttg actcccaaat caatgtgccg    1500
aaaaccatgg aatctggaac gttcatcact gacaaaactg tgctggacat gaaagctatg    1560
gattccaaga gcaatgggc cattgcctgg agcaaccaga caagcttcac ctgccaagat    1620
atcttcaaag agaccaacgc cacctacccc agttcagacg ttccctgtga tgccacgttg    1680
accgagaaaa gctttgaaac agatatgaac ctaaacttc aaaacctgtc agttatggga    1740
```

```
ctccgaatcc tcctgctgaa agtagcggga tttaacctgc tcatgacgct gaggctgtgg    1800
tccagttga                                                             1809

<210> SEQ ID NO 33
<211> LENGTH: 1812
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid: KRAS: G12D 10-18 peptide
      specific TCR-RAS-G12D, alpha chain and beta chain with murine
      constant region and connected with a self-cleaving linker peptide

<400> SEQUENCE: 33
atgggccccg ggctcctctg ctgggcactg ctttgtctcc tgggagcagg cttagtggac      60
gctggagtca cccaaagtcc cacacacctg atcaaaacga gaggacagca agtgactctg     120
agatgctctc ctaagtctgg gcatgacact gtgtcctggt accaacaggc cctgggtcag     180 gggcccagt ttatctttca gtattatgag gaggaagaga gacagagagg caacttccct      240
gatcgattct caggtcacca gttccctaac tatagctctg agctgaatgt gaacgccttg     300
ttgctggggg actcggccct ctatctctgt gccagcagct gggtgaggg aagagtggac      360 ggctacacct tcggttcggg gaccaggtta accgttgtag aggatctgag aaatgtgact     420
ccacccaagg tctccttgtt tgagccatca aaagcagaga ttgcaaacaa acaaaaggct     480
accctcgtgt gcttggccag ggcttcttc cctgaccacg tggagctgag ctggtgggtg      540
aatggcaagg aggtccacag tggggtcagc acggaccctc aggcctacaa ggagagcaat     600
tatagctact gcctgagcag ccgcctgagg gtctctgcta ccttctggca caatcctcgc     660
aaccacttcc gctgccaagt gcagttccat gggctttcag aggaggacaa gtggccagag     720
ggctcaccca aacctgtcac acagaacatc agtgcagagg cctggggccg agcagactgt     780
gggattacct cagcatccta tcaacaaggg gtcttgtctg ccaccatcct ctatgagatc     840
ctgctaggga aagccaccct gtatgctgtg cttgtcagta cactggtggt gatggctatg     900
gtcaaaagaa agaattcacg tgccaagcga tccggaagcg gagcccctgt aaagcagact     960
ttgaattttg accttctcaa gttggcggga gacgtcgagt ccaaccctgg gcccatgagg    1020
caagtggcga gagtgatcgt gttcctgacc ctgagtactt tgagccttgc taagaccacc    1080
cagcccatct ccatggactc atatgaagga caagaagtga acataacctg tagccacaac    1140
aacattgcta caaatgatta tatcacgtgg taccaacagt ttcccagcca aggaccacga    1200
tttattattc aaggatacaa gacaaaagtt acaaacgaag tggcctccct gtttatccct    1260
gccgacagaa agtccagcac tctgagcctg ccccgggttt ccctgagcga cactgctgtg    1320
tactactgcc tcgtgggtga catggatcag gcaggaactg ctctgatctt tgggaaggga    1380
accaccttat cagtgagttc catccagaac ccagaacctg ctgtgtacca gttaaaagat    1440
cctcggtctc aggacagcac cctctgcctg ttcaccgact tgactcccca aatcaatgtg    1500
ccgaaaacca tggaatctgg aacgttcatc actgacaaaa ctgtgctgga catgaaagct    1560
atggattcca gagcaatggg ggccattgcc tggagcaacc agacaagctt cacctgccaa    1620
gatatcttca aagagaccaa cgccacctac cccagttcag acgttccctg tgatgccacg    1680
ttgaccgaga aaagctttga aacagatatg aacctaaact ttcaaaacct gtcagttatg    1740
```

```
ggactccgaa tcctcctgct gaaagtagcg ggatttaacc tgctcatgac gctgaggctg    1800
tggtccagtt ga                                                        1812

<210> SEQ ID NO 34
<211> LENGTH: 984
<212> TYPE: DNA
<213> ORGANISM: Human adenovirus 5
<220> FEATURE:
<223> OTHER INFORMATION: Type 5 Adenovirus E1A genomic sequence wild
      type

<400> SEQUENCE: 34
atgagacata ttatctgcca cggaggtgtt attaccgaag aaatggccgc cagtcttttg     60
gaccagctga tcgaagaggt actggctgat aatcttccac ctcctagcca ttttgaacca    120
cctacccttc acgaactgta tgatttagac gtgacggccc ccgaagatcc caacgaggag    180
gcggtttcgc agatttttcc cgagtctgta atgttggcgg tgcaggaagg gattgactta    240
ttcacttttc cgccggcgcc cggttctccg gagccgcctc acctttcccg gcagcccgag    300
cagccggagc agagagcctt gggtccggtt tctatgccaa ccttgtgcc ggaggtgatc     360 gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cggggaccc agatattatg tgttcgcttt gctatatgag gacctgtggc     540
atgtttgtct acagtaagtg aaaattatgg gcagtcggtg atagagtggt gggtttggtg    600
tggtaatttt tttttaattt ttacagtttt gtggtttaaa gattttgta ttgtgatttt     660 ttaaaaggtc ctgtgtctga acctgagcct gagcccgagc cagaaccgga gcctgcaaga    720
cctacccggc gtcctaaatt ggtgcctgct atcctgagac gcccgacatc acctgtgtct    780
agagaatgca atagtagtac ggatagctgt gactccggtc cttctaacac acctcctgag    840
atacacccgg tggtcccgct gtgccccatt aaaccagttg ccgtgagagt tggtgggcgt    900
cgccaggctg tggaatgtat cgaggacttg cttaacgagt ctgggcaacc tttggacttg    960
agctgtaaac gccccaggcc ataa                                           984

<210> SEQ ID NO 35
<211> LENGTH: 1365
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotide sequence encoding the labelling
      polypeptide containing NY-ESO-1 157-165 and HLA-A2

<400> SEQUENCE: 35
atgaaaggtt ccatcttcac attgttttg ttctccgtat tgttcgcaat cagcgaagtc      60
cgatcatccc tgttgatgtg gatcacgcag tgccgcagaa agaggtcact cttaatgtgg    120
ataacccaat gtaggcgaaa gagatcgcta ttgatgtgga ttacacagtg tcgtcgtaag    180
cgatccggaa gcggagcccc tgtaaagcag actttgaatt ttgaccttct caagttggcg    240
ggagacgtcg agtccaaccc tgggcccatg gccgtcatgg cgccccgaac cctcgtcctg    300
ctactctcgg gggctctggc cctgacccag acctgggcgg gctctcactc catgaggtat    360
ttcttcacat ccgtgtcccg gcccggccgc ggggagcccc gcttcatcgc agtgggctac    420
gtggacgaca cgcagttcgt gcggttcgac agcgacgccg cgagccagag gatggagccg    480
```

```
cgggcgccgt ggatagagca ggagggtccg gagtattggg acggggagac acggaaagtg      540
aaggcccact cacagactca ccgagtggac ctggggaccc tgcgcggcta ctacaaccag      600
agcgaggccg gttctcacac cgtccagagg atgtatggct gcgacgtggg gtcggactgg      660
cgcttcctcc gcgggtacca ccagtacgcc tacgacggca aggattacat cgccctgaaa      720
gaggacctgc gctcttggac cgcggcggac atggcagctc agaccaccaa gcacaagtgg      780
gaggcggccc atgtggcgga gcagttgaga gcctacctgg agggcacgtg cgtggagtgg      840
ctccgcagat acctggagaa cgggaaggag acgctgcagc gcacggacgc ccccaaaacg      900
catatgactc accacgctgt ctctgaccat gaagccaccc tgaggtgctg ggccctgagc      960
ttctaccctg cggagatcac actgacctgg cagcgggatg gggaggacca gacccaggac     1020
acggagctcg tggagaccag gcctgcaggg gatggaacct tccagaagtg gcggctgtg      1080 gtggtgcctt ctggacagga gcagagatac acctgccatg tgcagcatga gggtttgccc     1140 aagccctca ccctgagatg ggagccgtct cccagccca ccatcccat cgtgggcatc       1200 attgctggcc tggttctctt tggagctgtg atcactggag ctgtggtcgc tgctgtgatc     1260
tggaggagga agagctcaga tagaaaagga gggagctact ctcaggctgc aagcagtgac     1320
agtgcccagg gctctgatgt gtctctcaca gcttgtaaag tgtga                    1365

<210> SEQ ID NO 36
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleotide sequence encoding the linker
      peptide furin-F2A

<400> SEQUENCE: 36
cgtgccaagc gatccggaag cggagcccct gtaaagcaga ctttgaattt tgaccttctc       60
aagttggcgg gagacgtcga gtccaaccct gggccc                                 96

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Furin enzyme cleavage peptide

<400> SEQUENCE: 37

Arg Arg Lys Arg
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: endoplasmic reticulum retention signal sequence

<400> SEQUENCE: 38

Lys Asp Glu Leu
1
```

-continued

```
<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 39
tatataagca gagctgccac catgcaggcc gaaggccggg gca                43

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 40
tgattgtcga cgcccttagc gcctctgccc tgagggaggc tg                 42

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 41
atgactgaat ataaacttgt ggtagttgga gctgacggcg taggcaagag tgccttg   57

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer

<400> SEQUENCE: 42
tgattgtcga cgcccttaca taattacaca ctttgtcttt gacttc             46

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 43
ctcatagcgc gtaatggctc cggtgcccgt cagtgggcag                    40

<210> SEQ ID NO 44
<211> LENGTH: 39
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 44
gaattcgcta gctctagatc acgacacctg aaatggaag                               39

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 45
agagctagcg aattcaacat gaaaggttcc atcttcac                                38

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 46
acactgtgta atccacatca atagcgatct ctttc                                   35

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 47
tggattacac agtgtcgtcg taagcgatcc ggaagcgga                               39

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer

<400> SEQUENCE: 48
cgccatgacg gccatgggcc cagggttgga ctcgacgtc                               39

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Primer

<400> SEQUENCE: 49
atggccgtca tggcgccccg a                                              21

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 50
tcacacttta caagctgtga gagacac                                        27

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer

<400> SEQUENCE: 51
atgaaaggtt ccatcttcac attgtttttg ttc                                 33

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 52
cgccatgacg gccatgggcc cagggttgga ctcgacgtc                           39

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 53
ggaagatctg gactgaaaat gag                                            23

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer
```

```
<400> SEQUENCE: 54
tgaggtcaga tgtaaccaag atta                                              24

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 55
cgcgtcgact actgtaatag taatcaatta cgg                                    33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 56
gacgtcgact aagatacatt gatgagtttg gac                                    33

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 57
atgagacata ttatctgcca cggag                                             25

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 58
catggtggcg aggtcagatg taac                                              24

<210> SEQ ID NO 59
<211> LENGTH: 8
<212> TYPE: PRT
<213> ORGANISM: Human adenovirus 5

<400> SEQUENCE: 59

Leu Thr Cys His Glu Ala Gly Phe
1               5
```